United States Patent [19]

Unger et al.

[11] Patent Number: 5,580,575

[45] Date of Patent: Dec. 3, 1996

[54] THERAPEUTIC DRUG DELIVERY SYSTEMS

[75] Inventors: Evan C. Unger; Thomas A. Fritz; Terry Matsunaga; VaradaRajan Ramaswami; David Yellowhair; Guanli Wu, all of Tucson, Ariz.

[73] Assignee: ImaRx Pharmaceutical Corp., Tucson, Ariz.

[21] Appl. No.: 76,250

[22] Filed: Jun. 11, 1993

Related U.S. Application Data

[63] Continuation-in-part of Ser. No. 716,899, Jun. 18, 1991, abandoned, and a continuation-in-part of Ser. No. 717,084, Jun. 18, 1991, Pat. No. 5,228,446, which is a continuation-in-part of Ser. No. 569,828, Aug. 20, 1990, Pat. No. 5,088,499, which is a continuation-in-part of Ser. No. 455,707, Dec. 22, 1989, abandoned.

[51] Int. Cl.$^6$ ............................................. A61K 9/127
[52] U.S. Cl. ............................................. 424/450
[58] Field of Search ............... 424/450; 425/402.2; 436/829

[56] References Cited

U.S. PATENT DOCUMENTS

| | | | |
|---|---|---|---|
| 3,532,500 | 10/1970 | Priest et al. | 96/91 |
| 3,873,564 | 3/1975 | Schneider et al. | 260/309.6 |

(List continued on next page.)

FOREIGN PATENT DOCUMENTS

| | | |
|---|---|---|
| 0107559 | 5/1984 | European Pat. Off. . |
| 0231091 | 1/1987 | European Pat. Off. . |
| 0272091 | 6/1988 | European Pat. Off. . |
| 0324938 | 6/1988 | European Pat. Off. . |
| 0338971 | 10/1989 | European Pat. Off. . |
| 0361894 | 4/1990 | European Pat. Off. . |
| 0216730 | 1/1991 | European Pat. Off. . |
| 0458745A1 | 11/1991 | European Pat. Off. . |
| 0314764B1 | 9/1992 | European Pat. Off. . |
| 0554213A1 | 8/1993 | European Pat. Off. . |
| 63-60943 | 3/1988 | Japan . |
| 2193095 | 3/1988 | United Kingdom . |
| 80/02365 | 11/1980 | WIPO . |
| 82/01642 | 5/1982 | WIPO . |
| US85/01161 | 3/1985 | WIPO . |
| 86/00238 | 1/1986 | WIPO . |
| 86/01103 | 2/1986 | WIPO . |
| 89/05040 | 6/1989 | WIPO . |
| 90/04943 | 5/1990 | WIPO . |
| 91/00086 | 1/1991 | WIPO . |
| 91/15244 | 10/1991 | WIPO . |
| 92/10166 | 6/1992 | WIPO . |
| 92/17212 | 10/1992 | WIPO . |
| 93/05819 | 1/1993 | WIPO . |
| 93/20802 | 3/1993 | WIPO . |
| 93/06869 | 4/1993 | WIPO . |
| 93/13809 | 7/1993 | WIPO . |

OTHER PUBLICATIONS

Kost et al. Ultrasonic Modulated Drug Delivery Systems *Polymers in Medicine II* Plenum Press New York 387–396.
Brown et al. Transdermal Delivery of Drugs *Ann. Rev. Med.* 1988 39:221–229.
Santaella et al. Extended in vivo blood circulation time of fluorinated liposomes *FEBS* 1993 336:481–484.
Gramiak et al., *Radiology*, "Detection of Intracardiac Blood Flow by Pulsed Echo–Ranging", pp. 415–418 (1971).
Feigenbaum et al., *Circulation*, "Identification of Ultrasound Echoes from the left Ventricle by Use of Intracardiac Injections of Indocyanine Green", vol. XL1, pp. 615–621 (1970).
Stelmashok et al., *Koordinatsionnaya Khimiya*, vol.3, No. 4, pp. 524–527 (1977) (Russian language version).

(List continued on next page.)

*Primary Examiner*—Gollamudi S. Kishore
*Attorney, Agent, or Firm*—Woodcock Washburn Kurtz Mackiewicz & Norris

[57] ABSTRACT

Therapeutic drug delivery systems comprising gas-filled microspheres comprising a therapeutic are described. Methods for employing such microspheres in therapeutic drug delivery applications are also provided. Drug delivery systems comprising gas-filled liposomes having encapsulated therein a drug are preferred. Methods of and apparatus for preparing such liposomes and methods for employing such liposomes in drug delivery applications are also disclosed.

17 Claims, 21 Drawing Sheets

U.S. PATENT DOCUMENTS

| | | | |
|---|---|---|---|
| 4,049,388 | 9/1991 | Knight et al. | 424/450 |
| 4,089,801 | 5/1978 | Schneider | 252/316 |
| 4,162,282 | 7/1979 | Fulwyler et al. | 264/9 |
| 4,187,433 | 1/1988 | Feinstein | 128/660 |
| 4,192,859 | 3/1980 | Mackaness et al. | 424/5 |
| 4,224,179 | 9/1980 | Schneider | 252/316 |
| 4,229,360 | 11/1991 | Schneider et al. | 260/403 |
| 4,276,885 | 7/1981 | Tickner et al. | 128/660 |
| 4,310,505 | 1/1982 | Baldeschwieler et al. | 424/1 |
| 4,315,514 | 2/1982 | Drewes et al. | 128/653 |
| 4,331,654 | 5/1982 | Morris | 424/38 |
| 4,344,929 | 8/1982 | Bonsen et al. | 424/15 |
| 4,426,330 | 1/1984 | Sears | 260/403 |
| 4,442,843 | 4/1984 | Rasor et al. | 128/660 |
| 4,466,442 | 8/1984 | Hilmann et al. | 128/653 |
| 4,533,254 | 8/1985 | Cook et al. | 366/176 |
| 4,534,899 | 8/1985 | Sears | 260/403 |
| 4,544,545 | 10/1985 | Rayan et al. | 424/1.1 |
| 4,569,836 | 2/1986 | Gordon | 424/1/1 |
| 4,572,203 | 2/1986 | Feinstein | 128/661 |
| 4,586,512 | 5/1985 | Do-huu et al. | 126/660 |
| 4,603,044 | 7/1986 | Geho et al. | 424/9 |
| 4,620,546 | 11/1986 | Aida et al. | 128/660 |
| 4,646,756 | 3/1987 | Watmough et al. | 128/804 |
| 4,657,756 | 4/1987 | Rasor et al. | 424/9 |
| 4,658,828 | 4/1987 | Dory | 128/660 |
| 4,675,310 | 6/1987 | Chapman et al. | 514/6 |
| 4,681,119 | 7/1987 | Rasor et al. | 128/660 |
| 4,684,479 | 8/1987 | D'Arrigo | 252/307 |
| 4,689,986 | 9/1987 | Carson et al. | 73/19 |
| 4,728,575 | 3/1988 | Gamble et al. | 428/402.2 |
| 4,728,578 | 3/1988 | Higgins et al. | 428/662 |
| 4,737,323 | 4/1988 | Martin et al. | 264/4.3 |
| 4,774,958 | 10/1988 | Feinstein | 128/660.01 |
| 4,776,991 | 10/1988 | Farmer et al. | 264/4.3 |
| 4,781,871 | 11/1988 | West, III et al. | 264/4.3 |
| 4,790,891 | 12/1988 | Halliday et al. | 149/2 |
| 4,830,858 | 5/1989 | Payne et al. | 424/450 |
| 4,844,882 | 7/1989 | Widder et al. | 424/9 |
| 4,863,717 | 9/1989 | Keana | 424/9 |
| 4,865,836 | 9/1989 | Long, Jr. | 424/5 |
| 4,877,561 | 10/1989 | Iga et al. | 264/4.3 |
| 4,893,624 | 1/1990 | Lele | 424/399 |
| 4,895,719 | 1/1990 | Radhakvishnau | 424/45 |
| 4,898,734 | 2/1990 | Mathiowitz | 424/426 |
| 4,900,540 | 2/1990 | Ryan | 424/9 |
| 4,921,706 | 5/1990 | Roberts et al. | 424/450 |
| 4,927,623 | 5/1990 | Long, Jr. | 424/450 |
| 4,938,947 | 7/1990 | Nicolau et al. | 424/1.1 |
| 4,957,656 | 9/1990 | Cerny et al. | 252/311 |
| 4,987,154 | 1/1991 | Long, Jr. | 514/712 |
| 5,000,960 | 3/1991 | Wallach | 424/450 |
| 5,008,050 | 4/1991 | Cullis et al. | 264/4.3 |
| 5,013,556 | 5/1991 | Woodle et al. | 424/450 |
| 5,045,304 | 9/1991 | Schneider et al. | 424/9 |
| 5,088,499 | 2/1992 | Unger | 128/662.2 |
| 5,144,703 | 5/1992 | Wolf et al. | 424/5 |
| 5,149,319 | 9/1992 | Unger | 604/22 |
| 5,171,755 | 12/1992 | Kaufman | 514/759 |
| 5,194,266 | 3/1993 | Abra et al. | 424/450 |
| 5,195,520 | 3/1993 | Schlief et al. | 128/660.02 |
| 5,198,225 | 3/1993 | Meybeck et al. | 424/450 |
| 5,209,720 | 5/1993 | Unger | 604/22 |
| 5,213,804 | 5/1993 | Martin et al. | 424/450 |
| 5,215,680 | 6/1993 | D'Arrigo | 252/307 |
| 5,219,538 | 6/1993 | Henderson et al. | 428/402.2 |
| 5,271,928 | 12/1993 | Schneider | 426/9 |
| 5,310,540 | 5/1994 | Giddey et al. | 424/9 |
| 5,316,771 | 5/1994 | Barenholtz et al. | 424/450 |
| B1 4,229,360 | 10/1980 | Schneider et al. | 260/403 |

OTHER PUBLICATIONS

Fitzpatrick et al. Metal Ion Catalyzed Decarboxylation: Kinetics and Mechanism fo the Oxidative Decarboxylation of Copper (II) Complexes of Aminomalonic Acid in Aqueous Solution *Inorganic Chem.* 1974 13:568–574.

Thanassi Aminomalonic Acid: Spontaneous Decarboxylationand reaction with 5–Deoxpyridoxal *Biochemistry* 1970 9:525–532.

Stelmashok et al. *Koordinatsionnaya Khimiya* 1977 3:524–527 (English Verison).

Jain et al. *Introduction to Biological Membranes* Ch. 9 192–231 J. Wiley and Sons, NY 1980.

Sigel H. Ed., *Metal Ions in Biological Systems: Antibiotics and Their Complexes* vol. 19 Marcell Dekker NY 1985.

Nayar et al. Generation of Large Unilamellar Vesicles From Long–Chanin Saturated Phosphtidylcholines by Extrusion Techniques *Biochimica et Biophysica Acta* 1989 986:200–206.

Hope et al. Generation of Multilamellar and Unilamellar Phospholipid Vesicles *Chem. Phys. of Lipids* 1986 40:89–107.

Mattrey et al. Perfluorochemicals as US Contrast Agents for Tumor–Imaging and Hepatosplenography: Preliminary Clinical Results *Radiology* 1987 163 339–343.

Mattrey et al. Perfluorocytlbromide: A Liver/Spleen–Specific and Tumor Imaging Ultrasound Contrast Material *Radiology* 1982 145:759–762.

Keller et al. Successful Left Ventricular Opacification Following Peripheral Venous Injection of Sonicated Contrast Agent *LV Contrast Echocardiography* 1987 114:570–575.

Feinstein et al. Two–Dimensional Contrast Echocardiography I *JACC* 1984 3:14–20.

Ten Cate et al. Two–Dimensional Contrast Echocardiography II JACC 1984 3:21–27.

Unger et al. Hepatic Metastases: Lipsomal Gd–DTPA–enhanced MR Imaging *Radiology* 1989 171:81–85.

Deamer et al. Permeability of Lipid Bilayers to Water and Ionic Solutes *Chem. Phys. Lipids* 1986 40:167–188.

Gutknecht et al. Diffusion of Carbon Dioxide Through Lipid Bilayer Membranes *Chemical Abstracts* 1977 87:34772q.

Scarpa et al. Cation Permeability of Liposomes as a Function of the Chmical Composition of the Lipid Bilyares *Biochimica et Biophysica Acta 1971 241 :789–797.*

MacNaughton et al. Effects of Gaseous Anesthetics and Inert Gases on the Phase Transition in Smectic Mesophases of Dipalmitoyl Phosphatidylcholine *Biochim. et Biophy. Acta* 1980 597:193–198.

Tilcock et al. Liposmal GD–DTPA *Radiology* 1989 171:77–80.

Mann et al. Formation of IRon Oxides in Unilamellar Vesicles *Journal of Colloid and Interface Science* 1988 122:326–335.

Anderson et al. Manganese (III) Complexes in Oxidative Decarboxylation of Acids *J. Am. Chem. COs.* 1970 92:2450–2460.

Muhlradt et al. Vitamin B6 Analogs *New Compounds* 1967 10:129–130.

Chapman D. Physiochemical Properties of Phopholipids and Lipid Water Systems *Liposome Technology* 1984 1:1–19.

Violante et al. Particulate Suspensions as Ultrasonic Contrast Agents for Liver and Spleen *Inv. Rad.* 1988 23:S294–S297.

Fritzsch et al. Preclinical and Clinical Results with an Ultrasonic Contrast Agent *Inv. Rad.* 1988 23:S302–S305.

Brochure, Experience, Sonicator, Heat Systems Ultrasonics, Inc. 1987.

Ostro M. Liposomes Marcel Dekker New York 1983 102–103.

Rose A. et al. The Condensed Chemical Dictionary Reinhold Publishing New York 1966 728 and 743.

Belykh A. G. Farmakol Toksikol (*MOSC*) 1981 44:322–326.

Vion–Dury et al. *J. Pharmacol. Exper. Ther.* 1989 250:1113–1118.

Zalutsky et al. *Invest. Radiol.* 1987 22:141–147.

Scientific Apparatus Catalog 92/93 (VWR Scientific, 1991) Syringes pp. 1511 –1513, Filtration, Syringe Filters pp. 766–768, Filtration, membranes pp. 750–753; Filtration, Filters Holders p. 744.

*Acoustic Imaging; AI5200; Convex Curved Linear Array Ultrasound Transducers Operator's Manual*, Nov. 20, 1989, 4700–0003–IC, p. 4.

Bangham et al., "Diffusion of Univalent Ions across the Lamellae of Swollen Phospholipids", *J. Mol. Biol.*, 1965, 13:238–252.

Carson et al., *Ultrasound in Med. & Biol.* 3, 1978, 341–350.

Chapman et al., "Biomembrane Phase Transitions", *J. Biol. Chem.*, 1974, 249:2512–2521.

deGier et al., "Relations Between Liposomes and Biomembranes", *Annals of the New York Academy of Sciences*, 1978, 308:85–99.

Felgner et al., "Lipofection: A highly efficient, lipid–mediated DNA–transfection procedure", *Proc. Natl. Acad. Sci.*, 1987, 84:7413–74 17.

Gabizon et al. "Liposome formlations with prolonged circulation time in blood and enhanced uptake by tumors", *Proc. Natl. Acad. Sci.*, 1988, 85:6949–6953.

Garelli et al., "Incorporation of new amphiphilic perfluoroalkylated bipyridine platinum and palladium complexes into liposomes: stability and structure–incorporation relationships", *Biochimica et Biophysica Acta*, 1992, 1127:41–48.

Hug et al., "Liposomes for the transformation of eukaryotic cells", *Biochimica et Biophysica Acta*, 1991, 1097:1–17.

Kawai et al., "New Procedure for DNA Transfection with Polycation and Dimethyl Sulfoxide", *Molecular and Cellular Biology*, 1984, 4:1172'4 1174.

Kuo et al., "Metallocene Antitumor Agents. Solution and Solid–State Molybdenocene Coordination Chemistry of DNA Constituents, *J. Am Chem. Soc.*, 1991, 113:9027–9045.

*Mammalian Cell Biotechnology: A Practical Approach*, M. Butler, 1991 (Oxford University Press, New York), pp. 57–70.

Marsh, Derek, *CRC Handbook of Lipid Bilayers* (CRC Press, Boca Raton, FL 1990) pp. 139–141.

Mathiowitz et al., "Photochemical Rupture of Microcapsules: A Model System", *Journal of Applied Polymer Science*, 1981, 26:809–822.

Mathiowitz et al., "Polyanhydride Microspheres as Drug Carriers", *Journal of Applied Polymer Science*, 1988, 35:755–774.

May et al., "Cationic Liposomes Enable Bovine Herpesvirus Type 2 DNA to Infect Cells", *Acta virol.*, 1991, 35:107.

Mayhew et al., *Biochimica et Biophysica Acta*, 1984, 775:169–174.

Chiellini et al., *Polymers in Medicine II Biomedical and Pharmaceutical Applications*, (Plenum Press, New York and London) pp. 387–396.

Poznansky et al., "Biological Approaches to the Controlled Delivery of Drugs: A Critical Review", *Pharmacol. Rev.*, 1984, 36:277–336.

Sankaram et al., "Cholesterol–induced fluid–phase immiscibility in membranes", *Proc. Natl. Acad. Sci.*, 1991, 88:8686–8690.

Simons et al., "Antisense c–myb oligonucleotides inhibit intimal arterial smooth muscle cell accumulation in vivo", Nature, 1992, 359:67–70. ed Szoka and Papahadjopoulos, "Procedure for preparation of liposomes with large internal aqueous space and high capture by reverse–phase evaporation", *Proc. Natl. Acad. Sci.* 1978, 75:4194–4198.

Thompson, Larry, "At Age 2, Gene Therapy Enters a Growth Phase", *Science* 1992, 258:744–746.

Trubetskoy et al. "Cationic liposomes enhance targeted delivery and expression of exogenous DNA mediated by N–terminal modified poly(L–lysine) –antibody conjugate in mouse lung endothelial cells", *Biochimica et Biophysica Acta* 1992, 131:311–313.

Umemura et al., "Studies on Sonodynamic Cancer Therapy", *IEEE*, 1992, 0–7803–0785, pp. 354–355.

Williams, "Human Gene Therapy: Searching for Better Vectors", *ASM News [American Society for Microbology]* 1992, 58:67–69.

Woodle et al., "Versatility in lipid compositions showing prolonged circulation with sterically stablized liposomes", *Biochimica et Biophysica Acta* 1992, 1105:193–200.

Sato et al., "Recent Aspects in the Use of Liposomes in Biotechnology and Medicine", *Prog. Lipid Res.* 1992, 4:345–372.

Zhou et al., "Targeted delivery of DNA by liposomes and polymers", *J. of Controlled Release* 1992, 19:269–274.

Cheng et al, "The Production and Evaluation of Contrast–Carrying Liposomes Made with an Automatic High–Pressure System", Investigative Radiology 1987, 22:47–55.

Crowe et al., "Preservation of Freeze–Dried Liposomes by Trehalose", *Archives of Biochemistry and Biophysics* 1985, 242:240–247.

*Dorland's Illustrated Medical Dictionary*, 27th ed. (W.B. Saunders Company, Philadelphia 1988) p. 946.

Fukuda et al., "Polymer–Encased Vesicles Derived from Dioctadecyldimethylammonium Methacrylate", *J. Am. Chem. Soc.*, 1986, 108:2321–2327.

Hope et al., "Production of large unilamellar vesicles by a rapid extrusion procedure. Characterization of size distribution, trapped volume and ability to maintain a membrane potential", *Biochimica et Biophysica Acta*, 1985, 812:55–65.

*Liposome Technology*, Gregoriadis, ed., vol. I, pp. 1–18, 29–35, 51–65, 79–107 (CRC Press, Boca Raton, FL 1984).

McAvoy et al., "Ulrasonics symposium Proceedings", *IEEE Engineering*, vol. 2, pp. 677–1248 (abstract).

Madden et al., "The accumulation of drugs within large unilamellar vesicles exhibiting a proton gradient: a survey", *Chemistry and Physics of Lipids* 1990, 53:37–46.

Mayer et al., "Vesicles of variable sizes produced by a rapid extrusion procedure", *Biochimica et Biophysica Acta* 1986, 858:161–168.

Mayhew et al., "High–Pressure Continuous–flow System for Drug Entrapment in Liposomes", *Methods in Enzymology* 1987, 149:64–77.

Regen et al., *J. Am. Chem. Soc.* 1989, 102:6638–6640.

Shiina et al., "Hyperthermiably Low–frequency Synthesized Ultrasound", *IEEE Engineering*, vol. 2, pp. 879–880 (abstract).

Sinkula et al., "Rationale for Design of Biologically Reversible Drug Derivatives: Prodrugs", *J. Pharm. Sci.* 1975, 64:181–210.

THERAPEUTIC DRUG DELIVERY SYSTEMS

RELATED APPLICATIONS

This application is a continuation-in-part of applications U.S. Ser. Nos. 716,899, now abandoned and 717,084, now U.S. Pat. No. 5,228,446 each filed Jun. 18, 1991, which in turn are continuation-in-parts of U.S. Serial No. 569,828, filed Aug. 20, 1990, now U.S. Pat. No. 5,888,099 which in turn is a continuation-in-part of application U.S. Ser. No. 455,707, filed Dec. 22, 1989, now abandoned the disclosures of each of which are hereby incorporated herein by reference in their entirety.

BACKGROUND OF THE INVENTION

1. Field of the Invention

This invention relates to the field of therapeutic drug delivery and more specifically, to gas-filled microspheres comprising a therapeutic compound. The invention further relates to methods for employing such microspheres as therapeutic drug delivery systems.

2. Background of the Invention

Targeted drug delivery means are particularly important where the toxicity of the drug is an issue. Specific drug delivery methods potentially serve to minimize toxic side effects, lower the required dosage amounts, and decrease costs for the patient. The present invention is directed to addressing these and/or other important needs in the area of drug delivery.

The methods and materials in the prior art for introduction of genetic materials to, for example, living cells is limited and ineffective. To date several different mechanisms have been developed to deliver genetic material to living cells. These mechanisms include techniques such as calcium phosphate precipitation and electroporation, and carriers such as cationic polymers and aqueous-filled liposomes. These methods have all been relatively ineffective in vivo and only of limited use for cell culture transfection. None of these methods potentiate local release, delivery and integration of genetic material to the target cell.

Better means of delivery for therapeutics such as genetic materials are needed to treat a wide variety of human and animal diseases. Great strides have been made in characterizing genetic diseases and in understanding protein transcription but relatively little progress has been made in delivering genetic material to cells for treatment of human and animal disease.

A principal difficulty has been to deliver the genetic material from the extracellular space to the intracellular space or even to effectively localize genetic material at the surface of selected cell membranes. A variety of techniques have been tried in vivo but without great success. For example, viruses such as adenoviruses and retroviruses have been used as vectors to transfer genetic material to cells. Whole virus has been used but the amount of genetic material that can be placed inside of the viral capsule is limited and there is concern about possible dangerous interactions that might be caused by live virus. The essential components of the viral capsule may be isolated and used to carry genetic material to selected cells. In vivo, however, not only must the delivery vehicle recognize certain cells but it also must be delivered to these cells. Despite extensive work on viral vectors, it has been difficult to develop a successfully targeted viral mediated vector for delivery of genetic material in vivo.

Conventional, liquid-containing liposomes have been used to deliver genetic material to cells in cell culture but have generally been ineffective in vivo for cellular delivery of genetic material. For example, cationic liposome transfection techniques have not worked effectively in vivo. More effective means are needed to improve the cellular delivery of therapeutics such as genetic material.

SUMMARY OF THE INVENTION

The present invention provides therapeutic drug delivery systems for site-specific delivery of therapeutics using gas-filled microspheres. Once the microspheres have been introduced into the patient's body, a therapeutic compound may be targeted to specific tissues through the use of sonic energy, which is directed to the target area and causes the microspheres to rupture and release the therapeutic compound.

Specifically, the present invention provides targeted therapeutic drug delivery systems comprising a gas-filled microsphere comprising a therapeutic compound.

The invention also contemplates methods for the controlled delivery of therapeutic compounds to a region of a patient comprising: (i) administering to the patient gas-filled microspheres comprising a therapeutic compound; (ii) monitoring the microspheres using ultrasound to determine the presence of the microspheres in the region; and (iii) rupturing the microspheres using ultrasound to release the therapeutic compound in the region.

In addition, the present invention provides methods and apparatus for preparing gas-filled liposomes suitable for use as drug delivery agents. Preferred methods of the present invention provide the advantages, for example, of simplicity and potential cost savings during manufacturing of gas-filled microspheres comprising therapeutic compounds.

The gas-filled liposomes are particularly useful as drug carriers. Unlike liposomes of the prior art that have a liquid interior suitable only for encapsulating drugs that are water soluble, the gas-filled liposomes made according to the present invention are particularly useful for encapsulating lipophilic drugs. Furthermore, lipophilic derivatives of drugs may be incorporated into the lipid layer readily, such as alkylated derivatives of metallocene dihalides. Kuo et al., *J. Am. Chem. Soc.* 1991 113, 9027–9045.

It is believed that one of the advantages of the present invention includes the capture of ultrasonic energy by the gas in the microspheres which, upon rupture, create local increase in membrane fluidity, thereby enhancing cellular uptake of the therapeutic compound.

These and other features of the invention and the advantages thereof will be set forth in greater detail in the figures and the description below.

BRIEF DESCRIPTION OF THE DRAWINGS

FIG. 1B shows the subsequent release of the therapeutic upon the application of ultrasound.

FIGS. 7B and 7D show the subsequent release of the therapeutic upon the application of ultrasound.

DETAILED DESCRIPTION OF THE INVENTION

Figure 1A:
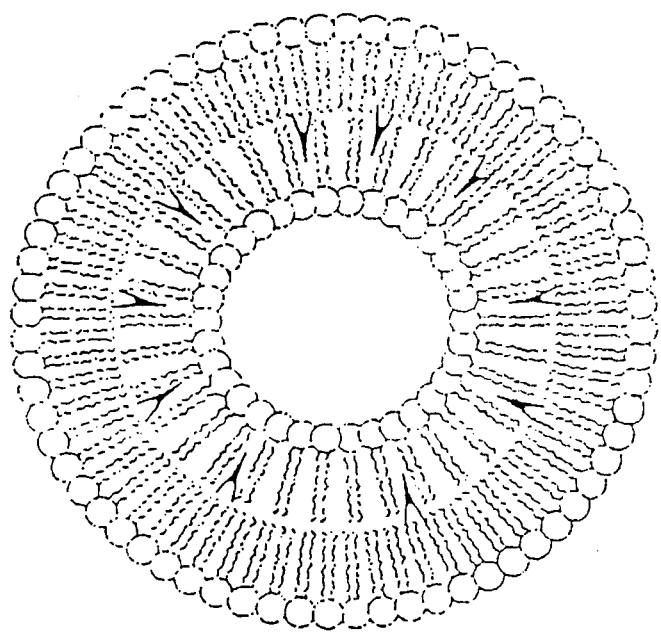
FIGS. 1A and 1B are diagrammatical representations of two liposomes. The liposome of FIG. 1A is a gas-filled liposome having a therapeutic membrane embedded hydrophobic drug compound, indicated by the blackened arrow heads, embedded within the wall of a liposome microsphere, and the liposome

The present invention provides a targeted therapeutic drug delivery system comprising a gas-filled microsphere comprising a therapeutic compound. A microsphere is defined as a structure having a relatively spherical shape with an internal void. The therapeutic compound may be embedded within the wall of the microsphere, encapsulated in the microsphere and/or attached to the microsphere, as desired. The phrase "attached to" or variations thereof, as used herein in connection with the location of the therapeutic compound, means that the therapeutic compound is linked in some manner to the inside and/or the outside wall of the microsphere, such as through a covalent or ionic bond, or other means of chemical or electrochemical linkage or interaction, as shown, for example, in FIGS. 5A, 5B, 6A, 6B, 7A, and 7B. The phrase "encapsulated in" or variations thereof as used in connection with the location of the therapeutic compound denotes that the therapeutic compound is located in the internal microsphere void, as shown, for example, in FIGS. 8A and 8B. The phrase "embedded within" or variations thereof as used in connection with the location of the therapeutic compound, signifies the positioning of the therapeutic compound within the microsphere wall, as shown, for example in FIGS. 1A, 1B, 2A, 2B, 3A, 3B, 4A, and 4B. The phrase "comprising a therapeutic" denotes all of the varying types of therapeutic positioning in connection with the microsphere. Thus, the therapeutic can be positioned variably, such as, for example, entrapped within the internal void of the gas-filled microsphere, situated between the gas and the internal wall of the gas-filled microsphere, incorporated onto the external surface of the gas-filled microsphere and/or enmeshed within the microsphere structure itself. It will also be understood by one skilled in the art, once armed with the present disclosure, that the walls of the microsphere, when it comprises a lipid, may have more than one lipid bilayer.

The microspheres of the present invention may be used for targeted therapeutic delivery either in vivo or in vitro.

Preferably, each individual microsphere is capable of releasing substantially all of the therapeutic compound upon the application of ultrasound. The phrase "substantially all" refers to at least about 80%, and preferably at least about 90%, and most preferably, about 100%. In certain embodiments, the release of all of the therapeutic compound from all of the microspheres is immediate; in other embodiments, the release is gradual. It will be understood by one skilled in the art, once armed with the present disclosure, that the preferred rate of release will vary depending upon the type of therapeutic application. In certain preferred embodiments, the therapeutic compound is encapsulated in the microspheres, for example, and thus substantially all of the therapeutic compound is immediately released from the microsphere upon rupture. Further, it will be understood by one skilled in the art, once armed with the present disclosure, that the frequency and duration of ultrasound applied can be varied to achieve a desired rate of release of the therapeutic compound.

Thus, as noted above, the therapeutic to be delivered may be encapsulated within the gas-containing microsphere, such as with a variety of therapeutics, incorporated onto the surface of the gas-containing microsphere, such as by coating a cationic lipid with negatively charged DNA or an anionic lipid with a positively charged drug, and/or embedded within the walls of the gas-containing microsphere, such as with lipophilic therapeutics. The microspheres may be prepared as microspheres comprising a therapeutic, or the microspheres may be prepared without the therapeutic and the therapeutic added to the gas-filled microspheres prior to use. In the latter case, for example, a therapeutic could be added to the gas-filled microspheres in aqueous media and shaken in order to coat the microspheres with the therapeutic.

By "gas-filled", as used herein, it is meant microspheres having an interior volume that is at least about 10% gas, preferably at least about 25% gas, more preferably at least about 50% gas, even more preferably at least about 75% gas, and most preferably at least about 90% gas. It will be understood by one skilled in the art, once armed with the present disclosure, that a gaseous precursor may also be used, followed by activation to form a gas.

Various biocompatible gases may be employed in the gas-filled microspheres of the present invention. Such gases include air, nitrogen, carbon dioxide, oxygen, argon, fluorine, xenon, neon, helium, or any and all combinations thereof. Other suitable gases will be apparent to those skilled in the art once armed with the present disclosure.

The microspheres of the present invention are preferably comprised of an impermeable material. An impermeable material is defined as a material that does not permit the passage of a substantial amount of the contents of the microsphere in typical storage conditions or in use before ultrasound induced release occurs. Typical storage conditions are, for example, a non-degassed aqueous solution of 0.9% NaCl maintained at 4° C. for 48 hours. Substantial as used in connection with impermeability is defined as greater than about 50% of the contents, the contents being both the gas and the therapeutic. Preferably, no more than about 25% of the gas and the therapeutic are released, more preferably, no more than about 10% of the gas and the therapeutic are released during storage, and most preferably no more than about 1% of the gas and therapeutic are released. The temperature of storage is preferably below the phase transition temperature of the material forming the microspheres.

At least in part, the gas impermeability of gas-filled liposomes has been found to be related to the gel state to liquid crystalline state phase transition temperature. By "gel state to liquid crystalline state phase transition temperature", it is meant the temperature at which a lipid bilayer will convert from a gel state to a liquid crystalline state. See, for example, Chapman et al., *J. Biol. Chem.* 1974 249, 2512–2521. It is believed that, generally, the higher gel state to liquid crystalline state phase transition temperature, the more gas impermeable the liposomes are at a given temperature. See Table I below and Derek Marsh, *CRC Handbook of Lipid Bilayers* (CRC Press, Boca Raton, Fla. 1990), at p. 139 for main chain melting transitions of saturated diacyl-sn-glycero-3-phosphocholines. However, it should also be noted that a lesser degree of energy can generally be used to release a therapeutic compound from gas-filled liposomes composed of lipids with a lower gel state to liquid crystalline state phase transition temperature.

TABLE I

Saturated Diacyl-sn-Glycero-3-Phosphocholines:
Main Chain Gel State to Liquid Crystalline State
Phase Transition Temperatures

| #Carbons in Acyl Chains | Main Phase Transition Temperature (°C.) |
| --- | --- |
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

The gel state to liquid crystalline state phase transition temperatures of various lipids will be readily apparent to those skilled in the art and are described, for example, in Gregoriadis, ed., *Liposome Technology*, Vol. I, 1–18 (CRC Press, 1984).

In certain preferred embodiments, the phase transition temperature of the material forming the microsphere is greater than the internal body temperature of the patient to which they are administered. For example, microspheres having a phase transition temperature greater than about 37° C. are preferred for administration to humans. In general, microspheres having a phase transition temperature greater than about 20° C. are preferred.

In preferred embodiments, the microspheres of the invention are stable, stability being defined as resistance to rupture from the time of formation until the application of ultrasound. The materials, such as lipids, used to construct the microspheres may be chosen for stability. For example, gas-filled liposomes composed of DSPC (distearoylphosphatidylcholine) are more stable than gas-filled liposomes composed of DPPC (dipalmitoylphosphatidylcholine) and that these in turn are more stable than gas-filled liposomes composed of egg phosphatidylcholine (EPC). Preferably, no more than about 50% of the microspheres rupture from the time of formation until the application of ultrasound, more preferably, no more than about 25% of the microspheres rupture, even more preferably, no more than about 10% of the microspheres, and most preferably, no more than about 1% of the microspheres.

In addition, it has been found that the incorporation of at least a small amount of negatively charged lipid into any liposome membrane, although not required, is beneficial to providing liposomes that do not have a propensity to rupture by fusing together. By at least a small amount, it is meant about 1 mole percent of the total lipid. Suitable negatively charged lipids will be readily apparent to those skilled in the art, and include, for example, phosphatidylserine and fatty acids. Most preferred for ability to rupture on application of resonant frequency ultrasound, echogenicity and stability are liposomes prepared from dipalmitoylphosphatidylcholine.

Further, the microspheres of the invention are preferably sufficiently stable in the vasculature such that they withstand recirculation. The gas-filled microspheres may be coated such that uptake by the reticuloendothelial system is minimized. Useful coatings include, for example, gangliosides, glucuronate, galacturonate, guluronate, polyethyleneglycol, polypropylene glycol, polyvinylpyrrolidone, polyvinylalcohol, dextran, starch, phosphorylated and sulfonated mono, di, tri, oligo and polysaccharides and albumin. The microspheres may also be coated for purposes such as evading recognition by the immune system.

In preferred embodiments, at least about 50%, preferably, at least about 75%, more preferably at least about 90% and most preferably, about 100% of the therapeutic and gas contents of the microspheres remain with the microsphere, because of their impermeability until they reach the internal region of the patient to be targeted and ultrasound is applied.

Further, the materials used to form the microspheres should be biocompatible. Biocompatible materials are defined as non-toxic to a patient in the amounts in which they are administered, and preferably are not disease-producing, and most preferably are harmless.

The material used to form the microspheres is also preferably flexible. Flexibility, as defined in the context of gas-filled microspheres, is the ability of a structure to alter its shape, for example, in order to pass through an opening having a size smaller than the microsphere.

Liposomes are a preferred embodiment of this invention since they are highly useful for entrapping gas. Additionally, gas-filled liposomes are preferred due to their biocompatibility and the ability to easily accommodate lipophilic therapeutic compounds that will easily cross cell membranes after the liposomes are ruptured. One skilled in the art, once armed with the present disclosure, would recognize that particular lipids may be chosen for the intended use.

Provided that the circulation half-life of the microspheres is sufficiently long, the microspheres will generally pass through the target tissue as they pass through the body. By focusing the rupture inducing sound waves on the selected tissue to be treated, the therapeutic will be released locally in the target tissue. As a further aid to targeting, antibodies, carbohydrates, peptides, glycopeptides, glycolipids and lectins may also be incorporated into the surface of the microspheres.

Where lipid material is used to create the microspheres, thus forming a liposome, a wide variety of lipids may be utilized in the construction of the microspheres. The materials which may be utilized in preparing liposomes include any of the materials or combinations thereof known to those skilled in the art as suitable for liposome preparation. The lipids used may be of either natural or synthetic origin. The particular lipids are chosen to optimize the desired properties, e.g., short plasma half-life versus long plasma half-life for maximal serum stability.

The lipid in the gas-filled liposomes may be in the form of a single bilayer or a multilamellar bilayer, and are preferably multilamellar.

Lipids which may be used to create liposome microspheres include but are not limited to: lipids such as fatty acids, lysolipids, phosphatidylcholine with both saturated and unsaturated lipids including; dimyristoylphosphatidylcholine; dipentadecanoylphosphatidylcholine, dilauroylphosphatidylcholine, dioleoylphosphatidylcholine, dipalmitoylphosphatidylcholine; distearoylphosphatidylcholine; phosphatidylethanolamines such as dioleoylphosphatidylethanolamine; phosphatidylserine; phosphatidylglycerol; phosphatidylinositol, sphingolipids such as sphingomyelin; glycolipids such as ganglioside GM1 and GM2; glucolipids; sulfatides; glycosphingolipids; phosphatidic acid; palmitic acid; stearic acid; arachidonic acid; oleic acid; lipids bearing polymers such as polyethyleneglycol, chitin, hyaluronic acid or polyvinylpyrrolidone; lipids bearing sulfonated mono-, di-, oligo- or polysaccharides; cholesterol, cholesterol sulfate and cholesterol hemisuccinate; tocopherol hemisuccinate, lipids with ether and ester-linked fatty acids, polymerized lipids, diacetyl phosphate, stearylamine, cardiolipin, phospholipids with short chain fatty acids of 6–8 carbons in length, synthetic phospholipids with asymmetric acyl chains (e.g., with one acyl chain of 6 carbons and another acyl chain of 12 carbons), 6-(5-cholesten-3β-yloxy)-1-thio-β-D-galactopyranoside, digalactosyldiglyceride, 6-(5-cholesten-3β-yloxy)hexyl-6-amino-6-deoxy-1-thio-α-D-galactopyranoside, 6-(5-cholesten-3β-yloxy)hexyl-6-amino-6-deoxyl-1-thio-α-D-mannopyranoside, 12-(((7'-diethylaminocoumarin-3-yl)carbonyl)methylamino)-octadecanoic acid; N-[12-(((7'-diethylaminocoumarin-3-yl)carbonyl)methyl-amino)octadecanoyl]-2-aminopalmitic acid; cholesteryl)4'-trimethylammonio)butanoate; N-succinyldioleoylphosphatidylethanolamine; 1,2-dioleoyl-sn-glycerol;1,2-dipalmitoyl-sn-3-succinylglycerol; 1,3-dipalmitoyl-2-succinylglycerol;1-hexadecyl-2-palmitoylglycerophosphoethanolamine and palmitoylhomocysteine, and/or combinations thereof.

If desired, a variety of cationic lipids such as DOTMA, N-[1-(2,3-dioleoyloxy)propyl]-N,N,N-trimethylammoium chloride; DOTAP, 1,2-dioleoyloxy-3-(trimethylammonio)propane; and DOTB, 1,2-dioleoyl-3-(4'-trimethyl-ammonio)butanoyl-sn-glycerol may be used. In general the molar ratio of cationic lipid to non-cationic lipid in the liposome may be, for example, 1:1000, 1:100, preferably, between 2:1 to 1:10, more preferably in the range between 1:1 to 1:2.5 and most preferably 1:1 (ratio of mole amount cationic lipid to mole amount non-cationic lipid, e.g., DPPC). A wide variety of lipids may comprise the non-cationic lipid when cationic lipid is used to construct the microsphere. Preferably, this non-cationic lipid is dipalmitoylphosphatidylcholine, dipalmitoylphosphatidylethanolamine or dioleoylphosphatidylethanolamine. In lieu of cationic lipids as described above, lipids bearing cationic polymers such as polylysine or polyarginine may also be used to construct the microspheres and afford binding of a negatively charged therapeutic, such as genetic material, to the outside of the microspheres.

Other useful lipids or combinations thereof apparent to those skilled in the art which are in keeping with the spirit of the present invention are also encompassed by the present invention. For example, carbohydrate-bearing lipids may be employed for in vivo targeting, as described in U.S. Pat. No. 4,310,505, the disclosures of which are hereby incorporated herein by reference, in their entirety.

The most preferred lipids are phospholipids, preferably DPPC and DSPC, and most preferably DPPC.

Saturated and unsaturated fatty acids that may be used to generate gas-filled microspheres preferably include, but are not limited to molecules that have between 12 carbon atoms and 22 carbon atoms in either linear or branched form. Examples of saturated fatty acids that may be used include, but are not limited to, lauric, myristic, palmitic, and stearic acids. Examples of unsaturated fatty acids that may be used include, but are not limited to, lauroleic, physeteric, myristoleic, palmitoleic, petroselinic, and oleic acids. Examples of branched fatty acids that may be used include, but are not limited to, isolauric, isomyristic, isopalmitic, and isostearic acids and isoprenoids.

Solutions of lipids or gas-filled liposomes may be stabilized, for example, by the addition of a wide variety of viscosity modifiers, including, but not limited to carbohydrates and their phosphorylated and sulfonated derivatives; polyethers, preferably with molecular weight ranges between 400 and 8000; di- and trihydroxy alkanes and their polymers, preferably with molecular weight ranges between 800 and 8000. Emulsifying and/or solubilizing agents may also be used in conjunction with lipids or liposomes. Such agents include, but are not limited to, acacia, cholesterol, diethanolamine, glyceryl monostearate, lanolin alcohols, lecithin, nono- and di-glycerides, mono-ethanolamine, oleic acid, oleyl alcohol, poloxamer, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmirate, sorbitan monostearate, stearic acid, trolamine, and emulsifying wax. Suspending and/or viscosity-increasing agents that may be used with lipid or liposome solutions include, but are not limited to, acacia, agar, alginic acid, aluminum monostearate, bentonite, magma, carbomer 934P, carboxymethylcellulose, calcium and sodium and sodium 12, carrageenan, cellulose, dextrin, gelatin, guar gum, hydroxyethyl cellulose, hydroxypropyl methylcellulose, magnesium aluminum silicate, methylcellulose, pectin, polyethylene oxide, polyvinyl alcohol, povidone, propylene glycol alginate, silicon dioxide, sodium alginate, tragacanth, and xanthum gum.

Any of a variety of therapeutics may be encapsulated in the microspheres. By therapeutic, as used herein, it is meant an agent having a beneficial effect on the patient. As used herein, the term therapeutic is synonymous with the term drug.

Suitable therapeutics include, but are not limited to: antineoplastic agents, such as platinum compounds (e.g., spiroplatin, cisplatin, and carboplatin), methotrexate, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, taxol, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) *Erwina asparaginase*, etoposide (VP-16), interferon α-2a, interferon α-2b, teniposide (VM-26), vinblastine sulfate (VLB), vincristine sulfate, bleomycin, bleomycin sulfate, methotrexate, adriamycin, and arabinosyl; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine; anti-fungal agents such as ketoconazole, nystatin, griseofulvin, flucytosine (5-fc), miconazole, amphotericin B, ricin, and β-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide and fludrocortisone acetate; vitamins such as cyanocobalamin neinoic acid, retinoids and derivatives such as retinol palmitate, and α-tocopherol; peptides, such as manganese super oxide dismutase; enzymes such as alkaline phosphatase; anti-allergic agents such as amelexanox; anti-coagulation agents such as phenprocoumon and heparin; circulatory drugs such as propranolol; metabolic potentiators such as glutathione; antitubercular such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT or Zidovudine), ribavirin and vidarabine monohydrate (adenine arabinoside, ara-A); antianginals such as diltiazem, nifedipine, verapamil, erythritol tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; antiinflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium mesylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium and yttrium.

In certain preferred embodiments, the therapeutic is a monoclonal antibody, such as a monoclonal antibody capable of binding to melanoma antigen.

Other preferred therapeutics include genetic material such as nucleic acids, RNA, and DNA, of either natural or synthetic origin, including recombinant RNA and DNA and antisense RNA and DNA. Types of genetic material that may be used include, for example, genes carried on expression vectors such as plasmids, phagemids, cosmids, yeast artificial chromosomes (YACs), and defective or "helper" viruses, antigene nucleic acids, both single and double stranded RNA and DNA and analogs thereof, such as phosphorothioate and phosphorodithioate oligodeoxynucleotides. Additionally, the genetic material may be combined, for example, with proteins or other polymers.

Examples of genetic therapeutics that may be applied using the microspheres of the present invention include DNA encoding at least a portion of an HLA gene, DNA encoding at least a portion of dystrophin, DNA encoding at least a portion of CFTR, DNA encoding at least a portion of IL-2, DNA encoding at least a portion of TNF, an antisense oligonucleotide capable of binding the DNA encoding at least a portion of Ras.

DNA encoding certain proteins may be used in the treatment of many different types of diseases. For example, adenosine deaminase may be provided to treat ADA deficiency; tumor necrosis factor and/or interleukin-2 may be provided to treat advanced cancers; HDL receptor may be provided to treat liver disease; thymidine kinase may be provided to treat ovarian cancer, brain tumors, or HIV infection; HLA-B7 may be provided to treat malignant melanoma; interleukin-2 may be provided to treat neuroblastoma, malignant melanoma, or kidney cancer; interleukin-4 may be provided to treat cancer; HIV env may be provided to treat HIV infection; antisense ras/p53 may be provided to treat lung cancer; and Factor VIII may be provided to treat Hemophilia B. See, for example, *Science* 258, 744–746.

If desired, more than one therapeutic may be applied using the microspheres. For example, a single microsphere may contain more than one therapeutic or microspheres containing different therapeutics may be co-administered. By way of example, a monoclonal antibody capable of binding to melanoma antigen and an oligonucleotide encoding at least a portion of IL-2 may be administered at the same time. The phrase "at least a portion of," as used herein, means that the entire gene need not be represented by the oligonucleotide, so long as the portion of the gene represented provides an effective block to gene expression.

Similarly, prodrugs may be encapsulated in the microspheres, and are included within the ambit of the term therapeutic, as used herein. Prodrugs are well known in the art and include inactive drug precursors which, when exposed to high temperature, metabolizing enzymes, cavitation and/or pressure, in the presence of oxygen or otherwise, or when released from the microspheres, will form active drugs. Such prodrugs can be activated in the method of the invention, upon the application of ultrasound to the prodrug-containing microspheres with the resultant cavitation, heating, pressure, and/or release from the microspheres. Suitable prodrugs will be apparent to those skilled in the art, and are described, for example, in Sinkula et al., *J. Pharm. Sci.* 1975 64, 181–210, the disclosure of which are hereby incorporated herein by reference in its entirety.

Prodrugs, for example, may comprise inactive forms of the active drugs wherein a chemical group is present on the prodrug which renders it inactive and/or confers solubility or some other property to the drug. In this form, the prodrugs are generally inactive, but once the chemical group has been cleaved from the prodrug, by heat, cavitation, pressure, and/or by enzymes in the surrounding environment or otherwise, the active drug is generated. Such prodrugs are well described in the art, and comprise a wide variety of drugs bound to chemical groups through bonds such as esters to short, medium or long chain aliphatic carbonates, hemiesters of organic phosphate, pyrophosphate, sulfate, amides, amino acids, azo bonds, carbamate, phosphamide, glucosiduronate, N-acetylglucosamine and β-glucoside.

Examples of drugs with the parent molecule and the reversible modification or linkage are as follows: convallatoxin with ketals, hydantoin with alkyl esters, chlorphenesin with glycine or alanine esters, acetaminophen with caffeine complex, acetylsalicylic acid with THAM salt, acetylsalicylic acid with acetamidophenyl ester, naloxone with sulfate ester, 15-methylprostaglandin $F_{2\alpha}$ with methyl ester, procaine with polyethylene glycol, erythromycin with alkyl esters, clindamycin with alkyl esters or phosphate esters, tetracycline with betaine salts, 7-acylaminocephalosporins with ring-substituted acyloxybenzyl esters, nandrolone with phenylproprionate decanoate esters, estradiol with enol ether acetal, methylprednisolone with acetate esters, testosterone with n-acetylglucosaminide glucosiduronate (trimethylsilyl) ether, cortisol or prednisolone or dexamethasone with 21-phosphate esters.

Prodrugs may also be designed as reversible drug derivatives and utilized as modifiers to enhance drug transport to site-specific tissues. Examples of parent molecules with reversible modifications or linkages to influence transport to a site specific tissue and for enhanced therapeutic effect include isocyanate with haloalkyl nitrosurea, testosterone with propionate ester, methotrexate (3-5'-dichloromethotrexate) with dialkyl esters, cytosine arabinoside with 5'-acylate, nitrogen mustard (2,2'-dichloro-N-methyldiethylamine), nitrogen mustard with aminomethyl tetracycline, nitrogen mustard with cholesterol or estradiol or dehydroepiandrosterone esters and nitrogen mustard with azobenzene.

As one skilled in the art would recognize, a particular chemical group to modify a given drug may be selected to influence the partitioning of the drug into either the membrane or the internal space of the microspheres. The bond selected to link the chemical group to the drug may be selected to have the desired rate of metabolism, e.g., hydrolysis in the case of ester bonds in the presence of serum esterases after release from the gas-filled microspheres. Additionally, the particular chemical group may be selected to influence the biodistribution of the drug employed in the gas-filled drug carrying microsphere invention, e.g., N,N-bis(2-chloroethyl)-phosphorodiamidic acid with cyclic phosphoramide for ovarian adenocarcinoma.

Additionally, the prodrugs employed within the gas-filled microspheres may be designed to contain reversible derivatives which are utilized as modifiers of duration of activity to provide, prolong or depot action effects. For example, nicotinic acid may be modified with dextran and carboxymethyldextran esters, streptomycin with alginic acid salt, dihydrostreptomycin with pamoate salt, cytarabine (ara-C) with 5'-adamantoate ester, ara-adenosine (ara-A) with 5-palmitate and 5'-benzoate esters, amphotericin B with methyl esters, testosterone with 17-β-alkyl esters, estradiol with formate ester, prostaglandin with 2-(4-imidazolyl)ethylamine salt, dopamine with amino acid amides, chloramphenicol with mono- and bis(trimethylsilyl) ethers, and cycloguanil with pamoate salt. In this form, a depot or reservoir of long-acting drug may be released in vivo from the gas-filled prodrug bearing microspheres.

In addition, compounds which are generally thermally labile may be utilized to create toxic free radical compounds. Compounds with azolinkages, peroxides and disulfide linkages which decompose with high temperature are preferred. With this form of prodrug, azo, peroxide or disulfide bond containing compounds are activated by cavitation and/or increased heating caused by the interaction of high energy sound with the gas-filled microspheres to create cascades of free radicals from these prodrugs entrapped therein. A wide variety of drugs or chemicals may constitute these prodrugs, such as azo compounds, the general structure of such compounds being R—N=N—R, wherein R is a hydrocarbon chain, where the double bond between the two nitrogen atoms may react to create free radical products in vivo.

Exemplary drugs or compounds which may be used to create free radical products include azo containing compounds such as azobenzene, 2,2'-azobisisobutyronitrile, azodicarbonamide, azolitmin, azomycin, azosemide, azosulfamide, azoxybenzene, aztreonam, sudan III, sulfachrysoidine, sulfamidochrysoidine and sulfasalazine, compounds containing disulfide bonds such as sulbentine, thiamine disulfide, thiolutin, thiram, compounds containing peroxides such as hydrogen peroxide and benzoylperoxide, 2,2'-azobisisobutyronitrile, 2,2'-azobis(2-amidopropane) dihydrochloride, and 2,2'-azobis(2,4-dimethylvaleronitrile).

A gas-filled microsphere filled with oxygen gas should create extensive free radicals with cavitation. Also, metal ions from the transition series, especially manganese, iron and copper can increase the rate of formation of reactive oxygen intermediates from oxygen. By encapsulating metal ions within the microspheres, the formation of free radicals in vivo can be increased. These metal ions may be incorporated into the microspheres as free salts, as complexes, e.g., with EDTA, DTPA, DOTA or desferrioxamine, or as oxides of the metal ions. Additionally, derivatized complexes of the metal ions may be bound to lipid head groups, or lipophilic complexes of the ions may be incorporated into a lipid bilayer, for example. When exposed to thermal stimulation, e.g., cavitation, these metal ions then will increase the rate of formation of reactive oxygen intermediates. Further, radiosensitizers such as metronidazole and misonidazole may be incorporated into the gas-filled microspheres to create free radicals on thermal stimulation.

By way of an example of the use of prodrugs, an acylated chemical group may be bound to a drug via an ester linkage which would readily cleave in vivo by enzymatic action in serum. The acylated prodrug is incorporated into the gas-filled microsphere of the invention. When the gas-filled microsphere is popped by the sonic pulse from the ultrasound, the prodrug encapsulated by the microsphere will then be exposed to the serum. The ester linkage is then cleaved by esterases in the serum, thereby generating the drug.

Similarly, ultrasound may be utilized not only to rupture the gas-filled microsphere, but also to cause thermal effects which may increase the rate of the chemical cleavage and the release of the active drug from the prodrug.

The microspheres may also be designed so that there is a symmetric or an asymmetric distribution of the drug both inside and outside of the microsphere.

The particular chemical structure of the therapeutics may be selected or modified to achieve desired solubility such that the therapeutic may either be encapsulated within the internal gas-filled space of the microsphere, attached to the microsphere or enmeshed in the microsphere. The surface-bound therapeutic may bear one or more acyl chains such that, when the microsphere is popped or heated or ruptured via cavitation, the acylated therapeutic may then leave the surface and/or the therapeutic may be cleaved from the acyl chains chemical group. Similarly, other therapeutics may be formulated with a hydrophobic group which is aromatic or sterol in structure to incorporate into the microsphere surface.

In addition to lipids, other materials that may be used to form the microspheres include, for example, proteins such as albumin, synthetic peptides such as polyglutamic acid, and linear and branched oligomers and polymers of galactose, glucose and other hexosaccharides and polymers derived from phosphorylated and sulfonated pentose and hexose sugars and sugar alcohols. Carbohydrate polymers such as alginic acid, dextran, starch and HETA starch may also be used. Other natural polymers, such as hyaluronic acid, may be utilized. Synthetic polymers such as polyethyleneglycol, polyvinylpyrrolidone, polylactide, polyethyleneimines (linear and branched), polyionenes or polyiminocarboxylates may also be employed.

Where the therapeutic encapsulated by the microspheres is negatively charged, such as genetic material, cationic lipids or perfluoroalkylated groups bearing cationic groups may be utilized to bind the negatively charged therapeutic. For example, cationic analogs of amphiphilic perfluoroalkylated bipyridines, as described in Garelli and Vierling, *Biochim. Biophys Acta,* 1992 1127, 41–48, the disclosures of which are hereby incorporated herein by reference in their entirety, may be used.

In general, negatively charged therapeutics such as genetic material may be bound to the hydrophilic headgroups of mixed micellar components, e.g., non-cationic lipid with cationic lipids, for example, DOTMA or stearylamine or substituted alkyl groups such as trimethylstearylamine. Useful mixed micellar compounds include but are not limited to: lauryltrimethylammonium bromide (dodecyl), cetyltrimethylammonium bromide (hexadecyl-), myristyltrimethylammonium bromide (tetradecyl-), alkyldimethylbenzylammonium chloride (alkyl=$C_{12}$, $C_{14}$, $C_{16'}$), benzyldimethyldodecylammonium bromide/chloride, benzyldimethylhexadecylammonium bromide/chloride, benzyldimethyltetradecylammonium bromide/chloride, cetyldimethylethylammonium bromide/chloride, or cetylpyridinium bromide/chloride.

The size of drug containing liposomes can be adjusted, if desired, by a variety of procedures including extrusion, filtration, sonication, homogenization, employing a laminar stream of a core of liquid introduced into an immiscible sheath of liquid, extrusion under pressure through pores of defined size, and similar methods, in order to modulate resultant liposomal biodistribution and clearance. The foregoing techniques, as well as others, are discussed, for example, in U.S. Pat. No. 4,728,578; U.K. Patent Application GB 2193095 A; U.S. Pat. No. 4,728,575; U.S. Pat. No. 4,737,323; International Application PCT/US85/01161; Mayer et al., *Biochimica et Biophysica Acta,* Vol. 858, pp. 161–168 (1986); Hope et al., *Biochimica et Biophysica Acta,* Vol. 812, pp. 55–65 (1985); U.S. Pat. No. 4,533,254; Mayhew et al., *Methods in Enzymology,* Vol. 149, pp. 64–77 (1987); Mayhew et al., *Biochimica et Biophysica Acta,* Vol 755, pp. 169–74 (1984); Cheng et al, *Investigative Radiology,* Vol. 22, pp. 47–55 (1987); PCT/US89/05040, U.S. Pat. Nos. 4,162,282; 4,310,505; 4,921,706; and *Liposome Tech-*

*nology*, Gregoriadis, G., ed., Vol. I, pp. 29–31, 51–67 and 79–108 (CRC Press Inc., Boca Raton, Fla. 1984). The disclosures of each of the foregoing patents, publications and patent applications are incorporated by reference herein, in their entirety.

The size of the microspheres of the present invention will depend upon the intended use. Since microsphere size influences biodistribution, different size microspheres may be selected for various purposes. With the smaller microspheres, resonant frequency ultrasound will generally be higher than for the larger microspheres.

For example, for intravascular application, the preferred size range is a mean outside diameter between about 30 nanometers and about 10 microns, with the preferable mean outside diameter being about 5 microns. More specifically, for intravascular application, the size of the microspheres is preferably about 10 μm or less in mean outside diameter, and preferably less than about 7 μm, and more preferably less than about 5 μm. Preferably, the microspheres are no smaller than about 30 nanometers in mean outside diameter.

To provide therapeutic delivery to organs such as the liver and to allow differentiation of tumor from normal tissue, smaller microspheres, between about 30 nanometers and about 100 nanometers in mean outside diameter, are preferred.

For embolization of a tissue such as the kidney or the lung, the microspheres are preferably less than about 200 microns in mean outside diameter.

For intranasal, intrarectal or topical administration, the microspheres are preferably less than about 100 microns in mean outside diameter.

Large microspheres, e.g., between 1 and 10 microns in size, will generally be confined to the intravascular space until they are cleared by phagocytic elements lining the vessels, such as the macrophages and Kuppfer cells lining capillary sinusoids. For passage to the cells beyond the sinusoids, smaller microspheres, for example, less than about a micron in diameter, e.g., less than about 300 nanometers in size, may be utilized.

In preferred embodiments, the microspheres are administered individually, rather than, for example, embedded in a matrix.

Generally, the therapeutic delivery systems of the invention are administered in the form of an aqueous suspension such as in water or a saline solution (e.g., phosphate buffered saline). Preferably, the water is sterile. Also, preferably the saline solution is an isotonic saline solution, although, if desired, the saline solution may be hypotonic (e.g., about 0.3 to about 0.5% NaCl). The solution may also be buffered, if desired, to provide a pH range of about pH 5 to about pH 7.4. In addition, dextrose may be preferably included in the media. Further solutions that may be used for administration of gas-filled liposomes include, but are not limited to, almond oil, corn oil, cottonseed oil, ethyl oleate, isopropyl myristate, isopropyl palmitate, mineral oil, myristyl alcohol, octyl-dodecanol, olive oil, peanut oil, persic oil, sesame oil, soybean oil, and squalene.

For storage prior to use, the microspheres of the present invention may be suspended in an aqueous solution, such as a saline solution (for example, a phosphate buffered saline solution), or simply water, and stored preferably at a temperature of between about 2° C. and about 10° C., preferably at about 4° C. Preferably, the water is sterile. Most preferably, the microspheres are stored in an isotonic saline solution, although, if desired, the saline solution may be a hypotonic saline solution (e.g., about 0.3 to about 0.5% NaCl). The solution also may be buffered, if desired, to provide a pH range of about pH 5 to about pH 7.4. Suitable buffers for use in the storage media include, but are not limited to, acetate, citrate, phosphate and bicarbonate.

Bacteriostatic agents may also be included with the microspheres to prevent bacterial degradation on storage. Suitable bacteriostatic agents include but are not limited to benzalkonium chloride, benzethonium chloride, benzoic acid, benzyl alcohol, butylparaben, cetylpyridinium chloride, chlorobutanol, chlorocresol, methylparaben, phenol, potassium benzoate, potassium sorbate, sodium benzoate and sorbic acid. One or more antioxidants may further be included with the gas-filled liposomes to prevent oxidation of the lipid. Suitable antioxidants include tocopherol, ascorbic acid and ascorbyl palmitate.

Methods of controlled delivery of therapeutic compounds to a region of a patient involve the steps of:
  (i) administering to the patient gas-filled microspheres comprising a therapeutic compound;
  (ii) monitoring the microspheres using ultrasound to determine the presence of the microspheres in the region; and
  (iii) rupturing the microspheres using ultrasound to release the therapeutic compound in the region.

Using the gas-filled microspheres of the present invention, ultrasonic energy interacts with the gas, bursting the microspheres and allowing a therapeutic such as, for example, genetic material to be released and transported into cells. When the sonic energy encounters the interface of the gas within the tissue or fluid medium, local conversion of sonic energy into thermal and kinetic energy is greatly enhanced. The therapeutic material is thereby released from the microspheres and surprisingly delivered into the cells. Although not intending to be bound by any particular theory of operation, it is believed that the thermal and kinetic energy created at the site of the cell enhances cellular uptake of the therapeutic.

The route of administration of the microspheres will vary depending on the intended use. As one skilled in the art would recognize, administration of therapeutic delivery systems of the present invention may be carried out in various fashions, such as intravascularly, intralymphatically, parenterally, subcutaneously, intramuscularly, intranasally, intrarectally, intraperitoneally, interstitially, into the airways via nebulizer, hyperbarically, orally, topically, or intratumorly, using a variety of dosage forms. One preferred route of administration is intravascularly. For intravascular use, the therapeutic delivery system is generally injected intravenously, but may be injected intraarterially as well. The microspheres of the invention may also be injected interstitially or into any body cavity.

The delivery of therapeutics from the microspheres of the present invention using ultrasound is best accomplished for tissues which have a good acoustic window for the transmission of ultrasonic energy. This is the case for most tissues in the body such as muscle, the heart, the liver and most other vital structures. In the brain, in order to direct the ultrasonic energy past the skull a surgical window may be necessary.

The useful dosage to be administered and the mode of administration will vary depending upon the age, weight, and type of animal to be treated, and the particular therapeutic application intended. Typically, dosage is initiated at lower levels and increased until the desired therapeutic effect is achieved.

For in vitro use, such as cell culture applications, the gas-filled microspheres may be added to the cells in cultures and then incubated. Sonic energy can then be applied to the culture media containing the cells and microspheres.

The present invention may be employed in the controlled delivery of therapeutics to a region of a patient wherein the patient is administered the therapeutic containing microsphere of the present invention, the microspheres are monitored using ultrasound to determine the presence of the microspheres in the region, and the microspheres are then ruptured using ultrasound to release the therapeutics in the region.

The patient may be any type of animal, but is preferably a vertebrate, more preferably a mammal, and most preferably human. By region of a patient, it is meant the whole patient, or a particular area or portion of the patient. For example, by using the method of the invention, therapeutic delivery may be effected in a patient's heart, and a patient's vasculature (that is, venous or arterial systems). The invention is also particularly useful in delivering therapeutics to a patient's left heart, a region not easily reached heretofore with therapeutic delivery. Therapeutics may also be easily delivered to the liver, spleen and kidney regions of a patient, as well as other regions, using the present methods.

Additionally, the invention is especially useful in delivering therapeutics to a patient's lungs. Gas-filled microspheres of the present invention are lighter than, for example, conventional liquid-filled liposomes which generally deposit in the central proximal airway rather than reaching the periphery of the lungs. It is therefore believed that the gas-filled microspheres of the present invention may improve delivery of a therapeutic compound to the periphery of the lungs, including the terminal airways and the alveoli. For application to the lungs, the gas-filled microspheres may be applied through nebulization, for example.

In applications such as the targeting of the lungs, which are lined with lipids, the therapeutic may be released upon aggregation of a gas-filled lipid microsphere with the lipids lining the targeted tissue. Additionally, the gas-filled lipid microspheres may burst after administration without the use of ultrasound. Thus, ultrasound need not be applied to release the drug in the above type of administration.

Further, the gas-filled microspheres of the invention are especially useful for therapeutics that may be degraded in aqueous media or upon exposure to oxygen and/or atmospheric air. For example, the microspheres may be filled with an inert gas such as nitrogen or argon, for use with labile therapeutic compounds. Additionally, the gas-filled microspheres may be filled with an inert gas and used to encapsulate a labile therapeutic for use in a region of a patient that would normally cause the therapeutic to be exposed to atmospheric air, such as cutaneous and ophthalmic applications.

The gas-filled microspheres are also especially useful for transcutaneous delivery, such as a patch delivery system. The use of rupturing ultrasound may increase transdermal delivery of therapeutic compounds. Further, a mechanism may be used to monitor and modulate drug delivery. For example, diagnostic ultrasound may be used to visually monitor the bursting of the gas-filled microspheres and modulate drug delivery and/or a hydrophone may be used to detect the sound of the bursting of the gas-filled microspheres and modulate drug delivery.

The echogenicity of the microspheres and the ability to rupture the microspheres at the peak resonant frequency using ultrasound permits the controlled delivery of therapeutics to a region of a patient by allowing the monitoring of the microspheres following administration to a patient to determine the presence of microspheres in a desired region, and the rupturing of the microspheres using ultrasound to release the therapeutics in the region.

Preferably, the microspheres of the invention possess a reflectivity of greater than 2 dB, preferably between about 4 dB and about 20 dB. Within these ranges, the highest reflectivity for the microspheres of the invention is exhibited by the larger microspheres, by higher concentrations of microspheres, and/or when higher ultrasound frequencies are employed.

Preferably, the microspheres of the invention have a peak resonant frequency of between about 0.5 mHz and about 10 mHz. Of course, the peak resonant frequency of the gas-filled microspheres of the invention will vary depending on the diameter and, to some extent, the elasticity or flexibility of the microspheres, with the larger and more elastic or flexible microspheres having a lower resonant frequency than the smaller and less elastic or flexible microspheres.

The rupturing of the therapeutic containing microspheres of the invention is surprisingly easily carried out by applying ultrasound of a certain frequency to the region of the patient where therapy is desired, after the microspheres have been administered to or have otherwise reached that region. Specifically, it has been unexpectedly found that when ultrasound is applied at a frequency corresponding to the peak resonant frequency of the therapeutic containing gas-filled microspheres, the microspheres will rupture and release their contents.

The peak resonant frequency can be determined either in vivo or in vitro, but preferably in vivo, by exposing the microspheres to ultrasound, receiving the reflected resonant frequency signals and analyzing the spectrum of signals received to determine the peak, using conventional means. The peak, as so determined, corresponds to the peak resonant frequency (or second harmonic, as it is sometimes termed).

The gas-filled microspheres will also rupture when exposed to non-peak resonant frequency ultrasound in combination with a higher intensity (wattage) and duration (time). This higher energy, however, results in greatly increased heating, which may not be desirable. By adjusting the frequency of the energy to match the peak resonant frequency, the efficiency of rupture and therapeutic release is improved, appreciable tissue heating does not generally occur (frequently no increase in temperature above about 2° C.), and less overall energy is required. Thus, application of ultrasound at the peak resonant frequency, while not required, is most preferred.

Any of the various types of diagnostic ultrasound imaging devices may be employed in the practice of the invention, the particular type or model of the device not being critical to the method of the invention. Also suitable are devices designed for administering ultrasonic hyperthermia, such devices being described in U.S. Pat. Nos. 4,620,546, 4,658,828, and 4,586,512, the disclosures of each of which are hereby incorporated herein by reference in their entirety. Preferably, the device employs a resonant frequency (RF) spectral analyzer. The transducer probes may be applied externally or may be implanted. Ultrasound is generally initiated at lower intensity and duration, preferably at peak resonant frequency, and then intensity, time, and/or resonant frequency increased until the microsphere ruptures.

Although application of the various principles will be readily apparent to one skilled in the art, once armed with the present disclosure, by way of general guidance, for gas-filled microspheres of about 1.5 to about 10 microns in mean outside diameter, the resonant frequency will generally be in the range of about 1 to about 10 megahertz. By adjusting the focal zone to the center of the target tissue (e.g., the tumor) the gas-filled microspheres can be visualized under real time ultrasound as they accumulate within the target tissue. Using the 7.5 megahertz curved array transducer as an example, adjusting the power delivered to the transducer to maximum and adjusting the focal zone within the target tissue, the spatial peak temporal average (SPTA) power will then be a maximum of approximately 5.31 mW/cm$^2$ in water. This power will cause some release of therapeutic from the gas-filled microspheres, but much greater release can be accomplished by using higher power.

By switching the transducer to the doppler mode, higher power outputs are available, up to 2.5 watts per cm$^2$ from the same transducer. With the machine operating in doppler mode, the power can be delivered to a selected focal zone within the target tissue and the gas-filled microspheres can be made to release their therapeutics. Selecting the transducer to match the resonant frequency of the gas-filled microspheres will make this process of therapeutic release even more efficient.

For larger diameter gas-filled microspheres, e.g., greater than 3 microns in mean outside diameter, a lower frequency transducer may be more effective in accomplishing therapeutic release. For example, a lower frequency transducer of 3.5 megahertz (20 mm curved array model) may be selected to correspond to the resonant frequency of the gas-filled microspheres. Using this transducer, 101.6 milliwatts per cm$^2$ may be delivered to the focal spot, and switching to doppler mode will increase the power output (SPTA) to 1.02 watts per cm$^2$.

To use the phenomenon of cavitation to release and/or activate the drugs/prodrugs within the gas-filled microspheres, lower frequency energies may be used, as cavitation occurs more effectively at lower frequencies. Using a 0.757 megahertz transducer driven with higher voltages (as high as 300 volts) cavitation of solutions of gas-filled microspheres will occur at thresholds of about 5.2 atmospheres.

Table II shows the ranges of energies transmitted to tissues from diagnostic ultrasound on commonly used instruments such as the Piconics Inc. (Tyngsboro, Md.) Portascan general purpose scanner with receiver pulser 1966 Model 661; the Picker (Cleveland, Ohio) Echoview 8L Scanner including 80C System or the Medisonics (Mountain View, Calif.) Model D-9 Versatone Bidirectional Doppler. In general, these ranges of energies employed in pulse repetition are useful for monitoring the gas-filled microspheres but are insufficient to rupture the gas-filled microspheres of the present invention.

TABLE II

Power and Intensities Produced by Diagnostic Equipment*

| Pulse repetition rate (Hz) | Total ultrasonic power output P (mW) | Average Intensity at transducer face $I_{TD}$ (W/m$^2$) |
|---|---|---|
| 520 | 4.2 | 32 |
| 676 | 9.4 | 71 |
| 806 | 6.8 | 24 |
| 1000 | 14.4 | 51 |
| 1538 | 2.4 | 8.5 |

*Values obtained from Carson et al., Ultrasound in Med. & Biol. 1978 3, 341–350, the disclosures of which are hereby incorporated by reference in their entirety.

Higher energy ultrasound such as commonly employed in therapeutic ultrasound equipment is preferred for activation of the gas-filled microspheres. In general, therapeutic ultrasound machines employ as much as 50% to 100% duty cycles dependent upon the area of tissue to be heated by ultrasound. Areas with larger amounts of muscle mass (i.e., backs, thighs) and highly vascularized tissues such as heart may require the larger duty cycle, e.g., 100%.

In diagnostic ultrasound, which may be used to monitor the location of the gas-filled microspheres, one or several pulses of sound are used and the machine pauses between pulses to receive the reflected sonic signals. The limited number of pulses used in diagnostic ultrasound limits the effective energy which is delivered to the tissue which is being imaged.

In therapeutic ultrasound, continuous wave ultrasound is used to deliver higher energy levels. In using the microspheres of the present invention, the sound energy may be pulsed, but continuous wave ultrasound is preferred. If pulsing is employed, the sound will preferably be pulsed in echo train lengths of at least about 8 and preferably at least about 20 pulses at a time.

Either fixed frequency or modulated frequency ultrasound may be used. Fixed frequency is defined wherein the frequency of the sound wave is constant over time. A modulated frequency is one in which the wave frequency changes over time, for example, from high to low (PRICH) or from low to high (CHIRP). For example, a PRICH pulse with an initial frequency of 10 MHz of sonic energy is swept to 1 MHz with increasing power from 1 to 5 watts. Focused, frequency modulated, high energy ultrasound may increase the rate of local gaseous expansion within the microspheres and rupturing to provide local delivery of therapeutics.

The frequency of the sound used may vary from about 0.025 to about 100 megahertz. Frequency ranges between about 0.75 and about 3 megahertz are preferred and frequencies between about 1 and about 2 megahertz are most preferred. Commonly used therapeutic frequencies of about 0.75 to about 1.5 megahertz may be used. Commonly used diagnostic frequencies of about 3 to about 7.5 megahertz may also be used. For very small microspheres, e.g., below 0.5 micron diameter, higher frequencies of sound may be preferred as these smaller microspheres will absorb sonic energy more effectively at higher frequencies of sound. When very high frequencies are used, e.g., over 10 megahertz, the sonic energy will generally have limited depth penetration into fluids and tissues. External application may be preferred for the skin and other superficial tissues, but for deep structures, the application of sonic energy via interstitial probes or intravascular ultrasound catheters may be preferred.

In a most preferred embodiment, the present invention provides novel liposomal drug delivery systems.

Various methods for preparing the gas-filled therapeutic containing microspheres of the present invention will be readily apparent to those skilled in the art, once armed with the present disclosure. Preferred methods for preparing the microspheres are discussed below in connection with the preferred liposomal drug delivery systems.

Specifically, in a preferred embodiment, a method for preparing a targeted drug delivery system comprising gas-filled liposomes of the subject invention comprises the steps of shaking an aqueous solution, comprising a lipid, in the presence of a gas at a temperature below the gel to liquid crystalline phase transition temperature of the lipid to form gas-filled liposomes, and adding a therapeutic compound. In another preferred embodiment, a method for preparing a targeted drug delivery system comprising gas-filled liposomes of the subject invention comprises the step of shaking an aqueous solution comprising a lipid and a therapeutic compound in the presence of a gas at a temperature below the gel to liquid crystalline phase transition temperature of the lipid. In other embodiments, methods for preparing a targeted therapeutic drug delivery system comprising gas-filled liposomes comprise the steps of shaking an aqueous solution, comprising a lipid and a therapeutic compound, in the presence of a gas, and separating the resulting gas-filled liposomes for therapeutic use. Liposomes prepared by the foregoing methods are referred to herein as gas-filled liposomes prepared by a gel state shaking gas installation method and comprising a therapeutic compound, or as therapeutic containing gel state shaken gas instilled liposomes.

Thus, a preferred method of the present invention provides for shaking an aqueous solution comprising a lipid and a therapeutic compound in the presence of a gas. Shaking, as used herein, is defined as a motion that agitates an aqueous solution such that gas is introduced from the local ambient environment into the aqueous solution. Any type of motion that agitates the aqueous solution and results in the introduction of gas may be used for the shaking. The shaking must be of sufficient force to allow the formation of foam after a period of time. Preferably, the shaking is of sufficient force such that foam is formed within a short period of time, such as 30 minutes, and preferably within 20 minutes, and more preferably, within 10 minutes. The shaking may be by swirling (such as by vortexing), side-to-side, or up and down motion. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, a shaker table such as a VWR Scientific (Cerritos, Calif.) shaker table and a mechanical paint mixer, as well as other known machines. Another means for producing shaking includes the action of gas emitted under high velocity or pressure. It will also be understood that preferably, with a larger volume of aqueous solution, the total amount of force will be correspondingly increased. Vigorous shaking is defined as at least about 60 shaking motions per minute, and is preferred. Vortexing at at least 1000 revolutions per minute, an example of vigorous shaking, is more preferred. Vortexing at 1800 revolutions per minute is most preferred.

The formation of gas-filled liposomes upon shaking can be detected by the presence of a foam on the top of the aqueous solution. This is coupled with a decrease in the volume of the aqueous solution upon the formation of foam. Preferably, the final volume of the foam is at least about two times the initial volume of the aqueous lipid solution; more preferably, the final volume of the foam is at least about three times the initial volume of the aqueous solution; even more preferably, the final volume of the foam is at least about four times the initial volume of the aqueous solution; and most preferably, all of the aqueous lipid solution is converted to foam.

The required duration of shaking time may be determined by detection of the formation of foam. For example, 10 ml of lipid solution in a 50 ml centrifuge tube may be vortexed for approximately 15–20 minutes or until the viscosity of the gas-filled liposomes becomes sufficiently thick so that it no longer clings to the side walls as it is swirled. At this time, the foam may cause the solution containing the gas-filled liposomes to raise to a level of 30 to 35 ml.

The concentration of lipid required to form a preferred foam level will vary depending upon the type of lipid used, and may be readily determined by one skilled in the art, once armed with the present disclosure. For example, in preferred embodiments, the concentration of 1,2-dipalimitoyl-phosphatidylcholine (DPPC) used to form gas-filled liposomes according to the methods of the present invention is about 20 mg/ml to about 30 mg/ml saline solution. The concentration of distearoylphosphatidylcholine (DSPC) used in preferred embodiments is about 5 mg/ml to about 10 mg/ml saline solution.

Specifically, DPPC in a concentration of 20 mg/ml to 30 mg/ml, upon shaking, yields a total suspension and entrapped gas volume four times greater than the suspension volume alone. DSPC in a concentration of 10 mg/ml, upon shaking, yields a total volume completely devoid of any liquid suspension volume and contains entirely foam.

It will be understood by one skilled in the art, once armed with the present disclosure, that the lipids or liposomes may be manipulated prior and subsequent to being subjected to the methods of the present invention. For example, the lipid may be hydrated and then lyophilized, processed through freeze and thaw cycles, or simply hydrated. In preferred embodiments, the lipid is hydrated and then lyophilized, or hydrated, then processed through freeze and thaw cycles and then lyophilized, prior to the formation of gas-filled liposomes. In a most preferred embodiment, the lipid is hydrated and shaken, followed by at least one cycle of freezing in liquid nitrogen and thawing, and then followed by lyophilization. Advantages to these treatments prior to the final formation of gas-filled liposomes include the transformation of the lipid to a solid form having a higher surface area, thus permitting better solubilization upon hydration and subsequently a higher yield of gas-filled liposomes.

According to the methods of preferred embodiments of the present invention, the presence of gas is provided by the local ambient atmosphere. The local ambient atmosphere may be the atmosphere within a sealed container, or in an unsealed container, may be the external environment. Alternatively, for example, a gas may be injected into or otherwise added to the container having the aqueous lipid solution or into the aqueous lipid solution itself in order to provide a gas other than air. Gases that are not heavier than air may be added to a sealed container while gases heavier than air may be added to a sealed or an unsealed container.

The foregoing preferred method of the invention is preferably carried out at a temperature below the gel to liquid crystalline phase transition temperature of the lipid employed. By "gel to liquid crystalline phase transition temperature", it is meant the temperature at which a lipid bilayer will convert from a gel state to a liquid crystalline state. See, for example, Chapman et al., *J. Biol. Chem.* 1974 249, 2512–2521. The gel state to liquid crystalline state phase transition temperatures of various lipids will be readily apparent to those skilled in the art and are described, for example, in Gregoriadis, ed., *Liposome Technology*, Vol. I, 1–18 (CRC Press, 1984) and Derek Marsh, *CRC Handbook of Lipid Bilayers* (CRC Press, Boca Raton, Fla. 1990), at p. 139. See also Table I, above. Where the gel state to liquid crystalline state phase transition temperature of the lipid employed is higher than room temperature, the temperature of the container may be regulated, for example, by providing a cooling mechanism to cool the container holding the lipid solution.

Conventional, aqueous-filled liposomes are routinely formed at a temperature above the gel to liquid crystalline phase transition temperature of the lipid, since they are more flexible and thus useful in biological systems in the liquid crystalline state. See, for example, Szoka and Papahadjopoulos, *Proc. Natl. Acad. Sci.* 1978 75, 4194–4198. In contrast, the liposomes made according to preferred embodiments of the methods of the present invention are gas-filled, which imparts greater flexibility since gas is more compressible and compliant than an aqueous solution. Thus, the gas-filled liposomes may be utilized in biological systems when formed at a temperature below the phase transition temperature of the lipid, even though the gel phase is more rigid.

Figure 9:
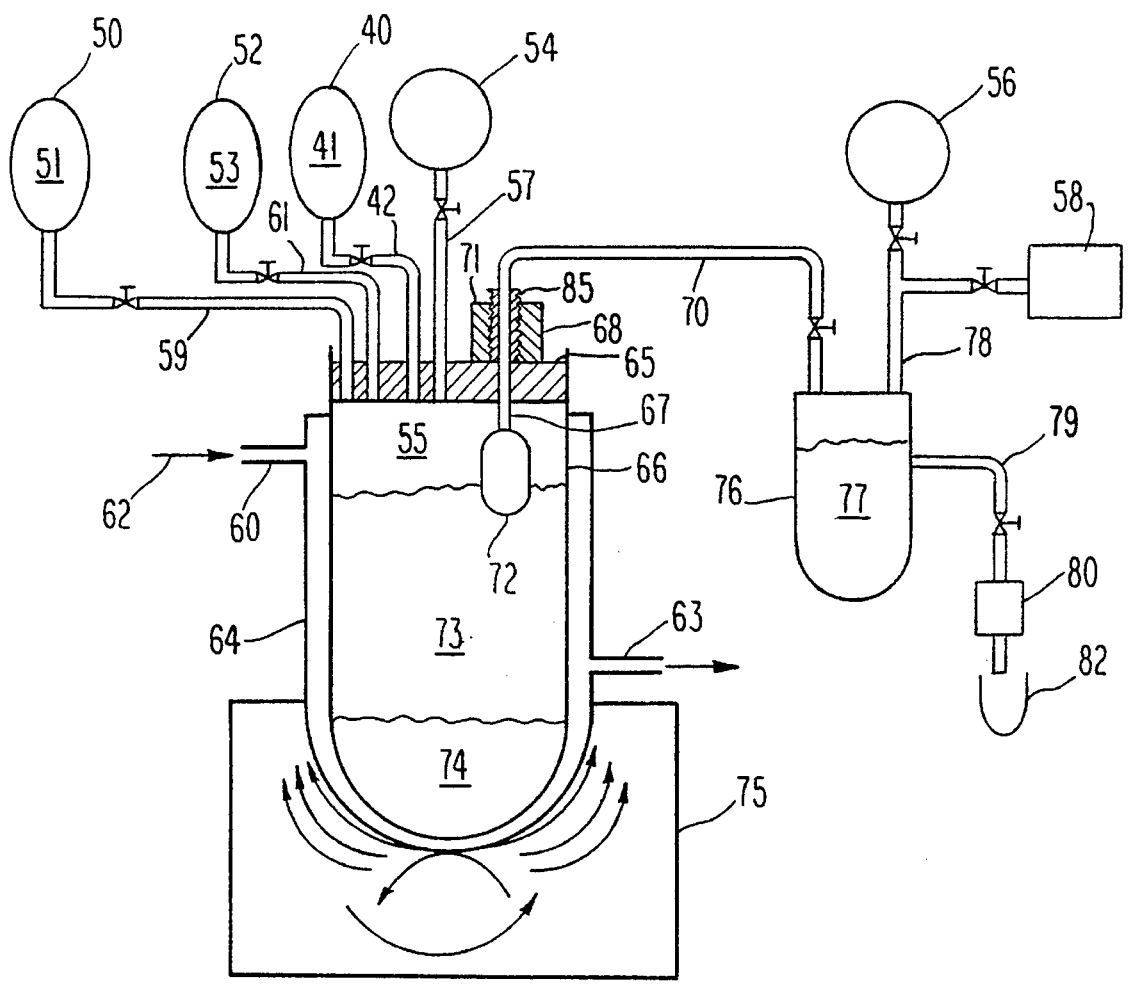
FIG. 9 is a view, partially schematic, of a preferred apparatus according to the present invention for preparing the therapeutic containing gas-filled liposome microspheres of the present invention.

A preferred apparatus for producing the therapeutic containing gas-filled liposomes using a gel state shaking gas instillation process is shown in FIG. 9. A mixture of lipid and aqueous media is vigorously agitated in the process of gas installation to produce gas-filled liposomes, either by batch or by continuous feed. Referring to FIG. 9, dried lipids 51 from a lipid supply vessel 50 are added via conduit 59 to a mixing vessel 66 in either a continuous flow or as intermittent boluses. If a batch process is utilized, the mixing vessel 66 may comprise a relatively small container such as a syringe, test tube, bottle or round bottom flask, or a large container. If a continuous feed process is utilized, the mixing vessel is preferably a large container, such as a vat.

The therapeutic compound may be added, for example, before the gas installation process. Referring to FIG. 9, the therapeutic compound 41 from a therapeutic compound supply vessel 40 is added via conduit 42 to a mixing vessel 66. Alternatively, the therapeutic compound may be added after the gas installation process, such as when the liposomes are coated on the outside with the therapeutic compound.

In addition to the lipids 51, and therapeutic compound 41, an aqueous media 53, such as a saline solution, from an aqueous media supply vessel 52, is also added to the vessel 66 via conduit 61. The lipids 51 and the aqueous media 53 combine to form an aqueous lipid solution 74. Alternatively, the dried lipids 51 could be hydrated prior to being introduced into the mixing vessel 66 so that lipids are introduced in an aqueous solution. In the preferred embodiment of the method for making liposomes, the initial charge of solution 74 is such that the solution occupies only a portion of the capacity of the mixing vessel 66. Moreover, in a continuous process, the rates at which the aqueous lipid solution 74 is added and gas-filled liposomes produced are removed is controlled to ensure that the volume of lipid solution 74 does not exceed a predetermined percentage of the mixing vessel 66 capacity.

The shaking may be accomplished by introducing a high velocity jet of a pressurized gas directly into the aqueous lipid solution 74. Alternatively, the shaking may be accomplished by mechanically shaking the aqueous solution, either manually or by machine. Such mechanical shaking may be effected by shaking the mixing vessel 66 or by shaking the aqueous solution 74 directly without shaking the mixing vessel itself. As shown in FIG. 9, in the preferred embodiment, a mechanical shaker 75, is connected to the mixing vessel 66. The shaking should be of sufficient intensity so that, after a period of time, a foam 73 comprised of gas-filled liposomes is formed on the top of the aqueous solution 74, as shown in FIG. 9. The detection of the formation of the foam 73 may be used as a means for controlling the duration of the shaking; that is, rather than shaking for a predetermined period of time, the shaking may be continued until a predetermined volume of foam has been produced.

In a preferred embodiment of the apparatus for making gas-filled liposomes in which the lipid employed has a gel to liquid crystalline phase transition temperature below room temperature, a means for cooling the aqueous lipid solution 74 is provided. In the embodiment shown in FIG. 9, cooling is accomplished by means of a jacket 64 disposed around the mixing vessel 66 so as to form an annular passage surrounding the vessel. As shown in FIG. 9, a cooling fluid 63 is forced to flow through this annular passage by means of jacket inlet and outlet ports 62 and 63, respectively. By regulating the temperature and flow rate of the cooling fluid 62, the temperature of the aqueous lipid solution 74 can be maintained at the desired temperature.

As shown in FIG. 9, a gas 55, which may be air or another gas, such as nitrogen or argon, is introduced into the mixing vessel 66 along with the aqueous solution 74. Air may be introduced by utilizing an unsealed mixing vessel so that the aqueous solution is continuously exposed to environmental air. In a batch process, a fixed charge of local ambient air may be introduced by sealing the mixing vessel 66. If a gas heavier than air is used, the container need not be sealed. However, introduction of gases that are not heavier than air will require that the mixing vessel be sealed, for example by use of a lid 65, as shown in FIG. 9. Whether the gas 55 is air or another gas, it may be pressurized in the mixing vessel 66, for example, by connecting the mixing vessel to a pressurized gas supply tank 54 via a conduit 57, as shown in FIG. 9.

After the shaking is completed, the gas-filled liposome containing foam 73 may be extracted from the mixing vessel 66. Extraction may be accomplished by inserting the needle 102 of a syringe 100, shown in FIG. 10, into the foam 73 and drawing a predetermined amount of foam into the barrel 104 by withdrawing the plunger 106. As discussed further below, the location at which the end of the needle 102 is placed in the foam 73 may be used to control the size of the gas-filled liposomes extracted.

Alternatively, extraction may be accomplished by inserting an extraction tube 67 into the mixing vessel 66, as shown in FIG. 9. If the mixing vessel 66 is pressurized, as previously discussed, the pressure of the gas 55 may be used to force the gas-filled liposomes 77 from the mixing vessel 66 to an extraction vessel 76 via conduit 70. In the event that the mixing vessel 66 is not pressurized, the extraction vessel 76 may be connected to a vacuum source 58, such as a vacuum pump, via conduit 78, that creates sufficient negative pressure to suck the foam 73 into the extraction vessel 76, as shown in FIG. 9. From the extraction vessel 76, the gas-filled liposomes 77 are introduced into vials 82 in which they may be shipped to the ultimate user. A source of pressurized gas 56 may be connected to the extraction vessel 76 as aid to ejecting the gas-filled liposomes. Since negative pressure may result in increasing the size of the gas-filled liposomes, positive pressure is preferred for removing the gas-filled liposomes.

Figure 12:
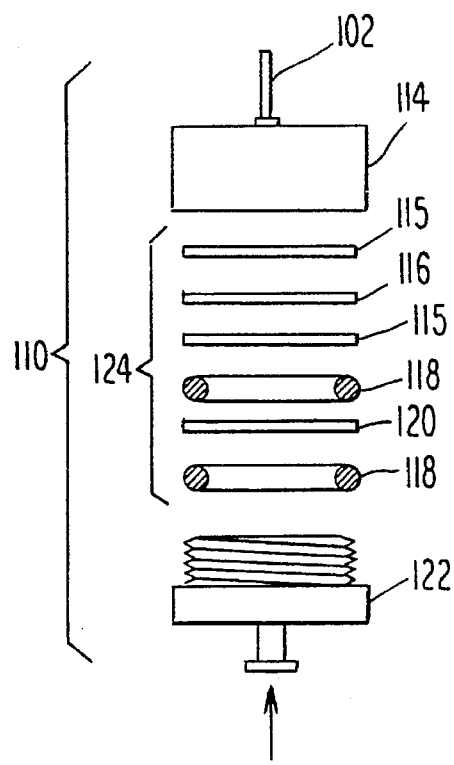
FIG. 12 is an exploded view of a portion of the apparatus of FIG. 11.
Figure 15A:
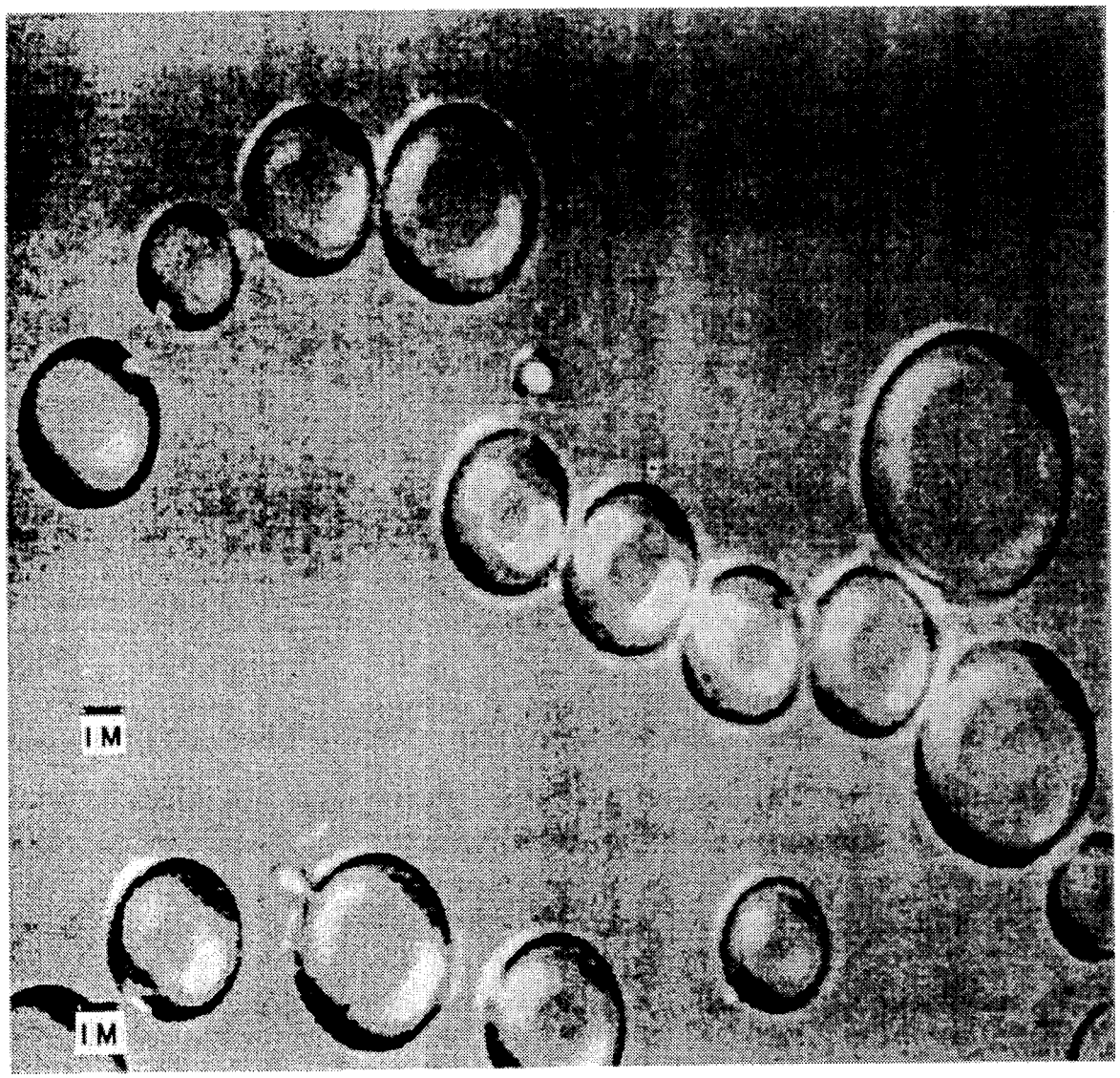
FIGS. 15A and 15B are micrographs which shows the sizes of gas-filled liposomes of the invention before (FIG. 15A) and after (FIG. 15B) through a 10 micron filter filtration.
Figure 15B:
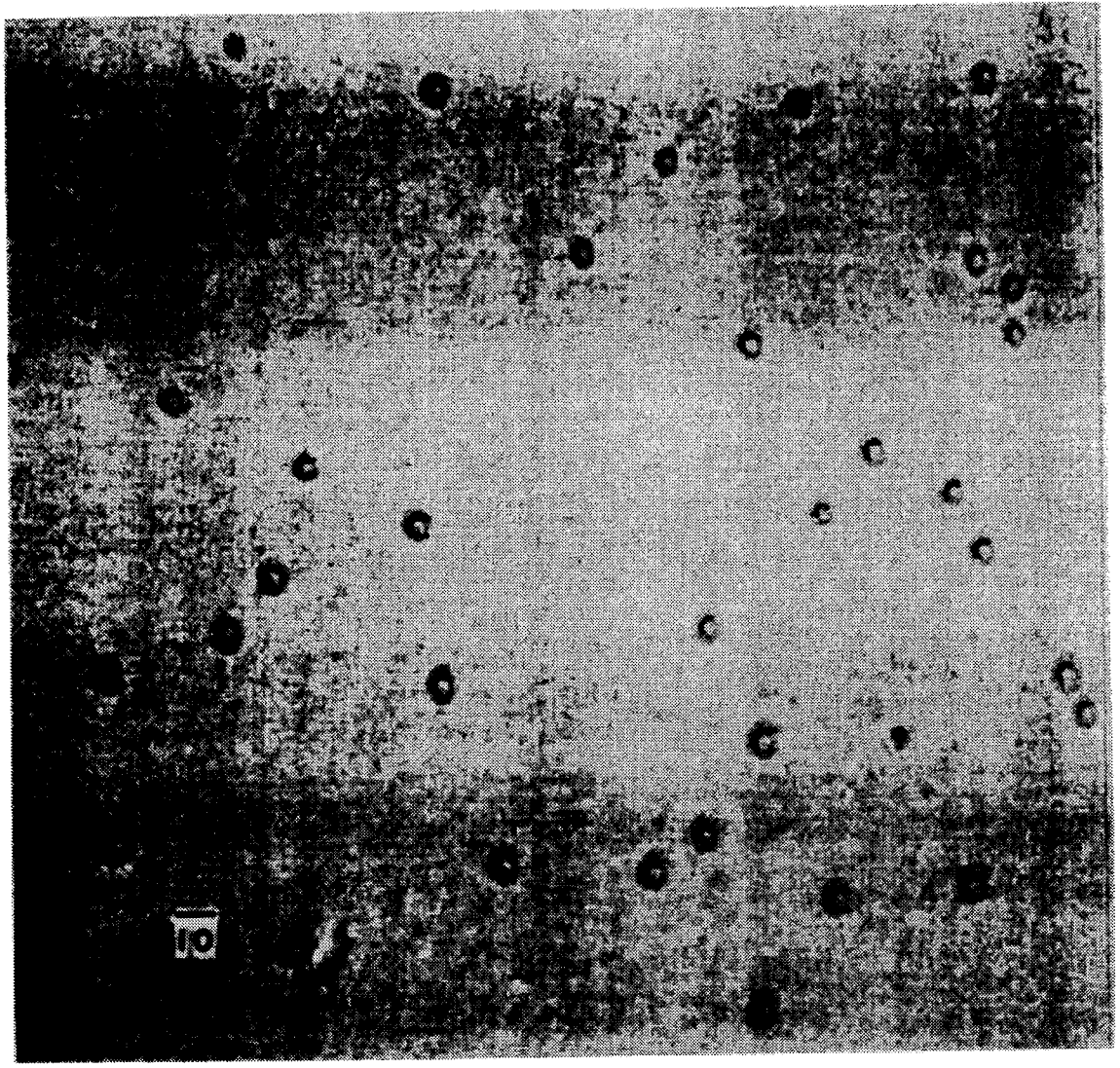
Figure 16A:
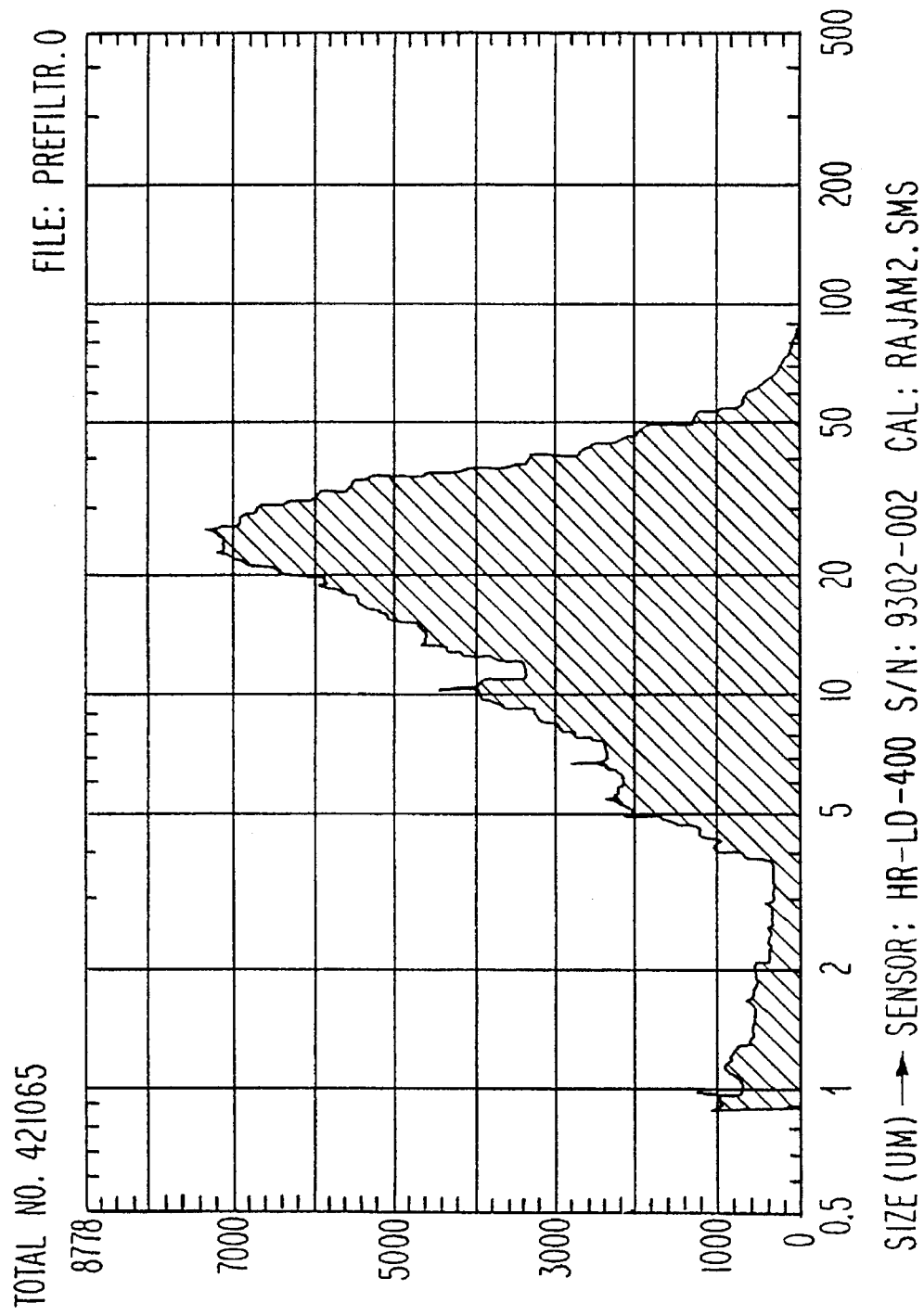
FIGS. 16A and 16B graphically depict the size distribution of gas-filled liposomes of the invention before (FIG. 16A) and after (FIG. 16B) filtration through a set of cascade filters of 10 μm and 8 μm.
Figure 16B:
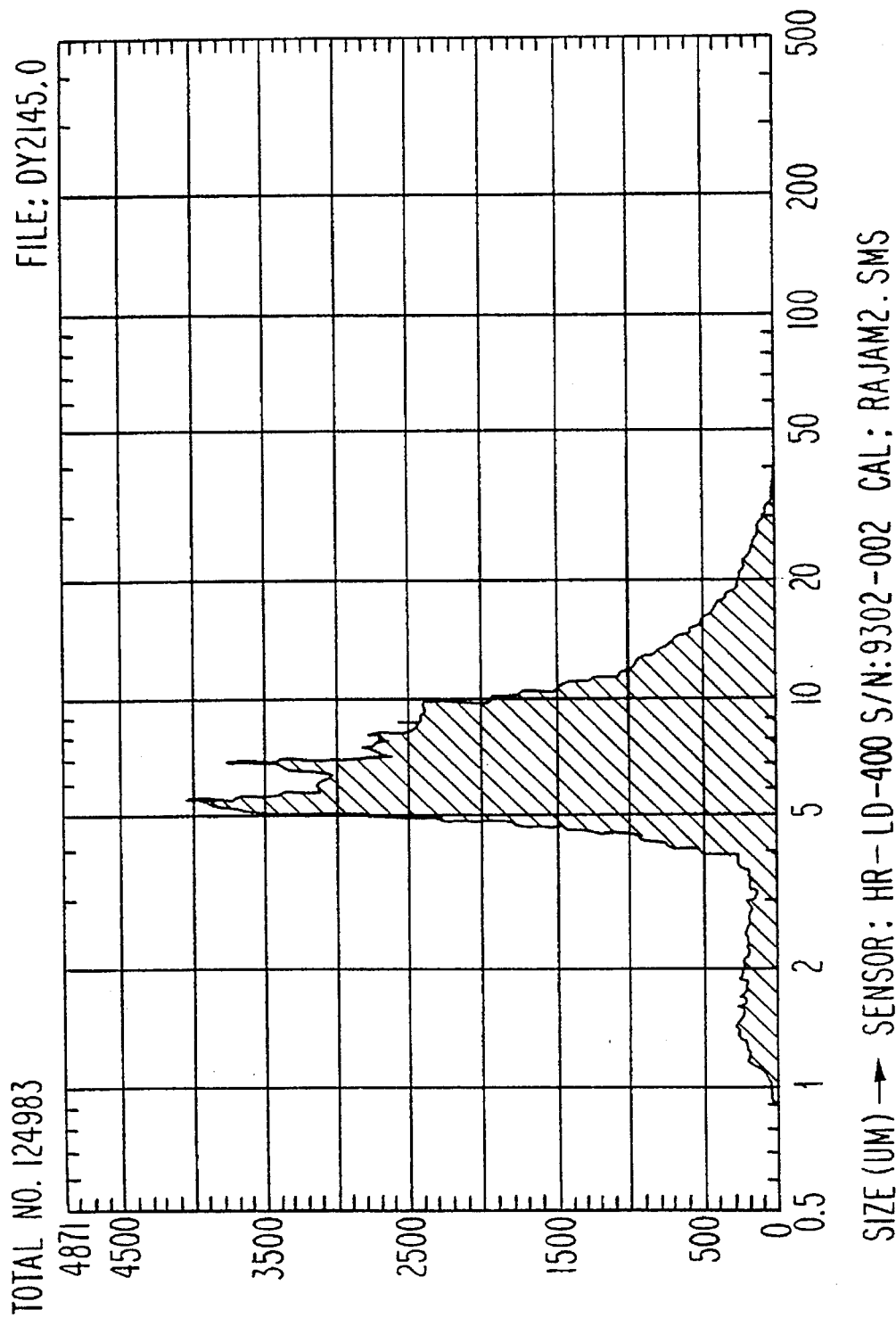

Filtration is preferably carried out in order to obtain gas-filled liposomes of a substantially uniform size. In certain preferred embodiments, the filtration assembly contains more than one filter, and preferably, the filters are not immediately adjacent to each other, as illustrated in FIG. 12. Before filtration, the gas-filled liposomes range in size from about 1 micron to greater than 60 microns (FIGS. 15A and 16A). After filtration through a single filter, the gas-filled liposomes are generally less than 10 microns but particles as large as 25 microns in size remain. After filtration through two filters (10 micron followed by 8 micron filter), almost all of the liposomes are less than 10 microns, and most are 5 to 7 microns (FIGS. 15B and 16B).

As shown in FIG. 9, filtering may be accomplished by incorporating a filter element 72 directly onto the end of the extraction tube 67 so that only gas-filled liposomes below a pre-determined size are extracted from the mixing vessel 66. Alternatively, or in addition to the extraction tube filter 72, gas-filled liposome sizing may be accomplished by means of a filter 80 incorporated into the conduit 79 that directs the gas-filled liposomes 77 from the extraction vessel 76 to the vials 82, as shown in FIG. 9. The filter 80 may contain a cascade filter assembly 124, such as that shown in FIG. 12. The cascade filter assembly 124 shown in FIG. 12 comprises two successive filters 116 and 120, with filter 120 being disposed upstream of filter 116. In a preferred embodiment, the upstream filter 120 is a "NUCLEPORE" 10 μm filter and the downstream filter 116 is a "NUCLEPORE" 8 μm filter. Two 0.15 mm metallic mesh discs 115 are preferably installed on either side of the filter 116. In a preferred embodiment, the filters 116 and 120 are spaced apart a minimum of 150 μm by means of a Teflon™ O-ring, 118.

In addition to filtering, sizing may also be accomplished by taking advantage of the dependence of gas-filled liposome buoyancy on size. The gas-filled liposomes have appreciably lower density than water and hence will float to the top of the mixing vessel 66. Since the largest liposomes have the lowest density, they will float most quickly to the top. The smallest liposomes will generally be last to rise to the top and the non gas-filled lipid portion will sink to the bottom. This phenomenon may be advantageously used to size the gas-filled liposomes by removing them from the mixing vessel 66 via a differential flotation process. Thus, the setting of the vertical location of the extraction tube 66 within the mixing vessel 66 may control the size of the gas-filled liposomes extracted; the higher the tube, the larger the gas-filled liposomes extracted. Moreover, by periodically or continuously adjusting the vertical location of the extraction tube 67 within the mixing vessel 66, the size of the gas-filled liposomes extracted may be controlled on an on-going basis. Such extraction may be facilitated by incorporating a device 68, which may be a threaded collar 71 mating with a threaded sleeve 72 attached to the extraction tube 67, that allows the vertical location of the extraction tube 67 within the extraction vessel 66 to be accurately adjusted.

The gel state shaking gas installation process itself may also be used to improve sizing of the gas-filled lipid based microspheres. In general, the greater the intensity of the shaking energy, the smaller the size of the resulting gas-filled liposomes.

Figure 10:
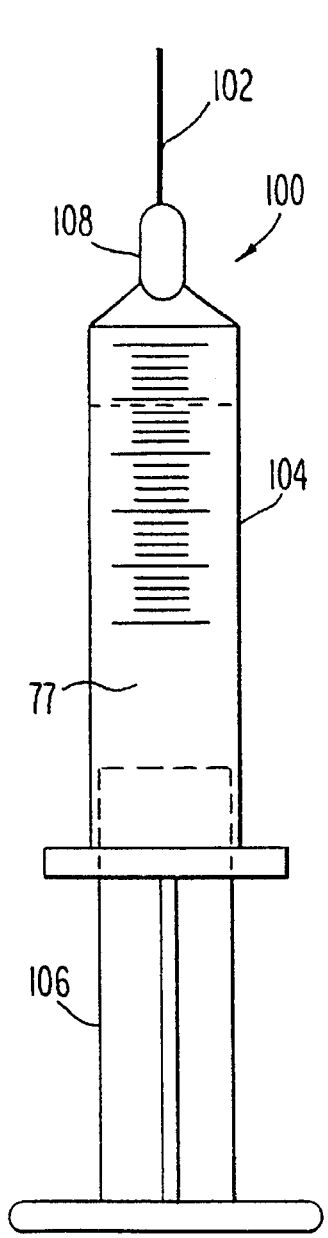
FIG. 10 shows a preferred apparatus for filtering and/or dispensing therapeutic containing gas-filled liposome microspheres of the present invention.

The current invention also includes novel methods for preparing drug-containing gas-filled liposomes to be dispensed to the ultimate user. Once gas-filled liposomes are formed, they can not be sterilized by heating at a temperature that would cause rupture. Therefore, it is desirable to form the gas-filled liposomes from sterile ingredients and to perform as little subsequent manipulation as possible to avoid the danger of contamination. According to the current invention, this may be accomplished, for example, by sterilizing the mixing vessel containing the lipid and aqueous solution before shaking and dispensing the gas-filled liposomes 77 from the mixing vessel 66, via the extraction vessel 76, directly into the barrel 104 of a sterile syringe 100, shown in FIG. 10, without further processing or handling; that is, without subsequent sterilization. The syringe 100, charged with gas-filled liposomes 77 and suitably packaged, may then be dispensed to the ultimate user. Thereafter, no further manipulation of the product is required in order to administer the gas-filled liposomes to the patient, other than removing the syringe from its packaging and removing a protector (not shown) from the syringe needle 102 and inserting the needle into the body of the patient, or into a catheter. Moreover, the pressure generated when the syringe plunger 106 is pressed into the barrel 104 will cause the largest gas-filled liposomes to collapse, thereby achieving a degree of sizing without filtration.

Where it is desired to filter the gas-filled liposomes at the point of use, for example because they are removed from the extraction vessel 76 without filtration or because further filtration is desired, the syringe 100 may be fitted with its own filter 108, as shown in FIG. 10. This results in the gas-filled liposomes being sized by causing them to be extruded through the filter 108 by the action of the plunger 106 when the gas-filled liposomes are injected. Thus, the gas-filled liposomes may be sized and injected into a patient in one step.

Figure 11:
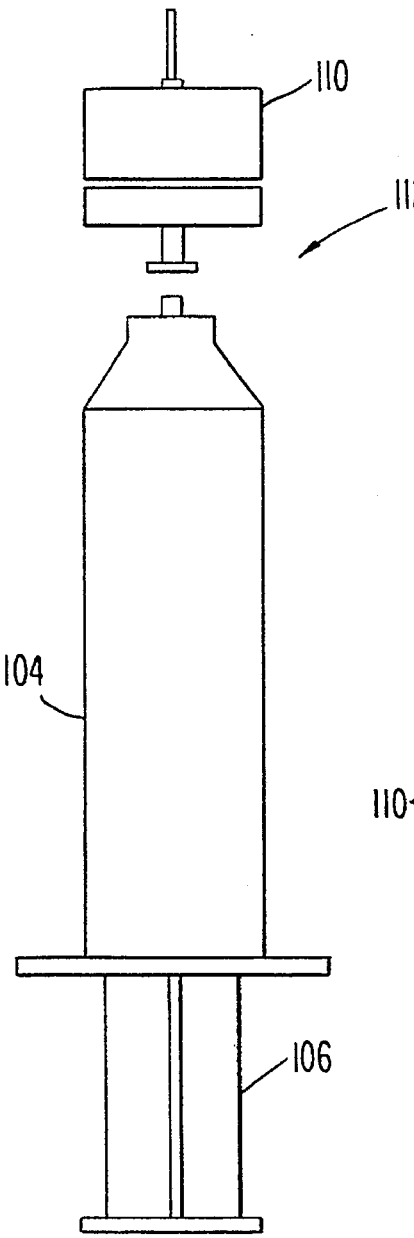
FIG. 11. depicts a preferred apparatus for filtering and/or dispensing therapeutic containing gas-filled liposome microspheres of the present invention.

As shown in FIG. 11, a cascade filter housing 110 may be fitted directly onto a syringe 112, thereby allowing cascade filtration at the point of use. As shown in Figure 12, the filter housing 110 is comprised of a cascade filter assembly 124, previously discussed, incorporated between a lower collar 122, having male threads, and a female collar 114, having female threads. The lower collar 122 is fitted with a Luer lock that allows it to be readily secured to the syringe 112 and the upper collar 114 is fitted with a needle 102.

In preferred embodiments, the lipid solution is extruded through a filter and the lipid solution is heat sterilized prior to shaking. Once gas-filled liposomes are formed, they may be filtered for sizing as described above. These steps prior to the formation of gas-filled liposomes provide the advantages, for example, of reducing the amount of unhydrated lipid and thus providing a significantly higher yield of gas-filled liposomes, as well as and providing sterile gas-filled liposomes ready for administration to a patient. For example, a mixing vessel such as a vial or syringe may be filled with a filtered lipid suspension, and the solution may then be sterilized within the mixing vessel, for example, by autoclaving. Gas may be instilled into the lipid suspension to form gas-filled liposomes by shaking the sterile vessel. Preferably, the sterile vessel is equipped with a filter positioned such that the gas-filled liposomes pass through the filter before contacting a patient.

Figure 17A:
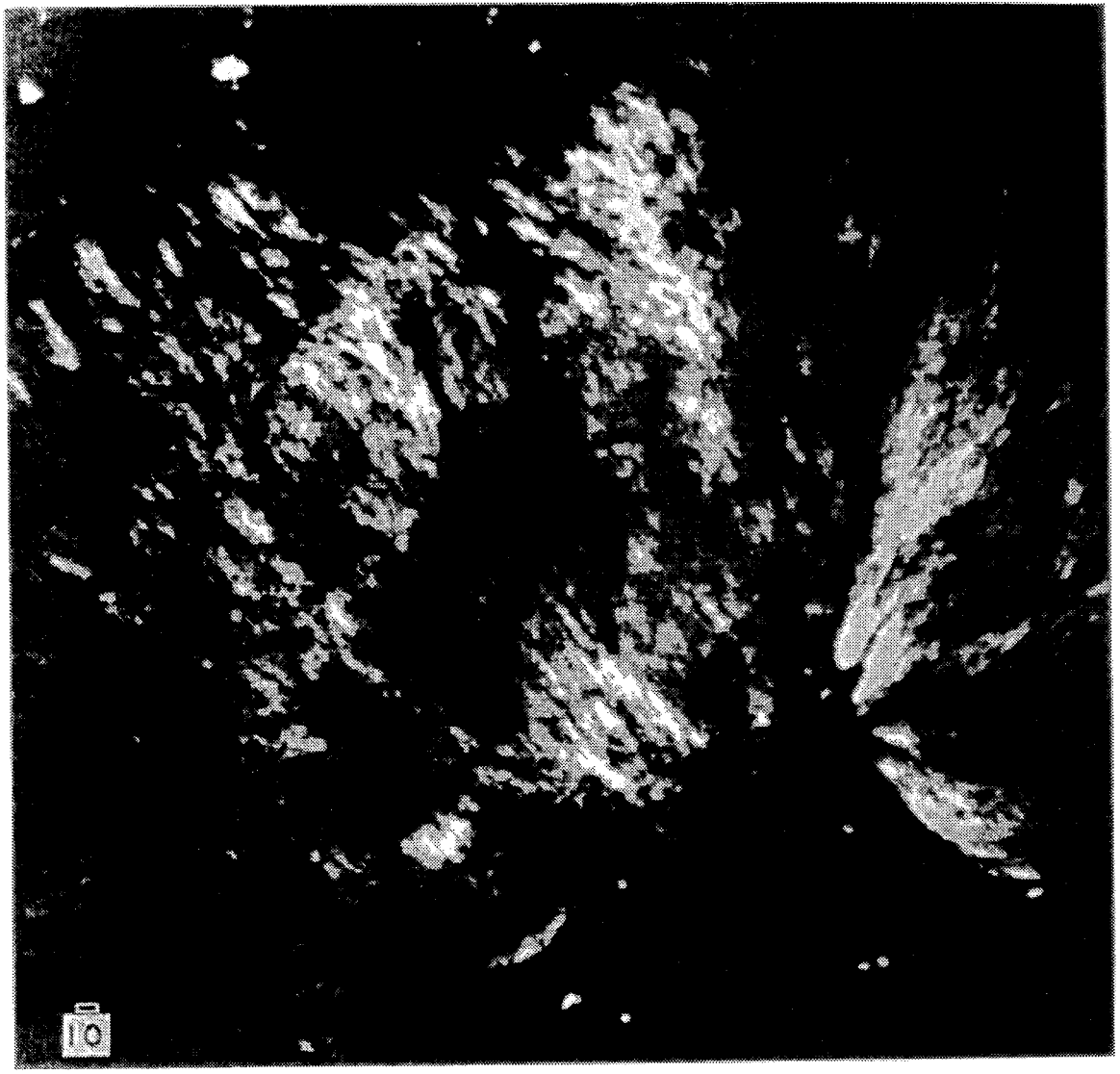
FIG. 17A and 17B are micrographs of a DPPC lipid suspension before (FIG. 16A) and after (FIG. 17B) extrusion through a filter. The scale bar is 10 μm.
Figure 17B:
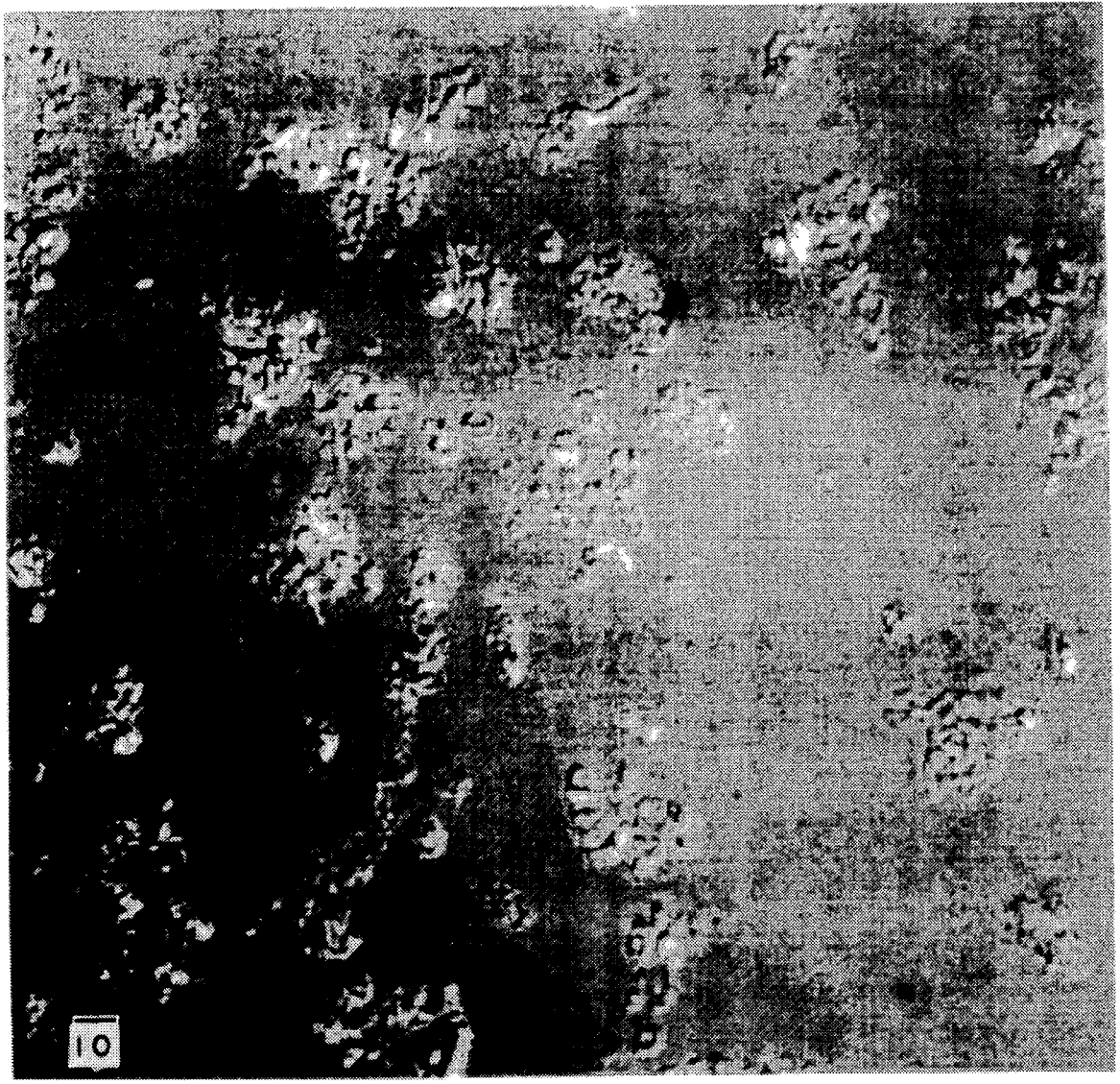

The first step of this preferred method, extruding the lipid solution through a filter, decreases the amount of unhydrated lipid by breaking up the dried lipid and exposing a greater surface area for hydration. Preferably, the filter has a pore size of about 0.1 to about 5 μm, more preferably, about 0.1 to about 4 μm, even more preferably, about 0.1 to about 2 μm, and most preferably, about 1 μm. As shown in FIGS. 17A and 17B when a lipid suspension is filtered (FIG. 17B), the amount of unhydrated lipid is reduced when compared to a lipid suspension that was not pre-filtered (FIG. 17A). Unhydrated lipid appears as amorphous clumps of non-uniform size and is undesirable.

The second step, sterilization, provides a composition that may be readily administered to a patient. Preferably, sterilization is accomplished by heat sterilization, preferably, by autoclaving the solution at a temperature of at least about 100° C., and more preferably, by autoclaving at about 100° C. to about 130° C., even more preferably, about 110° C. to about 130° C., even more preferably, about 120° C. to about 130° C., and most preferably, about 130° C. Preferably, heating occurs for at least about 1 minute, more preferably, about 1 to about 30 minutes, even more preferably, about 10 to about 20 minutes, and most preferably, about 15 minutes.

Where sterilization occurs by a process other than heat sterilization at a temperature which would cause rupture of the gas-filled liposomes, sterilization may occur subsequent to the formation of the gas-filled liposomes, and is preferred. For example, gamma radiation may be used before and/or after gas-filled liposomes are formed.

Figure 18A:
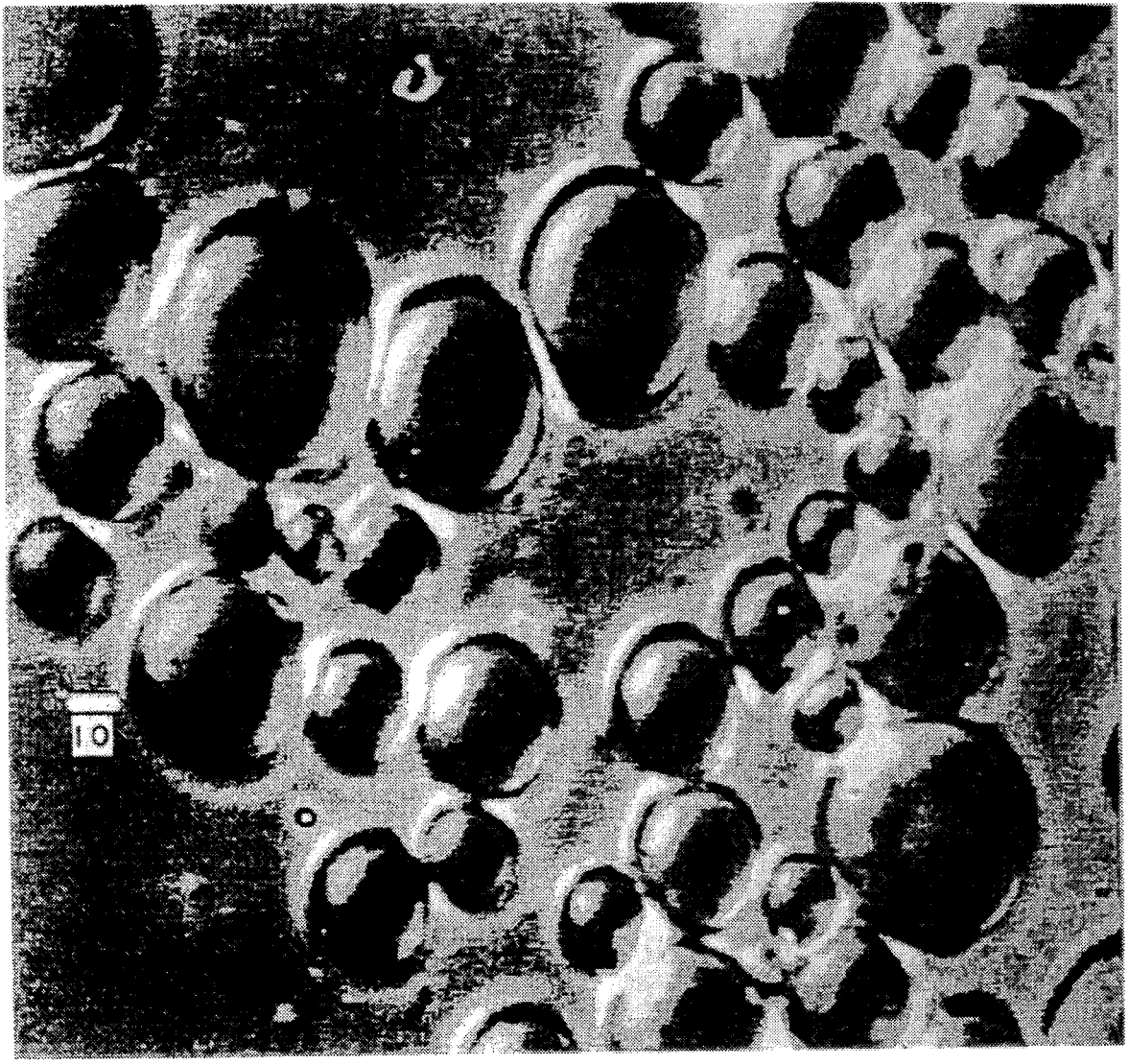
FIG. 18 is a micrograph of gas-filled liposomes formed subsequent to filtering and autoclaving a lipid suspension, the micrographs having been taken before (A) and after (B) sizing by filtration of the gas-filled liposomes.
Figure 18B:
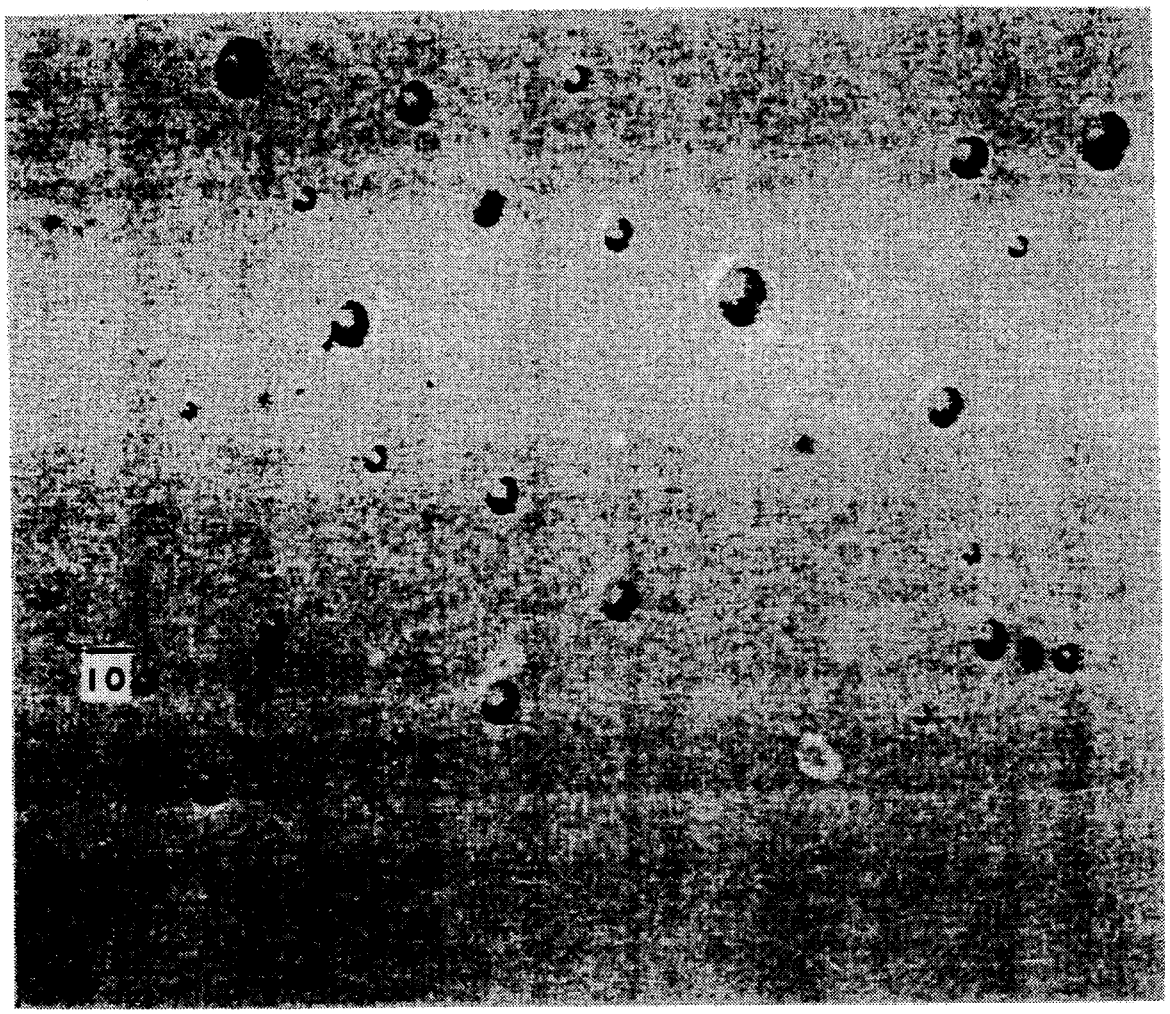

FIG. 18A and 18B illustrate the ability of gas-filled liposomes to successfully form after autoclaving, which was carried out at 130° C. for 15 minutes, followed by vortexing for 10 minutes. Further, after the extrusion and sterilization procedure, the shaking step yields gas-filled liposomes with little to no residual anhydrous lipid phase. FIG. 18A shows gas-filled liposomes generated after autoclaving but prior to filtration, thus resulting in a number of gas-filled liposomes having a size greater than 10 μm. FIG. 18B shows gas-filled liposomes after a filtration through a 10 μm "NUCLEPORE" filter, resulting in a uniform size around 10 μm.

Certain embodiments of the present invention are directed to drug delivery systems comprising gas-filled liposomes prepared by vacuum drying gas instillation methods and having encapsulated therein a therapeutic (that is, drug containing), such liposomes sometimes being referred to herein as drug containing vacuum dried gas instilled liposomes. The present invention is further directed to drug delivery systems comprising drug containing gas-filled liposomes substantially devoid of liquid in the interior thereof.

This method for preparing the liposomes of the subject invention comprises: (i) placing liposomes encapsulating a drug under negative pressure; (ii) incubating the liposomes under the negative pressure for a time sufficient to remove substantially all liquid from the liposomes; and (iii) instilling selected gas into the liposomes until ambient pressures are achieved. Methods employing the foregoing steps are referred to herein as the vacuum drying gas instillation methods for preparing drug containing liposomes.

Apparatus is also provided for preparing the liposomes of the invention using the vacuum drying gas instillation methods, said apparatus comprising: (i) a vessel containing liposomes having encapsulated therein a drug; (ii) means for applying negative pressure to the vessel to draw liquid from the liposomes contained therein; (iii) a conduit connecting the negative pressurizing means to the vessel, the conduit directing the flow of said liquid; and (iv) means for introducing a gas into the liposomes in the vessel.

The vacuum drying gas instillation method employed to prepare both the subject gas-filled liposomes prepared by the vacuum drying gas instillation method, and the gas-filled liposomes substantially devoid of liquid in the interior thereof, contemplates the following process. First, in accordance with the process, the drug containing liposomes are placed under negative pressure (that is, reduced pressure or vacuum conditions). Next, the liposomes are incubated under that negative pressure for a time sufficient to remove substantially all liquid from the liposomes, thereby resulting in substantially dried liposomes. By removal of substantially all liquid, and by substantially dried liposomes, as those phrases are used herein, it is meant that the liposomes are at least about 90% devoid of liquid, preferably at least about 95% devoid of liquid, most preferably about 100% devoid of liquid. Although the liquid is removed, the drug, with its higher molecular weight, remains behind, encapsulated in the liposome. Finally, the liposomes are instilled with selected gas by applying the gas to the liposomes until ambient pressures are achieved, thus resulting in the subject drug containing vacuum dried gas instilled liposomes of the present invention, and the drug containing gas-filled liposomes of the invention substantially devoid of liquid in the interior thereof. By substantially devoid of liquid in the interior thereof, as used herein, it is meant liposomes having an interior that is at least about 90% devoid of liquid, preferably at least about 95% devoid of liquid, most preferably about 100% devoid of liquid.

Unexpectedly, the drug containing liposomes prepared in accordance with the methods of the present invention possess a number of surprising yet highly beneficial characteristics. The liposomes of the invention exhibit intense echogenicity on ultrasound, will rupture on application of peak resonant frequency ultrasound (as well as other resonant frequencies of sufficient intensity and duration), are highly stable to pressure, and/or generally possess a long storage life, either when stored dry or suspended in a liquid medium. The gas-filled liposomes also have the advantages, for example, of stable particle size, low toxicity and compliant membranes. It is believed that the flexible membranes of the gas-filled liposomes may be useful in aiding the accumulation or targeting of these liposomes to tissues such as tumors. Also unexpected is the ability of the liposomes during the vacuum drying gas instillation process to fill with gas and resume their original circular shape, rather than irreversibly collapse into a cup-like shape.

Figure 13:
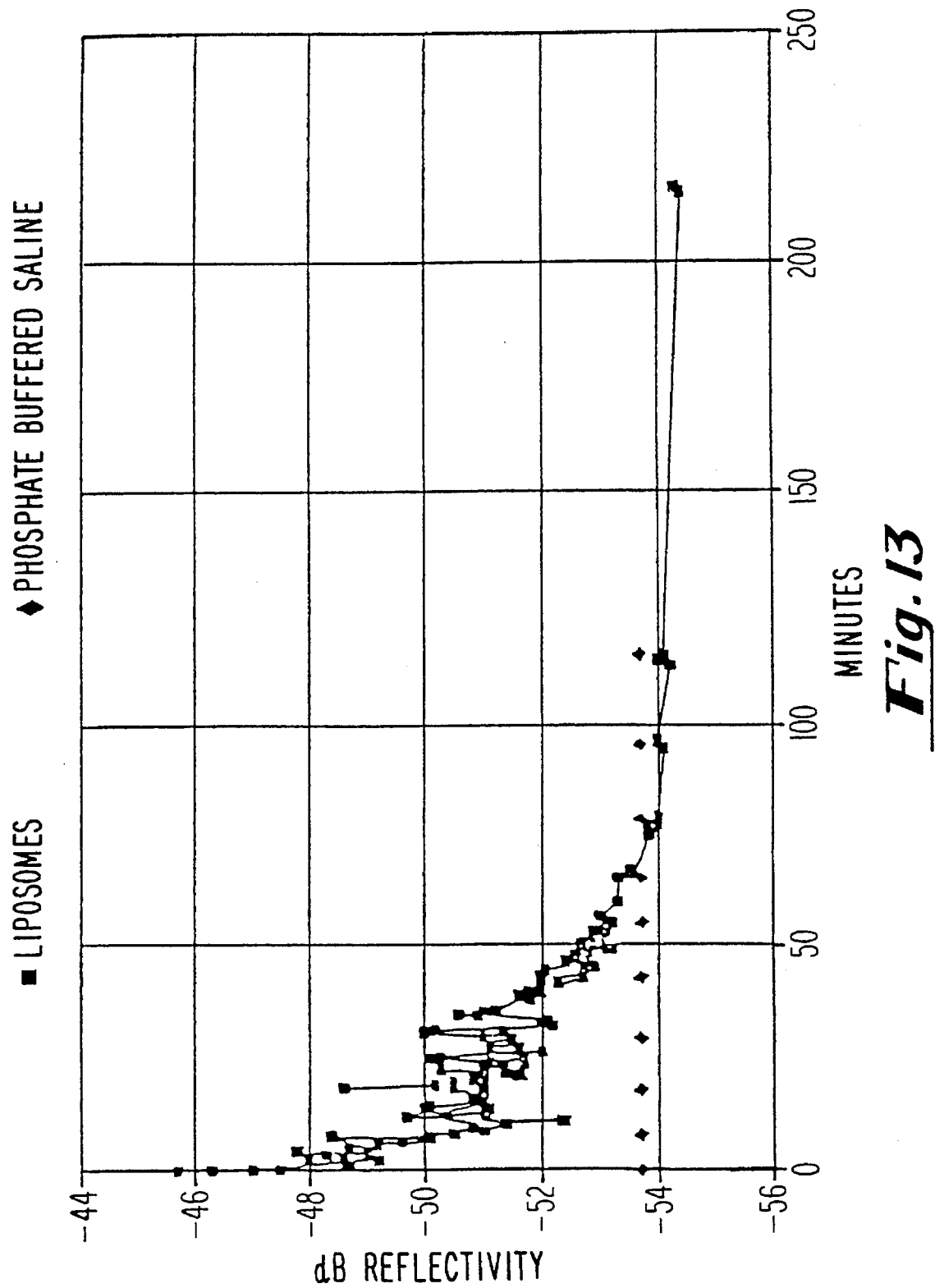
FIG. 13 is a graphical representation of the dB reflectivity of gas-filled liposomes substantially devoid of liquid in the interior thereof prepared by the vacuum drying gas instillation method, without any drugs encapsulated therein. The data was obtained by scanning with a 7.5 megahertz transducer using an Acoustic Imaging™ Model 5200 scanner (Acoustic Imaging, Phoenix, Ariz.), and was generated by using the system test software to measure reflectivity. The system was standardized prior to each experiment with a phantom of known acoustic impedance.

The echogenicity of the liposomes and the ability to rupture the liposomes at the peak resonant frequency using ultrasound permits the controlled delivery of drugs to a region of a patient by allowing the monitoring of the liposomes following administration to a patient to determine the presence of liposomes in a desired region, and the rupturing of the liposomes using ultrasound to release the drugs in the region. Preferably, the liposomes of the invention possess a reflectivity of greater than 2 dB, preferably between about 4 dB and about 20 dB. Within these ranges, the highest reflectivity for the liposomes of the invention is exhibited by the larger liposomes, by higher concentrations of liposomes, and/or when higher ultrasound frequencies are employed. See FIG. 13, which is a graphical representation of the dB reflectivity of gas-filled liposomes substantially devoid of liquid in the interior thereof prepared by the vacuum drying gas instillation method, without any drugs encapsulated therein. Preferably, the liposomes of the invention have a peak resonant frequency of between about 0.5 mHz and about 10 mHz. Of course, the peak resonant frequency of the gas-filled liposomes of the invention will vary depending on the diameter and, to some extent, the elasticity of the liposomes, with the larger and more elastic liposomes having a lower resonant frequency than the smaller and more elastic liposomes.

The stability of the liposomes of the invention is also of great practical importance. The subject liposomes tend to have greater stability during storage than other gas-filled liposomes produced via known procedures such as pressurization or other techniques. At 72 hours after formation, for example, conventionally prepared gas containing liposomes often are essentially devoid of gas, the gas having diffused out of the liposomes and/or the liposomes having ruptured and/or fused, resulting in a concomitant loss in reflectivity. In comparison, drug containing gas-filled liposomes of the present invention generally have a shelf life stability of greater than about three weeks, preferably a shelf life stability of greater than about four weeks, more preferably a shelf life stability of greater than about five weeks, even more preferably a shelf life stability of greater than about three months, and often a shelf life stability that is even much longer, such as over six months, twelve months, or even two years.

Also unexpected is the ability of the liposomes during the vacuum drying gas instillation process to fill with gas and resume their original circular shape, rather than collapse into a cup-shaped structure, as the prior art would cause one to expect. See, e.g., Crowe et al., *Archives of Biochemistry and Biophysics*, Vol. 242, pp. 240–247 (1985); Crowe et al., *Archives of Biochemistry and Biophysics*, Vol. 220, pp. 477–484 (1983); Fukuda et al., *J. Am. Chem. Soc., Vol.* 108, pp. 2321–2327 (1986); Regen et al., *J. Am. Chem. Soc.*, Vol. 102, pp. 6638–6640 (1980).

The drug containing liposomes subjected to the vacuum drying gas instillation method of the invention may be prepared using any one of a variety of conventional liposome preparatory techniques which will be apparent to those skilled in the art. Although any of a number of varying techniques can be employed, preferably the drug containing liposomes are prepared via microemulsification techniques. The liposomes produced by the various conventional procedures can then be employed in the vacuum drying gas instillation method of the present invention, to produce the drug containing liposomes of the present invention.

The materials which may be utilized in preparing liposomes to be employed in the vacuum drying gas instillation method of the present invention include any of the materials or combinations thereof known to those skilled in the art as suitable for liposome construction.

Liposomes may be prepared prior to gas installation using any one of a variety of conventional liposome preparatory techniques which will be apparent to those skilled in the art. These techniques include freeze-thaw, as well as techniques such as sonication, chelate dialysis, homogenization, solvent infusion, microemulsification, spontaneous formation, solvent vaporization, French pressure cell technique, controlled detergent dialysis, and others, each involving preparing the liposomes in various fashions in a solution containing the desired therapeutic so that the therapeutic is encapsulated in, enmeshed in, or attached the resultant liposome. Alternatively, therapeutics may be loaded into the liposomes using pH gradient techniques which, as those skilled in the art will recognize, is particularly applicable to therapeutics which either proteinate or deproteinate at a particular pH. See, e.g., Madden et al., *Chemistry and Physics of Lipids,* 1990 53, 37–46, the disclosures of which are hereby incorporated herein by reference in their entirety.

To prepare the drug containing liposomes for vacuum drying gas installation, and by way of general guidance, dipalmitoylphosphatidylcholine liposomes, for example, may be prepared by suspending dipalmitoylphosphatidylcholine lipids in phosphate buffered saline or water containing the drug to be encapsulated, and heating the lipids to about 50° C., a temperature which is slightly above the 41° C. temperature required for transition of the dipalmitoylphosphatidylcholine lipids from a gel state to a liquid crystalline state, to form drug containing liposomes.

To prepare multilamellar vesicles of a rather heterogeneous size distribution of around 2 microns, the liposomes may then be mixed gently by hand while keeping the liposome solution at a temperature of about 50° C. The temperature is then lowered to room temperature, and the liposomes remain intact. Extrusion of dipalmitoylphosphatidylcholine liposomes through polycarbonate filters of defined size may, if desired, be employed to make liposomes of a more homogeneous size distribution. A device useful for this technique is an extruder device (Extruder Device™ Lipex Biomembranes, Vancouver, Canada) equipped with a thermal barrel so that extrusion may be conveniently accomplished above the gel state to liquid crystalline state phase transition temperature for lipids.

For lipophilic drugs which are sparingly soluble in aqueous media, such drugs may be mixed with the lipids themselves prior to forming the liposomes. For example, amphotericin may be suspended with the dried lipids (e.g., 8:2 molar ratio of egg phosphatidylcholine and cholesterol in chloroform and mixed with the lipids). The chloroform is then evaporated (note that other suitable organic solvents may also be used, such as ethanol or ether) and the dried lipids containing a mixture of the lipophilic drug are then resuspended in aqueous media, e.g., sterile water or physiologic saline. This process may be used for a variety of lipophilic drugs such as corticosteroids to incorporate lipophilic drugs into the liposome membranes. The resulting liposomes are then dried, subjected to the vacuum gas instillation method as described above.

Alternatively, and again by way of general guidance, conventional freeze-thaw procedures may be used to produce either oligolamellar or unilamellar dipalmitoylphosphatidylcholine liposomes. After the freeze-thaw procedures, extrusion procedures as described above may then be performed on the liposomes.

The drug containing liposomes thus prepared may then be subjected to the vacuum drying gas instillation process of the present invention, to produce the drug containing vacuum dried gas instilled liposomes, and the drug containing gas-filled liposomes substantially devoid of liquid in the interior thereof, of the invention. In accordance with the process of the invention, the drug containing liposomes are placed into a vessel suitable for subjecting to the liposomes to negative pressure (that is, reduced pressure or vacuum conditions). Negative pressure is then applied for a time sufficient to remove substantially all liquid from the liposomes, thereby resulting in substantially dried liposomes. As those skilled in the art would recognize, once armed with the present disclosure, various negative pressures can be employed, the important parameter being that substantially all of the liquid has been removed from the liposomes. Generally, a negative pressure of at least about 700 mm Hg and preferably in the range of between about 700 mm Hg and about 760 mm Hg (gauge pressure) applied for about 24 to about 72 hours, is sufficient to remove substantially all of the liquid from the liposomes. Other suitable pressures and time periods will be apparent to those skilled in the art, in view of the disclosures herein.

Finally, a selected gas is applied to the liposomes to instill the liposomes with gas until ambient pressures are achieved, thereby resulting in the drug containing vacuum dried gas instilled liposomes of the invention, and in the drug containing gas-filled liposomes substantially devoid of liquid in the interior thereof. Preferably, gas instillation occurs slowly, that is, over a time period of at least about 4 hours, most preferably over a time period of between about 4 and about 8 hours.

Various biocompatible gases may be employed. Such gases include air, nitrogen, carbon dioxide, oxygen, argon, xenon, neon, helium, or any and all combinations thereof. Other suitable gases will be apparent to those skilled in the art, the gas chosen being only limited by the proposed application of the liposomes.

The above described method for production of liposomes is referred to hereinafter as the vacuum drying gas instillation process.

If desired, the liposomes may be cooled, prior to subjecting the liposomes to negative pressure, and such cooling is preferred. Preferably, the liposomes are cooled to below 0° C., more preferably to between about –10° C. and about –20° C., and most preferably to –10° C., prior to subjecting the liposomes to negative pressure. Upon reaching the desired negative pressure, the liposomes temperature is then preferably increased to above 0° C., more preferably to between about 10° C. and about 20° C., and most preferably to 10° C., until substantially all of the liquid has been removed from the liposomes and the negative pressure is discontinued, at which time the temperature is then permitted to return to room temperature.

If the liposomes are cooled to a temperature below 0° C., it is preferable that the vacuum drying gas instillation process be carried out with liposomes either initially prepared in the presence of cryoprotectants, or liposomes to which cryoprotectants have been added prior to carrying out the vacuum drying gas instillation process of the invention. Such cryoprotectants, while not mandatorily added, assist in maintaining the integrity of liposome membranes at low temperatures, and also add to the ultimate stability of the membranes. Preferred cryoprotectants are trehalose, glycerol, polyethyleneglycol (especially polyethyleneglycol of molecular weight 400), raffinose, sucrose and sorbitol, with trehalose being particularly preferred.

It has also been surprisingly discovered that the liposomes of the invention are highly stable to changes in pressure. Because of this characteristic, extrusion of the liposomes through filters of defined pore size following vacuum drying and gas instillation can be carried out, if desired, to create liposomes of relatively homogeneous and defined pore size.

Figure 14:
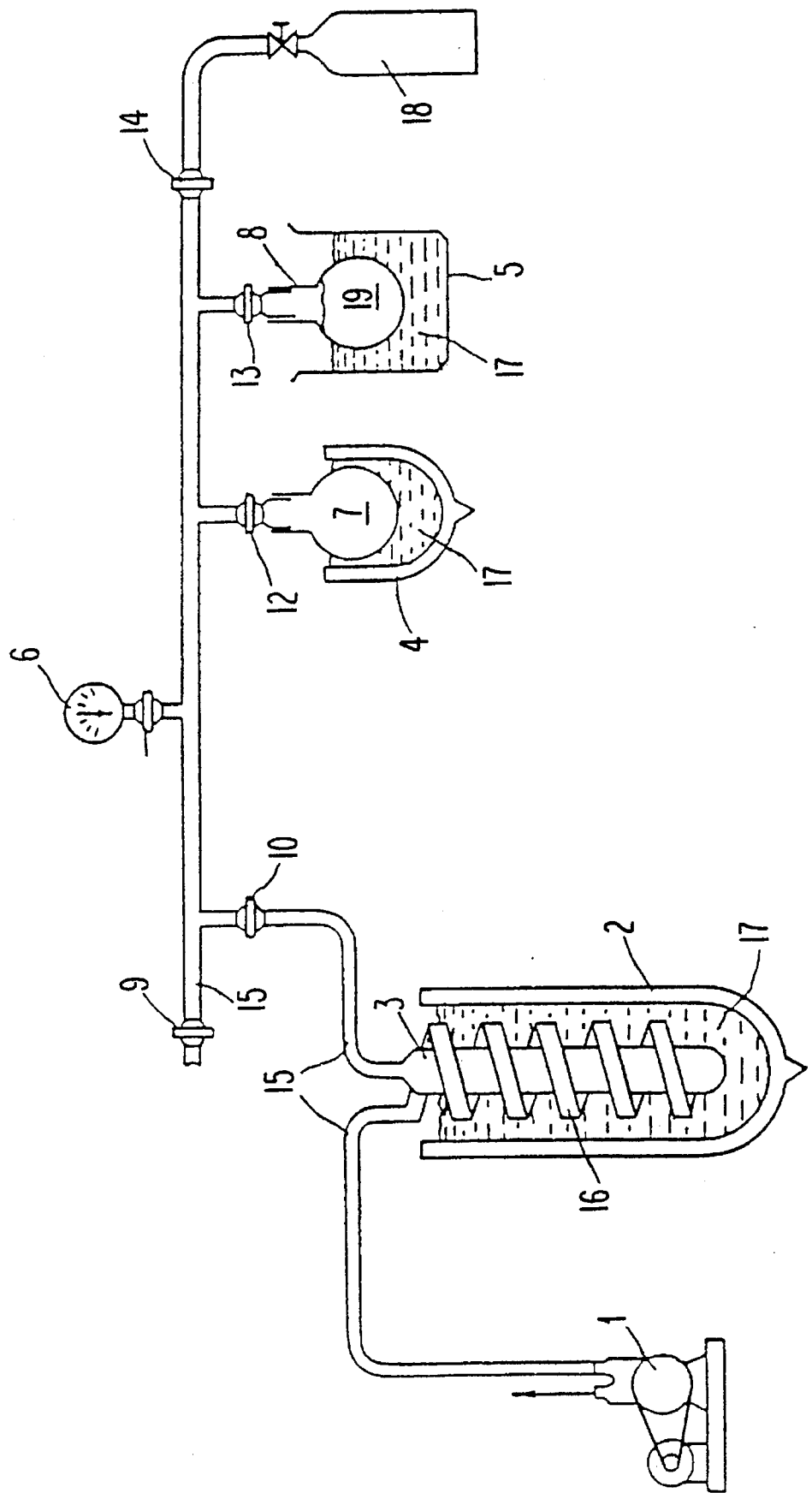
FIG. 14 shows a preferred apparatus for preparing the drug containing vacuum dried gas instilled liposomes, and the drug containing gas-filled liposomes substantially devoid of liquid in the interior thereof prepared by the vacuum drying gas instillation method.

As another aspect of the invention, useful apparatus for preparing the drug containing vacuum dried gas instilled liposomes, and the drug containing gas-filled liposomes substantially devoid of liquid in the interior thereof, of the invention is also presented. Specifically, there is shown in FIG. 14 a preferred apparatus for vacuum drying liposomes and instilling a gas into the dried liposomes. The apparatus is comprised of a vessel 8 for containing drug containing liposomes 19. If desired, the apparatus may include an ice bath 5 containing dry ice 17 surrounding the vessel 8. The ice bath 5 and dry ice 17 allow the liposomes to be cooled to below 0° C. A vacuum pump 1 is connected to the vessel 8 via a conduit 15 for applying a sustained negative pressure to the vessel. In the preferred embodiment, the pump 1 is capable of applying a negative pressure of at least about 700 mm Hg, and preferably a negative pressure in the range of about 700 mm Hg to about 760 mm Hg (gauge pressure). A manometer 6 is connected to the conduit 15 to allow monitoring of the negative pressure applied to the vessel 8.

In order to prevent liquid removed from the liposomes from entering the pump 1, a series of traps are connected to the conduit 15 to assist in collecting the liquid (and liquid vapor, all collectively referred to herein as liquid) drawn from the liposomes. In a preferred embodiment, two traps are utilized. The first trap is preferably comprised of a flask 7 disposed in an ice bath 4 with dry ice 17. The second trap is preferably comprised of a column 3 around which tubing 16 is helically arranged. The column 3 is connected to the conduit 15 at its top end and to one end of the tubing 16 at its bottom end. The other end of the tubing 16 is connected to the conduit 15. As shown in FIG. 14, an ice bath 2 with dry ice 17 surrounds the column 3 and tubing 16. If desired, dry ice 17 can be replaced with liquid nitrogen, liquid air or other cryogenic material. The ice baths 2 and 4 assist in collecting any liquid and condensing any liquid vapor drawn from the liposomes for collection in the traps. In preferred embodiments of the present invention the ice traps 2 and 4 are each maintained at a temperature of least about −70° C.

A stopcock 14 is disposed in the conduit 15 upstream of the vessel 8 to allow a selected gas to be introduced into the vessel 8 and into the liposomes 19 from gas bottle 18.

Apparatus of the present invention are utilized by placing the drug containing liposomes 19 into vessel 8. In a preferable embodiment, ice bath 5 with dry ice 17 is used to lower the temperature of the liposomes to below 0° C., more preferably to between about −10° C. and about −20° C., and most preferably to −10° C. With stopcocks 14 and 9 closed, vacuum pump 1 is turned on. Stopcocks 10, 11, 12 and 13 are then carefully opened to create a vacuum in vessel 8 by means of vacuum pump 1. The pressure is gauged by means of manometer 6 until negative pressure of at least about 700 mm Hg, and preferably in the range of between about 700 mm Hg and about 760 mm Hg (gauge pressure) is achieved. In preferred embodiments of the present invention vessel 7, cooled by ice bath 4 with dry ice 17, and column 3 and coil 16, cooled by ice bath 2 with dry ice 17, together or individually condense liquid vapor and trap liquid drawn from the liposomes so as to prevent such liquids and liquid vapor from entering the vacuum pump 1. In preferred embodiments of the present invention, the temperature of ice traps 2 and 4 are each maintained at a temperature of at least about −70° C. The desired negative pressure is generally maintained for at least 24 hours as liquid and liquid vapor is removed from the liposomes 19 in vessel 8 and frozen in vessels 3 and 7. Pressure within the system is monitored using manometer 6 and is generally maintained for about 24 to about 72 hours, at which time substantially all of the liquid has been removed from the liposomes. At this point, stopcock 10 is slowly closed and vacuum pump 1 is turned off. Stopcock 14 is then opened gradually and gas is slowly introduced into the system from gas bottle 18 through stopcock 14 via conduit 15 to instill gas into the drug containing liposomes 19 in vessel 8. Preferably the gas instillation occurs slowly over a time period of at least about 4 hours, most preferably over a time period of between about 4 and about 8 hours, until the system reaches ambient pressure.

The drug containing vacuum dried gas instilled liposomes and the drug containing gas-filled liposomes substantially devoid of liquid in the interior thereof, of the present invention, have superior characteristics as drug delivery vehicles.

The gas-filled liposomes prepared according to the methods of the present invention are believed to differ from the liposomes of the prior art in a number of respects, both in physical and in functional characteristics. For example, the liposomes of the invention are substantially devoid of liquid in the interior thereof. By definition, liposomes in the prior art have been characterized by the presence of an aqueous medium. See, e.g., *Dorland's Illustrated Medical Dictionary*, p. 946, 27th ed. (W. B. Saunders Company, Philadelphia 1988). Moreover, the present liposomes surprisingly exhibit intense echogenicity on ultrasound, are susceptible to rupture upon application of ultrasound at the peak resonant frequency of the liposomes, and possess a long storage life, characteristics of great benefit to the use of the liposomes as drug delivery systems.

Thus the invention contemplates methods for the controlled delivery of drugs to a region of a patient comprising: (i) administering to the patient the gas-filled liposomes prepared by vacuum drying gas instillation methods and having encapsulated therein a drug, and/or gas-filled liposomes substantially devoid of liquid in the interior thereof and having encapsulated therein a drug; (ii) monitoring the liposomes using ultrasound to determine the presence of the liposomes in the region; and (iii) rupturing the liposomes using ultrasound to release the drugs in the region.

There are various other applications for liposomes of the invention, beyond those described in detail herein. Such additional uses, for example, include such applications as hyperthermia potentiators for ultrasound and as contrast agents for ultrasonic imaging. Such additional uses and other related subject matter are described and claimed in Applicant's patent applications, U.S. Ser. No. 716,793 and U.S. Ser. No. 717,084, both of which were filed Jun. 18, 1991, the disclosures of each of which are incorporated herein by reference in their entirety.

The present invention is further described in the following examples. Example 1 is an actual example that describes the preparation, testing and use of the gas-filled microspheres containing a therapeutic. Examples 2–10 are prophetic examples that describe the preparation, testing and use of the gas-filled microspheres containing a therapeutic. Examples 11–20 are prophetic examples that describe the preparation, testing and use of the drug-containing vacuum dried, gas instilled liposomes, the gas-filled liposomes being substantially devoid of any liquid in the interior thereof. Examples 21–28 are actual examples that illustrate the preparation and testing of the gas-filled liposomes prepared by shaking an aqueous solution comprising a lipid in the presence of a gas. Examples 29–36 are actual examples that illustrate the preparation and sizing of gas-filled liposomes prepared by filtering and autoclaving a lipid suspension, followed by shaking the lipid solution. The following examples should not be construed as limiting the scope of the appended claims.

EXAMPLES

Example 1

The methods described below demonstrate that a therapeutic such as DNA can be entrapped in gas-filled microspheres and that ultrasound can be used to release a therapeutic from a gas-filled microsphere. As shown below, liposomes entrapping water and DNA failed to release the genetic material after exposure to the same amount of ultrasonic energy. The presence of the gas within the microspheres results in much more efficient capture of the ultrasonic energy so it can be utilized for delivery of a therapeutic such as genetic material.

Gas-filled liposomes were synthesized as follows: Pure dipalmitoylphosphatidylcholine (DPPC), Avanti Polar Lipids, Alabaster, Ala., was suspended in normal saline and then Extruded five times through 2 micron polycarbonate filters (Nuclepore, Costar, Pleasanton, Calif.) using an Extruder Device (Lipex Biomembranes, Vancouver, Canada) at 800 p.s.i. The resulting liposomes were then dried under reduced pressure as described in U.S. Ser. No. 716,899, filed Jun. 18, 1991, which is hereby incorporated by reference in its entirety. After thorough drying the dried liposomes were then slowly filled with nitrogen gas, as described in U.S. Ser. No. 716,899. After equilibration with ambient pressure, the resulting liposomes were suspended in saline solution (0.9% NaCl) and shaken vigorously.

The resulting gas-filled liposomes were then tested for size by Coulter Counter (Bedfordshire, England). The machine was calibrated using the calibration procedure described in the reference manual supplied with the Coulter Counter. The gas-filled liposome solution was diluted with Isoton II and placed in a glass container and was stirred at the 3 position of the Coulter Sampling Stand.

A 100 μm aperture tube was used first. With this aperture tube, 500 microliters of solution was tested at a time for each of the selected size ranges. The next size aperture tube that was used was a 30 μm aperture tube. Microspheres can be sized down to about 1 μm with this tube, in which the mean diameter of the gas-filled microspheres was detected.

50 microliters of solution were tested at a time and microspheres were counted for each of the size ranges selected. Data was collected on both the Coulter Counter model ZM and the Coulter Counter Channelyzer 256. Quasi-elastic light scattering (QEL) and light microscopy were also used. Latex beads with predetermined sizes were used to calibrate the grids in the ocular lens. These grids were calibrated for each of the magnifications of 10×, 40×, 100×, 400×, and 1000×. The gas-filled microspheres were then placed on the glass slide and viewed under different magnifications. This technique results in sizing not only of gas-filled liposomes, but also lipid particles.

The gas-filled liposomes were scanned by sonic energy using both an Acoustic Imaging Model 5200 clinical ultrasound device (Acoustic Imaging Technologies Corp., Phoenix, Ariz.) and a custom built bench top device. The bench top acoustic lab consists of a Lecroy 9410 Digital Oscilloscope (Lecroy Corporation Corporate Headquarters, Chestnut Ridge, N.Y.), a Panametrics model 5052PR Pulser/Receiver (Panametrics, Inc., Waltham, Mass.), Panametrics immersion transducers with frequencies of 2.25, 3.5, 5.0, 7.5, and 10.0 MHz (Panametrics, Inc., Waltham, Mass), and an alignment system by Testech, Inc. (Testech, Inc., Exton, Pa.). A reference standard, a tissue mimicking phantom, was used to set the time-gain compensation (TGC) and thus the average amplitude is set in this manner. The tissue mimicking phantom is made by Radiation Measurements, Inc. (Middleton, Wis.).

As shown in Table III, the reflectivity of the gas-filled liposomes remains constant for the highest energies of pulsed sound used in these experiments over the ranges of frequencies tested. Specifically, dB reflectivity of the gas-filled liposomes remains constant despite continual scanning for 60 minutes at a power setting between 4.5–8.4 mW and an acoustic intensity of 3.25 mW/cm$^2$ (the highest power setting of pulsed sound which could be generated by the Acoustic Imaging AI5200 clinical ultrasound machine).

TABLE III

Reflectivity of Gas-Filled Microspheres

| time (minutes) | Average Amplitude (dB reflectivity) |
| --- | --- |
| 0 | −34.1 |
| 15 | −36.0 |
| 30 | −36.2 |
| 45 | −36.8 |
| 60 | −37.1 |

Solutions of gas-filled liposomes were also subjected to continuous wave ultrasound energy (Table IV) applied with a Rich-Mar Therapeutic ultrasound apparatus model RM-25 (Rich-Mar Corp., Inola, Okla.). Table IV demonstrates the power produced using continuous wave ultrasound. It was found that continuous wave energy of sound caused the gas inside the gas-filled liposomes to escape from the liposomes, thus rupturing the liposomes. It took approximately 20–30 minutes to completely destroy the gas-filled liposomes in a solution of saline at 5 watts of power and at 1 MHz. It took approximately 5 minutes to destroy the gas-filled liposomes at 10 watts and at 1 MHz. When the gas-filled liposomes were examined by light microscopy before and after application of high energy ultrasound the spherical shape of the gas-filled liposomes disappeared after exposure.

TABLE IV

Power Output and Intensity of Continuous Wave Ultrasound

| | Total ultrasonic power output P (mW) | Average Intensity at transducer face $I_{ID}$ (W/m²) |
|---|---|---|
| Continuous wave | 5000 | 9867 |
| Continuous wave | 10000 | 19735 |

Gas-filled microspheres were then tested for their ability to deliver DNA in a series of experiments. Liposomes were prepared from DPPC as described above except that 2 μg of DNA on a 7000 bp plasmid (pCH110: Pharmacia LKB Biotechnology, Piscataway, N.J.), in 1 cc of normal saline were added during resuspension of the dried DPPC. Gas-filled liposomes were then prepared as described above. After resuspension of the gas-filled liposomes, external unentrapped DNA was removed by affinity chromatography. The suspension of gas-filled liposomes and DNA was eluted through a column (DNA specific Sephadex®) using a peristaltic pump (Econopump, Bio-Rad Laboratories, Hercules, Calif.). The DNA affinity substrate binds to and retains the unentrapped DNA. The gas-filled microspheres elute out.

Liposomes filled with water were also prepared as described above to entrap DNA except that the drying gas instillation step was omitted. Unentrapped DNA was removed via chromatography. The gas-filled liposomes were then scanned ultrasonically as described above. The gas-filled liposomes containing DNA were similarly echogenic to pulsed ultrasound as described above. After scanning with continuous wave ultrasound as described above, the microspheres lost their echogenicity.

After treatment with continuous wave ultrasound, a propidium iodide dimer assay for free DNA (i.e., DNA external to the gas-filled liposomes) was performed and compared to control gas-filled liposomes containing DNA (i.e., not exposed to continuous wave ultrasound).

First, a 2 ml aliquot of the gas-filled microspheres was added to a test tube. 2 ml of PBS (phosphate-buffered saline) was then added, and the tube was sealed with parafilm. The test tube was then inverted several times and allowed to stand for about 5 minutes to allow separation of the microspheres. The bottom aqueous layer was then removed from the tube with a Pasteur pipette. This procedure was repeated for a total of three times to wash the microspheres.

Next, a 2 ml aliquot of DNA at 0.05 μg/ml was added to the microspheres, the test tube was sealed and inverted to mix. After settling for about 5 minutes, the bottom aqueous layer was extracted with a Pasteur pipette. Another 2 ml aliquot of PBS was then added and the procedure repeated to wash off any unbound DNA. This procedure was repeated for a total of five times and the aqueous layers were saved for analysis.

The microspheres were then diluted with 2 ml of PBS and ultrasound was applied until there was no visual evidence of the gas-filled microspheres.

14 μl of propidium iodide dimer (POPO-3 iodide, Molecular Probes, Inc., Eugene, Oreg.), at a concentration of $2\times10^{-5}$M in DMSO was added to each 2 ml sample after the ultrasound was applied in order to detect released DNA. As a control, 14 μl of propidium iodide was added to PBS alone, and to 0.025 μg/ml DNA in PBS.

Samples were measured for fluorescence in a Spex Fluorolog 2 Spectrophotometer using an excitation frequency of 534 nm. The emissions were recorded at 558 nm as indicated in Table V below. A percentage of the relative amount of DNA found in each sample was determined by extrapolation based upon the control PBS sample, which consisted of the propidium iodide dimer in PBS.

TABLE V

| Sample | Fluorescence (% DNA) |
|---|---|
| 1st wash | 58885 (45%) |
| 2nd wash | 40314 (17%) |
| 3rd wash | 33195 (7%) |
| 4th wash | 30062 (8%) |
| 5th wash | 34336 (21%) |
| Ultrasound exposed sample | 43051 (21%) |
| Control - PBS alone | 28878 |
| Control - PBS + DNA | 50563 |

The wash cycles served to remove any unbound DNA. As illustrated in Table V above, after five wash cycles, the gas-filled microspheres still contained about 21% plasmid DNA.

Gas-filled liposomes containing DNA not exposed to high energy ultrasound retained a substantial amount of their DNA internally as indicated by the absence of an appreciable increase in fluorescence from propidium iodide dimer. After exposure to continuous wave ultrasound, however, the fluorescence from propidium iodide was markedly increased indicating the high degree of release of DNA from the gas-filled microspheres caused by the continuous wave ultrasound energy. Thus, DNA was retained by the microspheres until ultrasound was applied. Upon the application of ultrasound, the entrapped DNA was released.

Example 2

A cationic lipid, such as DOTMA is mixed as a 1:3 molar ratio with DPPC. The mixed material is dissolved in chloroform and the chloroform is removed by rotary evaporation. Water is added to the dried material and this mixture is then extruded through a 2 μm filter using an Extruder Device (Lipex Biomembranes, Inc., Vancouver, BC). Then positively charged gas-filled liposomes are prepared according to the procedure provided in U.S. Ser. No. 717,084, filed Jun. 18, 1991, which is hereby incorporated by reference in its entirety.

The resulting dried, positively charged gas-filled liposomes are rehydrated by adding PBS, saline or other appropriate buffered solution (such as HEPES buffer); a vortexer may be used to insure homogenous mixing. DNA is added and the mixture is again shaken. Since the DNA is attached to the surface of the cationic gas-filled liposomes, unattached DNA may be removed with filtering or selective chromatography. Essentially all of the DNA binds up until the point where the cationic lipid is saturated. Alternatively, the DNA may be added prior to the extrusion step and the above procedure followed.

The resulting DNA coated liposomes are then dried and gas instilled to create DNA-containing gas-filled liposomes. The resulting liposomes are then exposed to continuous wave ultrasound and tested for rupturing by reflectivity and absorbance on ultrasound.

Sound can be used to release the genetic material whether the DNA is entrapped within or on the outside of the gas-filled microsphere. Incorporation of the DNA on the outside of the gas-filled microsphere may allow more space for packaging gas within the microsphere. By making an effectively larger diameter, the microsphere will generally be more effective at utilizing the sound energy to release the genetic material.

It is believed that cationic lipids binding DNA provide an advantage, for example, since once sonic energy has disrupted the membrane of the liposome, the hydrophobic groups help the DNA to integrate into cells aiding passage through cell membranes and subcellular compartments.

The cationic lipids described above also have an advantage of neutralizing the negative charge of DNA and amphipathicity. When these cationic lipids are released from the liposomes, since the lipids are amphiphilic and the cell membrane is soluble, they tend to facilitate passage of the DNA into cells as well as through subcellular compartments.

Example 3

Liposomes composed of a 1:2 molar ratio of DOTMA and DPPC are prepared and coated with DNA encoding an HLA (major histocompatibility complex) gene, HLA-B7. The DNA-coated liposomes are injected intravenously into a patient with metastatic melanoma involving the soft tissues. Continuous wave 1.0 megahertz ultrasound energy is applied to the soft tissues so that the HLA-B7 DNA accumulates in the tumor. It is believed that some of the tumor cells would then transfected by the HLA-B7 gene, resulting in an immune response which may stimulate the patient's T cells to reject the tumor.

Example 4

Anti-sense oligonucleotides to the Ras oncogene are entrapped within liposomes composed of polyethyleneglycol-dipalmitoylphosphatidylethanolamine. These liposomes are injected i.v. in a patient with metastatic colon cancer. Continuous wave 1.0 megahertz ultrasound energy is applied to the metastases.

Example 5

Gas-filled microspheres are made as described above using egg phosphatidylcholine and DOTMA, N-[1-(2,3-dioleoyloxy)propyl]-N,N,N-trimethylammoium chloride, to bind YAC expression vectors carrying the dystrophin gene. The microspheres are injected i.v. into a patient with Duchenne's Muscular Dystrophy (or Becker's MD). Continuous wave 1.0 megahertz ultrasound energy is applied to the muscle tissue of the patient and may result in an increase in muscular strength and mass.

Example 6

The CFTR (Cystic Fibrosis transmembrane conductance regulator) gene on a YAC expression vector is entrapped within a micellar formulation of microspheres entrapping argon gas bearing cationic lipids in a 1:1 molar composition with DPPC. The microspheres are injected i.v. into a patient with Cystic Fibrosis and sonic energy is applied to the affected tissues (e.g., lungs, pancreas, etc.). Patients may show a reduction in mucus accumulation in the lungs and improved functioning of the other affected organs.

Example 7

Cationic microspheres containing DNA encoding the gene for Interleukin-2 (IL-2) are injected into a patient with metastatic renal cancer. A cancerous growth in the patient's abdomen is scanned with ultrasound. The backscatter from the tumor and spectral harmonic signatures of the ultrasound echoes would increase in the tumor as the microspheres accumulate in the tumor. The ultrasound power, pulse duration and pulse repetition are increased until the point at which the spectral ultrasound signature of the gas-filled microspheres disappears from the tumor. By carefully controlling the power, as detected by a hydrophone, cavitation is controlled. The treatment may result in transfection of some of the tumor cells with the gene for IL-2. T-cell lymphocytes may then respond to the cytokine and infiltrate and destroy the tumor.

Example 8

Cationic microspheres delivering DNA encoding the gene for Tumor Necrosis Factor (TNF) are injected into a patient with metastatic renal cancer. A cancerous growth in the patient's abdomen is scanned with ultrasound. The backscatter from the tumor and spectral harmonic signatures of the ultrasound echoes would increase in the tumor as the microspheres accumulate in the tumor. The ultrasound power, pulse duration and pulse repetition are increased until the point at which the spectral ultrasound signature of the gas-filled microspheres disappears from the tumor. By carefully controlling the power, as detected by a hydrophone, cavitation is controlled. The treatment may result in transfection of some of the tumor cells with the gene for TNF. The tumor may then begin to produce TNF locally and massive coagulative necrosis may result.

Example 9

Microspheres composed of dipalmitoylphosphotidylcholine and cationic lipids binding DNA are constructed with alkylated derivatives of anti-tumor monoclonal antibodies. In a patient with metastatic melanoma, microspheres coated with anti-melanoma antigen monoclonal antibody and containing Interleukin-2 are injected i.v. The patient is scanned by diagnostic ultrasound. Tumorous deposit within the soft tissues are highlighted by the reflective, gas-filled microspheres. As these nodes are detected by diagnostic ultrasound, the power of the ultrasound is increased to 5 watts and focussed on the metastatic deposits containing the tumor. As the power is delivered, the tumors are monitored ultrasonographically. When all of the high frequency spectral signatures reflecting tumor localized microspheres disappears within a given region of tumor, the sound energy is then focussed on a new area of tumor with sonographic spectral signatures indicating microspheres.

Example 10

Cationic gas-filled liposomes with three types of surface-bound antisense DNAs are synthesized as described above. The antisense DNAs are targeted against genes encoding c-myc, c-myb, smooth muscle growth factor, and endothelial cell growth factor. The gas-filled liposomes are administered intra-arterially to an angioplasty site. 5 megahertz of continuous wave ultrasound is then applied to the angioplasty site. It is believed that the release of the antisense RNAs upon rupture of the microspheres will cause improved endothelialization and decreased propensity to clotting.

Example 11

Dipalmitoylphosphatidylcholine (1 gram) is suspended in 10 ml phosphate buffered saline containing the drug adriamycin, the suspension is heated to about 50° C., and then is swirled by hand in a round bottom flask for about 30 minutes. The heat source is removed, and the suspension is swirled for two additional hours, while allowing the suspension to cool to room temperature, to form drug containing liposomes.

The liposomes thus prepared are placed in a vessel in an apparatus similar to that shown in FIG. 14, cooled to about −10° C., and are then subjected to high negative vacuum pressure. The temperature of the liposomes is then raised to about 10° C. High negative vacuum pressure is maintained for about 48 hours. After about 48 hours, nitrogen gas is gradually instilled into the chamber over a period of about 4 hours after which time the pressure is returned to ambient pressure. The resulting drug containing vacuum dried gas instilled liposomes, the gas-filled liposomes being substantially devoid of any liquid in the interior thereof, are then suspended in 10 cc of phosphate buffered saline and vortexed for 10 minutes, and then stored at about 4° C. for about three months.

Example 12

To test the liposomes of Example 11 ultrasono-graphically, a 250 mg sample of these liposomes is suspended in 300 cc of non-degassed phosphate buffered saline. The liposomes are then scanned in vitro at varying time intervals with a 7.5 mHz transducer using an Acoustic Imaging Model 5200 scanner (Acoustic Imaging, Phoenix, Ariz.) and employing the system test software to measure dB reflectivity. The system is standardized prior to testing the liposomes with a phantom of known acoustic impedance. Good dB reflectivity of the liposomes is shown.

Example 13

Dipalmitoylphosphatidylcholine (1 gram) and the cryoprotectant trehalose (1 gram) are suspended in 10 ml phosphate buffered saline containing the drug amphotericin-B, the suspension is heated to about 50° C., and then is swirled by hand in a round bottom flask for about 30 minutes. The heat source is removed, and the suspension is swirled for about two additional hours, while allowing the suspension to cool to room temperature, to form liposomes.

The liposomes thus prepared are then vacuum dried and gas instilled, substantially following the procedures shown in Example 11, resulting in drug containing vacuum dried gas instilled liposomes, the gas-filled liposomes being substantially devoid of any liquid in the interior thereof. The liposomes are then suspended in 10 cc of phosphate buffered saline and vortexed, and then stored at about 4° C. for several weeks. Prior to use, the gas-filled liposomes are extruded through a 10 μm polycarbonate filter (Nuclepore, Costar, Pleasanton, Calif.) by injection through a syringe with a filter attached to the hub.

Example 14

To test the liposomes of Example 13 ultrasono-graphically, the procedures of Example 12 are substantially followed. Good dB reflectivity of the liposomes is shown.

Example 15

Dipalmitoylphosphatidylcholine (1 gram) is suspended in 10 ml phosphate buffered saline containing the drug cytosine arabinosine, the suspension is heated to about 50° C., and then swirled by hand in a round bottom flask for about 30 minutes. The suspension is then subjected to 5 cycles of extrusion through an extruder device jacketed with a thermal barrel (Extruder Device™, Lipex Biomembranes, Vancouver, Canada), both with and without conventional freeze-thaw treatment prior to extrusion, while maintaining the temperature at about 50° C. The heat source is removed, and the suspension is swirled for about two additional hours, while allowing the suspension to cool to room temperature, to form liposomes.

The liposomes thus prepared are then vacuum dried and gas instilled, substantially following the procedures shown in Example 11, resulting in drug containing vacuum dried gas instilled liposomes, the gas-filled liposomes being substantially devoid of any liquid in the interior thereof. The liposomes are then suspended in 10 cc of phosphate buffered saline, and then stored at about 4° C. for several weeks.

Example 16

To test liposomes of Example 15 ultrasono-graphically, the procedures of Example 12 are substantially followed. Good dB reflectivity of the liposomes is shown.

Example 17

In order to test the stability of the drug containing liposomes of the invention, the liposomes suspension of Example 11 are passed by hand through a 10 micron polycarbonate filter in a syringe as shown in FIG. 10. After extrusion treatment, the liposomes are studied ultrasonographically, as described in Example 12. Surprisingly, even after extrusion, the liposomes of the invention substantially retain their echogenicity.

Example 18

The liposomes of Example 11 are scanned by ultrasound using transducer frequencies varying from 3 to 7.5 mHz. The results indicate that at a higher frequency of ultrasound, the echogenicity decays more rapidly, reflecting a relatively high resonant frequency and higher energy associated with the higher frequencies.

Example 19

A patient with cancer is given an intravenous drug containing vacuum dried gas instilled liposomes, the gas-filled liposomes being substantially devoid of any liquid in the interior thereof. The drug contained in the liposomes is adriamycin. As the intravenous injection is administered, the tumor is scanned ultrasonographically and via an automated software program, and the resonant frequency of the liposomes is determined. Ultrasonic energy is then focused into the tumor at the peak resonant frequency of the liposomes. The amount of ultrasonic energy is insufficient to cause any appreciable tissue heating (that is, no change in temperature greater than 2° C.), however, this energy is sufficient to cause the liposomes to pop and release the adriamycin at the tumor site. In so doing, local drug delivery is accomplished using the liposomes with ultrasound.

Example 20

In a patient with a severe localized fungal infection, drug containing vacuum dried gas instilled liposomes, the gas-filled liposomes being substantially devoid of any liquid in the interior thereof, are injected intravenously and ultrasound is used in a fashion substantially similar to that described in Example 19 to accomplish local drug delivery. The drug amphotericin-B, which the liposomes contain, is effectively delivered to the site of the infection.

Example 21

In order to prepare gas-filled liposomes, fifty mg of 1,2-Dipalmitoyl-Sn-Glycero-3-Phosphocholine (MW: 734.05, powder, Lot No. 160pc-183) (Avanti-Polar Lipids, Alabaster, Ala.) was weighed and hydrated with 5.0 ml of saline solution (0.9% NaCl) or phosphate buffered saline (0.8% sodium chloride, 0.02% potassium chloride, 0.115% dibasic sodium phosphate and 0.02% monobasic potassium phosphate, pH adjusted to 7.4) in a centrifuge tube. The hydrated suspension was then shaken on a vortex machine (Scientific Industries, Bohemia, N.Y.) for 10 minutes at an instrument setting of 6.5. A total volume of 12 ml was then noted. The saline solution decreased from 5.0 ml to about 4 ml.

The gas-filled liposomes made via this new method were then sized by optical microscopy. It was determined that the largest size of the liposomes ranged from about 50 to about 60 µm and the smallest size detected was about 8 µm. The average size ranged from about 15 to about 20 µm.

The gas-filled liposomes were then filtered through a 10 or 12 µm "NUCLEPORE" membrane using a Swin-Lok Filter Holder, ("NUCLEPORE" Filtration Products, Costar Corp., Cambridge, Mass.) and a 20 cc syringe (Becton Dickinsion & Co., Rutherford, N.J.). The membrane was a 10 or 12 µm "NUCLEPORE" membrane (Nuclepore Filtration Products, Costar Corp., Cambridge, Mass.). The 10.0 µm filter was placed in the SwinLok Filter Holder and the cap tightened down securely. The liposome solution was shaken up and it was transferred to the 20 cc syringe via an 18 gauge needle. Approximately 12 ml of liposome solution was placed into the syringe, and the syringe was screwed onto the Swin-Lok Filter Holder. The syringe and the filter holder assembly were inverted so that the larger of the gas-filled liposomes vesicles could rise to the top. Then the syringe was gently pushed up and the gas-filled liposomes were filtered in this manner.

The survival rate (the amount of the gas-filled liposomes that were retained after the extrusion process) of the gas-filled liposomes after the extrusion through the 10.0 µm filter was about 83–92%. Before hand extrusion, the volume of foam was about 12 ml and the volume of aqueous solution was about 4 ml. After hand extrusion, the volume of foam was about 10–11 ml and the volume of aqueous solution was about 4 ml.

The optical microscope was used again to determine the size distribution of the extruded gas-filled liposomes. It was determined that the largest size of the liposomes ranged from about 25 to about 30 µm and the smallest size detected was about 5 µm. The average size ranged from about 8 to about 15 µm.

It was found that after filtering, greater than 90% of the gas-filled liposomes were smaller than 15 µm.

Example 22

Fifty mg of 1,2-Dipalmitoyl-sn-Glycero-3-Phosphocholine, (MW: 734.05, powder) (Avanti-Polar Lipids, Alabaster, Ala.) was weighed and placed into a centrifuge tube. The lipid was then hydrated with 5.0 ml of saline solution (0.9% NaCl). The lipid was then vortexed for 10 minutes at an instrument setting of 6.5. After vortexing, the entire solution was frozen in liquid nitrogen. Then the sample was put on the lyophilizer for freeze drying. The sample was kept on the lyophilizer for 18 hours. The dried lipid was taken off the lyophilizer and rehydrated in 5 ml of saline solution and vortexed for ten minutes at a setting of 6.5. A small sample of this solution was pipetted onto a slide and the solution was viewed under a microscope. The size of the gas-filled liposomes was then determined. It was determined that the largest size of the liposomes was about 60 µm and the smallest size detected was about 20 µm. The average size ranged from about 30 to about 40 µm.

Example 23

Fifty mg of 1,2-Dipalmitoyl-Sn-Glycero-3-Phosphocholine (MW: 734.05, powder) (Avanti-Polar Lipids, Alabaster, Ala.) was weighed and placed into a centrifuge tube. Approximately two feet of latex tubing (0.25 in. inner diameter) was wrapped around a conical centrifuge tube in a coil-like fashion. The latex tubing was then fastened down to the centrifuge tube with electrical tape. The latex tubing was then connected to a constant temperature circulation bath (VWR Scientific Model 1131). The temperature of the bath was set to 60° C. and the circulation of water was set to high speed to circulate through the tubing. A thermometer was placed in the lipid solution and found to be between 42° and 50° C., which is above the phase transition temperature of the lipid.

The lipid solution was vortexed for a period of 10 minutes at a vortex instrument setting of 6.5. It was noted that very little foaming of the lipid (phase transition temp. =41° C.) did not appreciably form gas-filled liposomes. Optical microscopy revealed large lipidic particles in the solution. The number of gas-filled liposomes that formed at this temperature was less than 3% of the number that form at a temperature below the phase transition temperature. The solution was allowed to sit for 15 minutes until the solution temperature equilibrated to room temperature (25° C.). The solution was then vortexed for a duration of 10 minutes. After 10 minutes, it was noted that gas-filled liposomes formed.

Example 24

50 mg of 1,2-Dipalmitoyl-Sn-Glycero-3-Phosphocholine (MW: 734.05, powder) (Avanti-Polar Lipids, Alabaster, Ala.) was weighed and placed into a centrifuge tube. The lipid was then hydrated with 5.0 ml of 0.9% NaCl added. The aqueous lipid solution was vortexed for 10 minutes at an instrument setting of 6.5. After vortexing, the entire solution was frozen in liquid nitrogen. The entire solution was then thawed in a water bath at room temperature (25° C.). The freeze thaw procedure was then repeated eight times. The hydrated suspension was then vortexed for 10 minutes at an instrument setting of 6.5. Gas-filled liposomes were then detected as described in Example 21.

Example 25

Two centrifuge tubes were prepared, each having 50 mg of DPPC. 1 mol % (~0.2 mg of Duponol C lot No. 2832) of sodium lauryl sulfate, an emulsifying agent, was added to one of the centrifuge tubes, and the other tube received 10 mol % (2.0 mg of Duponol C lot No. 2832). Five ml of 0.9% NaCl was added to both centrifuge tubes. Both of the tubes were frozen in liquid nitrogen and lyophilized for approximately 16 hours. Both samples were removed from the lyophilizer and 5 ml of saline was added to both of the tubes. Both of the tubes were vortexed at position 6.5 for 10 minutes.

It was determined that the largest size of the gas-filled liposomes with 1 mol % of sodium lauryl sulfate was about 75 μm and the smallest size detected was about 6 μm. The average size ranged from about 15 to about 40 μm. It was determined that the largest size of the gas-filled liposomes with 10 mol % of sodium lauryl sulfate was about 90 μm and the smallest size detected was about 6 μm. The average size ranged from about 15 to about 35 μm.

The volume of foam in the solution containing gas-filled liposomes with 1 mol % sodium lauryl sulfate was about 15 ml and the volume of aqueous solution was about 3–4 ml. The volume of foam in the solution containing gas-filled liposomes with 10 mol % sodium lauryl sulfate was also about 15 ml and the volume of aqueous solution was about 3–4 ml.

Example 26

This example determined whether sonication could be used to create gas-filled liposomes. 50 mg of lipid, 1,2-Dipalmitoyl-Sn-Glycero-3-Phosphocholine (Avanti-Polar Lipids, Alabaster, Ala.), was weighed out and hydrated with 5 ml of 0.9% NaCl. Instead of vortexing, the aqueous solution was sonicated using a Heat Systems Sonicator Ultrasonic Processor XL (Heat Systems, Inc., Farmingdale, N.Y.) Model XL 2020. The sonicator, with a frequency of 20 KHz, was set to continuous wave, at position 4 on the knob of the sonicator. A micro tip was used to sonicate for 10 minutes. Following sonication, the solution was viewed under an optical microscope. There was no evidence of gas-filled liposomes having been produced.

Next, the micro tip of the sonicator was removed and replaced with the end cap that was supplied with the sonicator. Another solution (50 mg of lipid per 5 ml of saline) was prepared and sonicated with this tip. After 10 minutes, the solution was viewed under the microscope. Again, there was no evidence of gas-filled liposomes.

Example 27

This example determined whether a lower concentration limit of the lipid would halt the production of gas-filled liposomes. Ten mg of 1,2-Dipalmitoyl-Sn-Glycero-3-Phosphocholine (Avanti-Polar Lipids, Alabaster, Ala.) was added to 10 ml of saline solution (0.9% w:v NaCl). The lipid/saline solution was vortexed at position 6.5 for 10 minutes. The solution was viewed under an optical microscope for sizing. It was determined that the largest size of the liposomes ranged from about 30 to about 45 μm and the smallest size detected was about 7 μm. The average size ranged from about 30 to about 45 μm.

It appeared that the gas-filled liposomes were more fragile as they appeared to burst more rapidly than previously shown. Thus, it appears that concentration of the lipid is a factor in the generation and stability of gas-filled liposomes.

Example 28

Unfiltered gas-filled liposomes were drawn into a 50 ml syringe and passed through a cascade of a "NUCLEPORE" 10 μm filter and 8 μm filter that are a minimum of 150 μm apart, as illustrated in FIGS. 11 and 12. Alternatively, for example, the sample may be filtered through a stack of 10 μm and 8 μm filters that are immediately adjacent to each other. Gas-filled liposomes were passed through the filters at such a pressure whereby the flow rate was 2.0 ml min$^{-1}$. The subsequently filtered gas-filled liposomes were then measured for yield of gas-filled lipid microspheres which resulted in a volume of 80–90% of the unfiltered volume.

The resulting gas-filled liposomes were sized by four different methods to determine their size and distribution. Sizing was performed on a Particle Sizing Systems Model 770 Optical Sizing unit, a Zeiss Axiplan optical microscope interfaced to image processing software manufactured by Universal Imaging, and a Coulter Counter (Coulter Electronics Limited, Luton, Beds., England). As can be seen in FIGS. 15A, 15B, 16A, and 16B the size of the gas-filled liposomes were more uniformly distributed around 8–10 μm as compared to the unfiltered gas-filled liposomes. Thus, it can be seen that the filtered gas-filled liposomes are of much more uniform size.

Example 29

250 mg DPPC (dipalmitoylphosphatidylcholine) and 10 ml of 0.9% NaCl were added to a 50 ml Falcon centrifuge tube (Becton-Dickinson, Lincoln Park, N.J.) and maintained at an ambient temperature (approx. 20° C.). The suspension was then extruded through a 1 μm "NUCLEPORE" (Costar, Pleasanton, Calif.) polycarbonate membrane under nitrogen pressure. The resultant suspension was sized on a Particle Sizing Systems (Santa Barbara, Calif.) Model 370 laser light scattering sizer. All lipid particles were 1 μm or smaller in mean outside diameter.

In addition, the same amount of DPPC suspension was passed five times through a Microfluidics™ (Microfluidics Corporation, Newton, Mass.) microfluidizer at 18,000 p.s.i. The suspension, which became less murky, was sized on a Particle Sizing Systems (Santa Barbara, Calif.) Sub Micron Particle Sizer Model 370 laser light scattering sizer where it was found that the size was uniformly less than 1 μm. The particle size of microfluidized suspensions is known to remain stable up to six months.

Example 30

100 mg DSPC (distearoylphosphatidylcholine) and 10 ml of 0.9% NaCl were added to a 50 ml Falcon centrifuge tube (Becton-Dickinson, Lincoln Park, N.J.). The suspension was then extruded through a 1 μm "NUCLEPORE" (Costar, Pleasanton, Calif.) polycarbonate membrane under nitrogen pressure at 300–800 p.s.i. The resultant suspension was sized on a Particle Sizing Systems (Santa Barbara, Calif.) Sub Micron Particle Sizer Model 370 laser light scattering sizer. It was found that all particles were 1 μm or smaller in size.

In addition, the same amount of DPPC suspension was passed five times through a Microfluidics™ (Microfluidics Corporation, Newton, Mass.), microfluidizer at 18,000 p.s.i. The resultant suspension, which was less murky, was sized on a Sub Micron Particle Sizer Systems Model 370 laser light scattering sizer and it was found that the size was uniformly less than 1 μm.

Example 31

The previously sized suspensions of DPPC and DSPC of Examples 29 and 30 were subjected to autoclaving for twenty minutes on a Barnstead Model C57835 autoclave (Barnstead/Thermolyne, Dubuque, Iowa). After equilibration to room temperature (approx. 20° C.), the sterile suspension was used for gas instillation.

Example 32

10 ml of a solution of 1,2-dipalmitoyl-phosphatidylcholine at 25 mg/ml in 0.9% NaCl, which had previously been extruded through a 1 μm filter and autoclaved for twenty minutes, was added to a Falcon 50 ml centrifuge tube (Becton-Dickinson, Lincoln Park, N.J.). After equilibration of the lipid suspension to room temperature (approximately 20° C.), the liquid was vortexed on a VWR Genie-2 (120 V, 0.5 amp, 60 Hz.) (Scientific Industries, Inc., Bohemia, N.Y.) for 10 minutes or until a time that the total volume of gas-filled liposomes was at least double or triple the volume of the original aqueous lipid solution. The solution at the bottom of the tube was almost totally devoid of anhydrous particulate lipid, and a large volume of foam containing gas-filled liposomes resulted. Thus, prior autoclaving does not affect the ability of the lipid suspension to form gas-filled liposomes. Autoclaving does not change the size of the liposomes, and it does not decrease the ability of the lipid suspensions to form gas-filled liposomes.

Example 33

10 ml of a solution of 1,2-dipalmitoyl-phosphatidylcholine at 25 mg/ml in 0.9% NaCl, which had previously been extruded through a 1 μm filter and autoclaved for twenty minutes, was added to a Falcon 50 ml centrifuge tube (Becton-Dickinson, Lincoln Park, N.J.). After equilibration of the lipid suspension to room temperature (approximately 20° C.), the tube was then placed upright on a VWR Scientific Orbital shaker (VWR Scientific, Cerritos, Calif.) and shaken at 300 r.p.m. for 30 minutes. The resultant agitation on the shaker table resulted in the production of gas-filled liposomes.

Example 34

10 ml of a solution of 1,2-dipalmitoyl-phosphatidylcholine at 25 mg/ml in 0.9% NaCl, which had previously been extruded through a 1 μm filter and autoclaved for twenty minutes, was added to a Falcon 50 ml centrifuge tube (Becton-Dickinson, Lincoln Park, N.J.). After equilibration of the lipid suspension to room temperature (approximately 20° C.), the tube was immobilized inside a 1 gallon empty household paint container and subsequently placed in a mechanical paint mixer employing a gyrating motion for 15 minutes. After vigorous mixing, the centrifuge tube was removed, and it was noted that gas-filled liposomes had formed.

Example 35

10 ml of a solution of 1,2-dipalmitoyl-phosphatidylcholine at 25 mg/ml in 0.9% NaCl, which had previously been extruded through a 1 μm nuclepore filter and autoclaved for twenty minutes, was added to a Falcon 50 ml centrifuge tube (Becton-Dickinson, Lincoln Park, N.J.). After equilibration of the lipid suspension to room temperature (approximately 20° C.), the tube was shaken forcefully by hand for ten minutes. Upon ceasing agitation, gas-filled liposomes were formed.

Example 36

Gas-filled liposomes were produced from DPPC as described in Example 32. The resultant unfiltered liposomes were drawn into a 50 ml syringe and passed through a cascade filter system consisting of a "NUCLEPORE" (Costar, Pleasanton, Calif.) 10 μm filter followed by an 8 μm filter spaced a minimum of 150 μm apart. In addition, on a separate sample, a stacked 10 μm and 8 μm filtration assembly was used, with the two filters adjacent to one another. Gas-filled liposomes were passed through the filters at a pressure such that they were filtered a rate of 2.0 ml/min. The filtered gas-filled liposomes yielded a volume of 80–90% of the unfiltered volume.

The resultant gas-filled liposomes were sized by four different methods to determine their size distribution. Sizing was performed on a Particle Sizing Systems (Santa Barbara, Calif.) Model 770 Optical Sizing unit, and a Zeiss (Oberkochen, Germany) Axioplan optical microscope interfaced to image processing software (Universal Imaging, West Chester, Pa.) and a Coulter Counter (Coulter Electronics Limited, Luton, Beds., England). As illustrated in FIG. 18A and 18B, the size of the gas-filled liposomes was more uniformly distributed around 8–10 μm as compared to the unfiltered gas-filled liposomes.

Various modifications of the invention in addition to those shown and described herein will be apparent to those skilled in the art from the foregoing description. Such modifications are also intended to fall within the scope of the appended claims.

What is claimed is:

1. A method for the controlled delivery of therapeutic compounds to a region of a patient comprising:
   (i) administering to the patient an aqueous suspension of gas-filled liposomes, said gas-filled liposomes comprising a therapeutic compound, and further comprising at least about 50% gas in the interior thereof;
   (ii) monitoring the liposomes using ultrasound to determine the presence of the liposomes in the region; and
   (iii) inducing the rupture of the liposomes using ultrasound to release the therapeutic compound in the region to achieve a therapeutic effect.

2. A method of claim 1 wherein the liposomes are administered intravenously.

3. A method of claim 1 wherein the liposomes are comprised of at least one lipid selected from the group consisting of dipalmitoylposphatidylcholine, dipalmitoylphosphatidylethanolamine, and a phosphatidic acid, and said liposomes further comprising polyethylene glycol.

4. A method of claim 1 wherein the liposomes are filled with a gas selected from the group consisting of air,nitrogen, carbon dioxide, oxygen, argon, xenon, helium, and neon.

5. A method of claim 4 wherein the liposomes are filled with nitrogen gas.

6. A method of claim 1 wherein said liposomes are stored suspended in an aqueous medium.

7. A method of claim 1 wherein the liposomes have a reflectivity of between about 2 dB and about 20 dB.

8. A method of claim 1 wherein the liposomes comprise gas-filled liposomes prepared by a vacuum drying gas installation method and having encapsulated therein a therapeutic compound.

9. A method of claim 1 wherein the liposomes comprise gas-filled liposomes prepared by a gel state shaking gas instillation method.

10. A method for the controlled delivery of a drug to an internal bodily region of a patient comprising:
   (a) administering to the patient an aqueous suspension of a drug delivery system comprising gas-filled liposomes prepared by a vacuum drying gas instillation method, said liposomes comprising at least about 90% gas in the interior thereof and having encapsulated therein a drug;

(b) monitoring the liposomes using ultrasound to determine the presence of said liposomes in the region; and (c) inducing the rupture of the liposomes using ultrasound to release the drugs in the region to achieve a therapeutic effect.

11. A method according to claim 10 wherein the drug is delivered in the area of the patient's left heart.

12. The method of claim 1 wherein liposomes are administered via a nebulizer.

13. The method of claim 12 wherein the liposomes are targeted to the lung.

14. The method of claim 13 wherein said therapeutic is antisense ras/p53.

15. The method of claim 1 wherein the liposomes are comprised of at least one dipalmitoyl lipid.

16. The method of claim 1 wherein said therapeutic compound is selected from the group consisting of carbohydrates, peptides, glycopeptides, glycolipids and lectins, said therapeutic compound incorporated into the surface of said liposomes.

17. The method of claim 1 wherein the liposomes comprise at least about 90% gas in the interior thereof.

* * * * *

UNITED STATES PATENT AND TRADEMARK OFFICE
CERTIFICATE OF CORRECTION

PATENT NO. : 5,580,575  Page 1 of 7
DATED : Unger et al.
INVENTOR(S) : Dec. 3, 1996

It is certified that error appears in the above-indentified patent and that said Letters Patent is hereby corrected as shown below:

On page 2, first column, under "References Cited" "U.S. PATENT DOCUMENTS", please delete "4,187,433" and insert --4,718,433-- therefor.

On page 2, first column, under "References Cited" "U.S. PATENT DOCUMENTS", at "4,544,545", please delete "Rayan et al." and insert --Ryan et al.-- therefor.

On page 2, first column, under "References Cited" "U.S. PATENT DOCUMENTS", at "4,895,719", please delete "Radhakvishnau" and insert --Radhakvishnan-- therefor.

On page 2, second column, under "References Cited" "OTHER PUBLICATIONS", at "Fitzpatrick", second line thereof, please delete "fo the" and insert --of the-- therefor.

On page 2, second column, under "References Cited" "OTHER PUBLICATIONS", at "Thanassi", first and second lines thereof, please delete "Decarboxylationand" and insert --Decarboxylation and-- therefor.

On page 2, second column, under "References Cited" "OTHER PUBLICATIONS", at "Nayar", second line thereof, please delete "Long-Chanin" and insert --Long-Chain-- therefor.

On page 2, second column, under "References Cited" "OTHER PUBLICATIONS", at "Nayar", second line thereof, please delete "Phosphtidylcholines" and insert --Phosphatidylcholines-- therefor.

UNITED STATES PATENT AND TRADEMARK OFFICE
CERTIFICATE OF CORRECTION

PATENT NO. : 5,580,575
DATED : Unger et al.
INVENTOR(S) : Dec. 3, 1996

It is certified that error appears in the above-indentified patent and that said Letters Patent is hereby corrected as shown below:

On page 2, second column, under "References Cited" "OTHER PUBLICATIONS", at "Mattrey", third line thereof, please delete "163 339-343." and insert --163:339-343.-- therefor.

On page 2, second column, under "References Cited" "OTHER PUBLICATIONS", at "Scarpa", second line thereof, please delete "Chmical" and insert --Chemical-- therefor.

On page 2, second column, under "References Cited" "OTHER PUBLICATIONS", at "Scarpa", second line thereof, please delete "Bilyares" and insert --Bilayers-- therefor.

On page 2, second column, under "References Cited" "OTHER PUBLICATIONS", at "Tilcock", first line thereof, please delete "Liposmal" and insert --Liposomal-- therefor.

On page 2, second column, under "References Cited" "OTHER PUBLICATIONS", at "Mann", first line thereof, please delete "IRon" and insert --Iron-- therefor.

On page 2, second column, under "References Cited" "OTHER PUBLICATIONS", at "Chapman", first line thereof, please delete "Phopholipids" and insert --Phospholipids" therefor.

UNITED STATES PATENT AND TRADEMARK OFFICE
CERTIFICATE OF CORRECTION

PATENT NO. : 5,580,575

DATED : Unger et al.

INVENTOR(S) : Dec. 3, 1996

Page 3 of 7

It is certified that error appears in the above-indentified patent and that said Letters Patent is hereby corrected as shown below:

On page 3, first column, under "References Cited" "OTHER PUBLICATIONS", at "Felgner", third line thereof, please delete "84:7413-74 17." and insert --84:7413-7417.-- therefor.

On page 3, first column, under "References Cited" "OTHER PUBLICATIONS", at "Gabizon", first line thereof, please delete "formlations" and insert --formulations-- therefor.

On page 3, first column, under "References Cited" "OTHER PUBLICATIONS", at "Kawai", third line thereof, please delete "4:1172'4 1174." and insert --4:1172-1174.-- therefor.

On page 3, second column, under "References Cited" "OTHER PUBLICATIONS", at "Simons", at the end of the third line thereof, please delete "ed".

On page 3, second column, under "References Cited" "OTHER PUBLICATIONS", please add the following reference which was omitted:

> --Crowe et al., "Preservation of Structural and functional Activity in Lyophilized Sarcoplasmic Reticulum", *Archives of Biochemistry and Biophysics* 1983, 220:477-484.--

In column 1, line 9, please delete "5,888,099" and insert --5,088,499-- therefor.

Figure 1B:
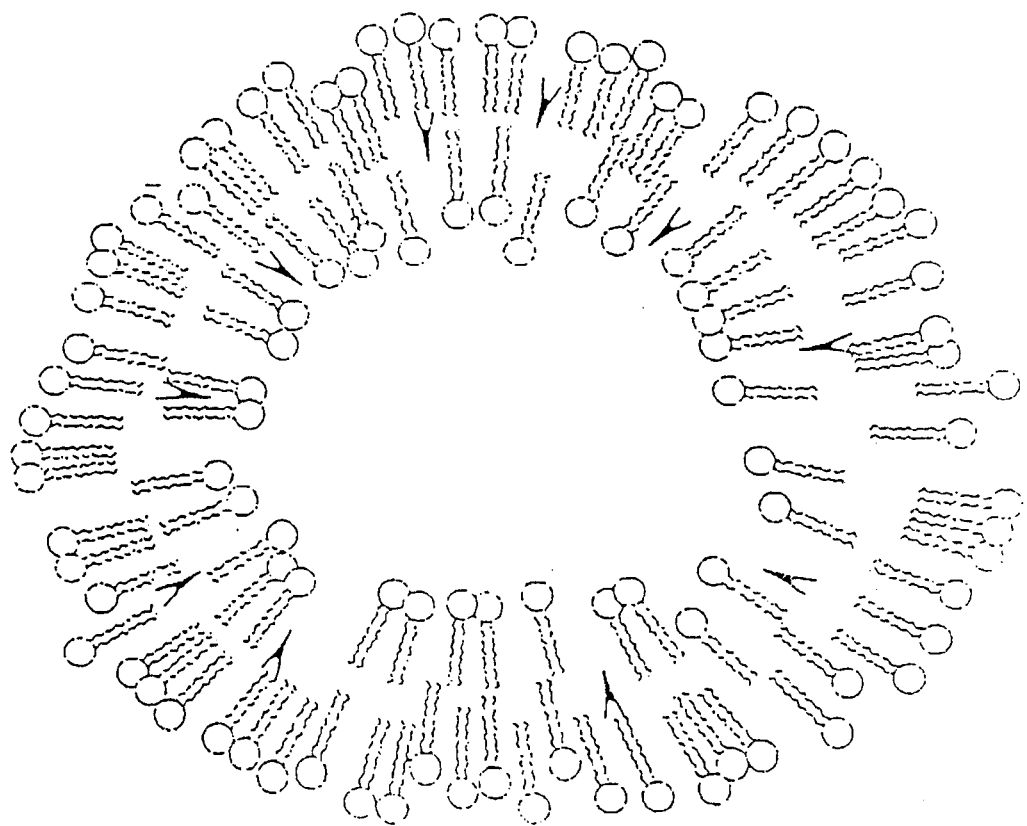
Figure 2A:
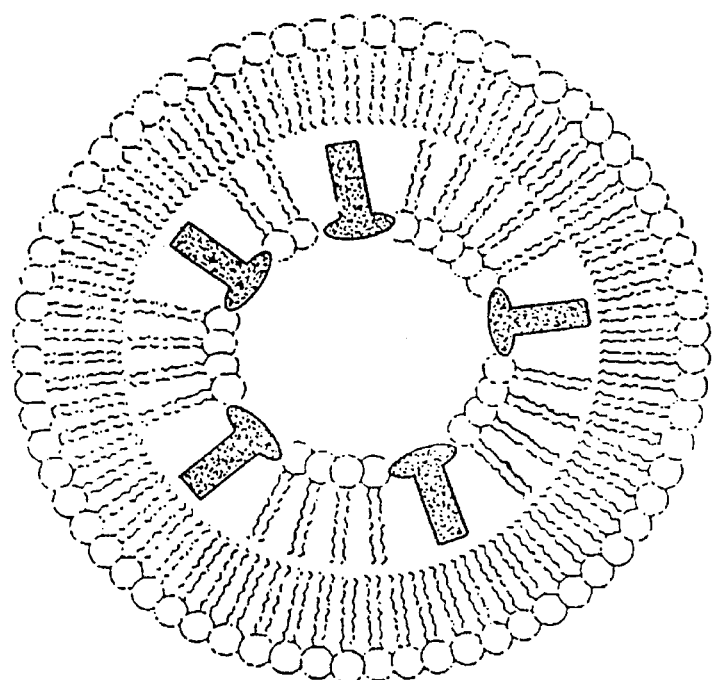
FIGS. 2A and 2B are diagrammactical depiction of two liposomes. The liposome of FIG. 2A is a gas-filled liposome having a therapeutic membrane bound aliphatic drug compound, indicated by the shaded members embedded within the inner layer of the wall of a liposome microsphere, and exposed to the gas-filled interior, and the liposome of FIG. 2B shows the subsequent release of the therapeutic upon the application of ultrasound.
Figure 2B:
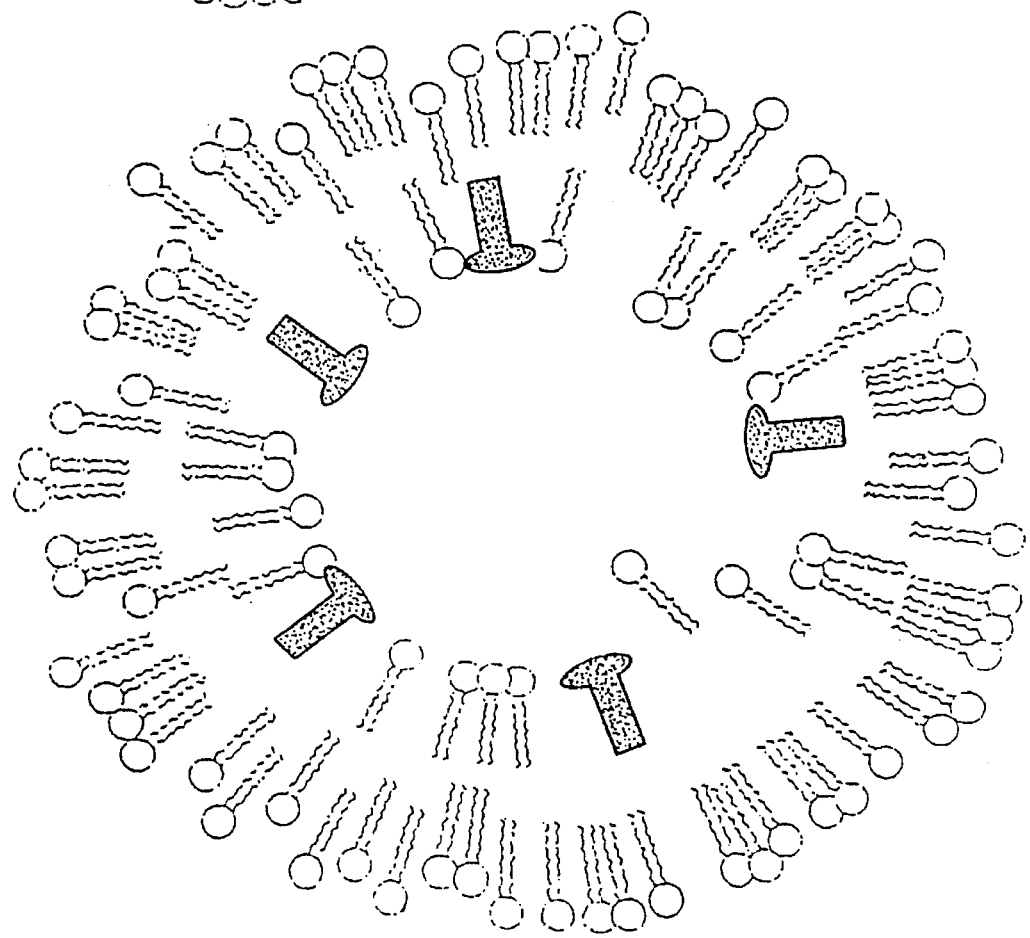
Figure 3A:
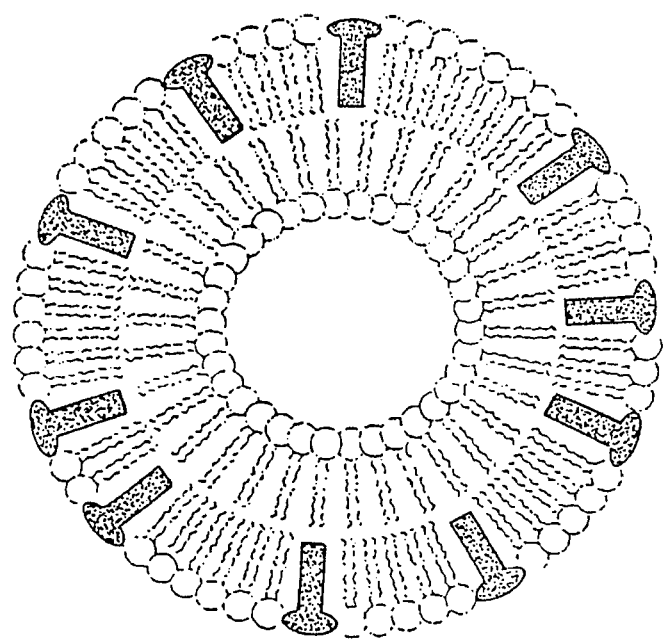
FIGS. 3A and 3B are diagrammatical illustrations of two liposomes. The liposome of FIG. 3A is a gas-filled liposome having a therapeutic membrane bound aliphatic drug compound, indicated by the shaded members embedded within the outer layer of the wall of a liposome microsphere, and exposed to the gas-filled interior, and the liposome of FIG. 3B shows the subsequent release of the therapeutic upon the application of ultrasound.
Figure 3B:
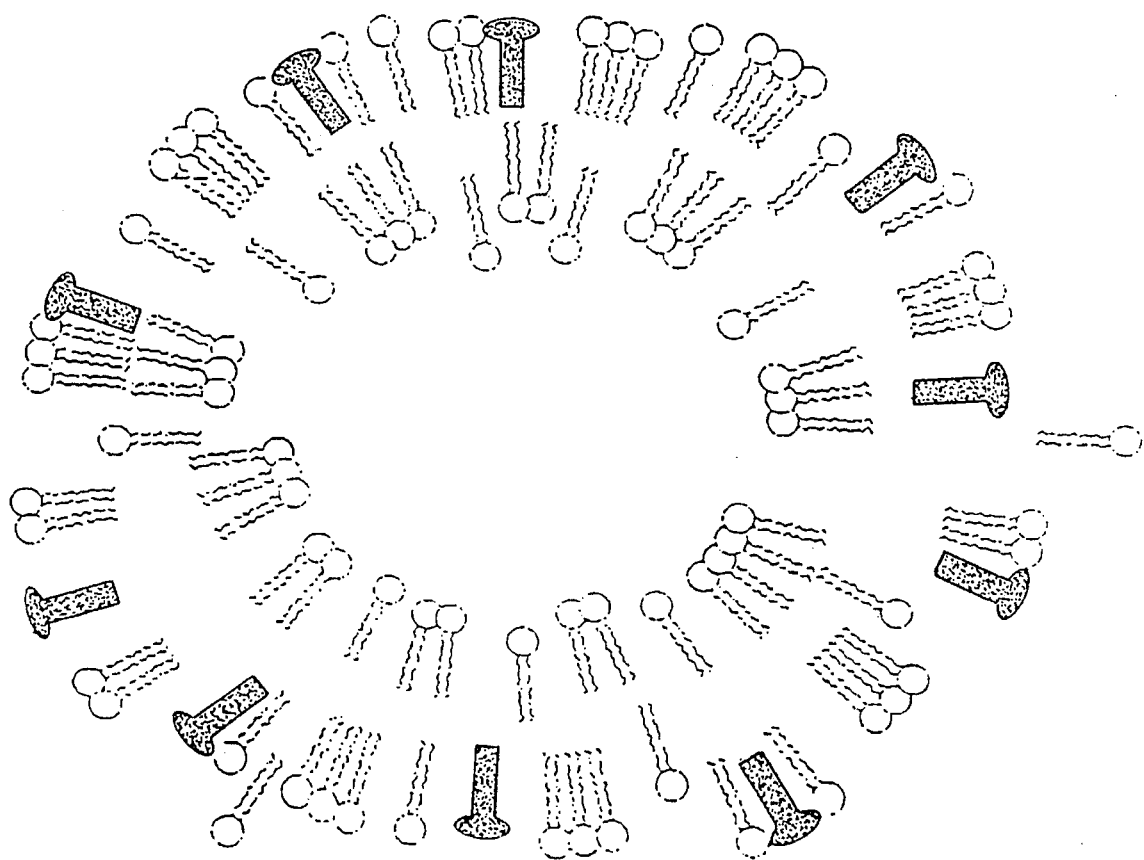
Figure 4A:
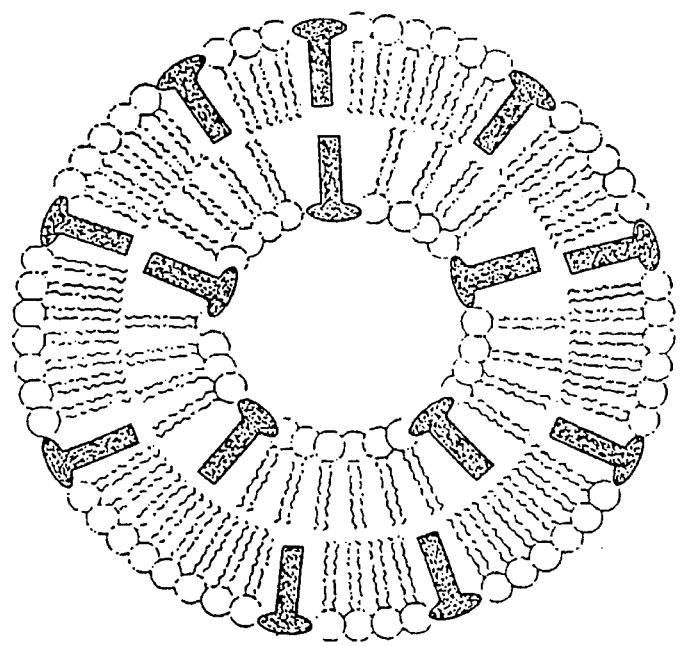
FIGS. 4A and 4B are diagrammactical representations of two liposomes. The liposome of FIG. 4A is a gas-filled liposome microsphere having a therapeutic membrane bound aliphatic drug compound, indicated by the shaded members embedded within the inner and outer layers of the wall of a liposome microsphere, and exposed to both the internal gas-filled void, and the exterior environment, and the liposome of FIG. 4B shows the subsequent release of the therapeutic upon the application of ultrasound.
Figure 4B:
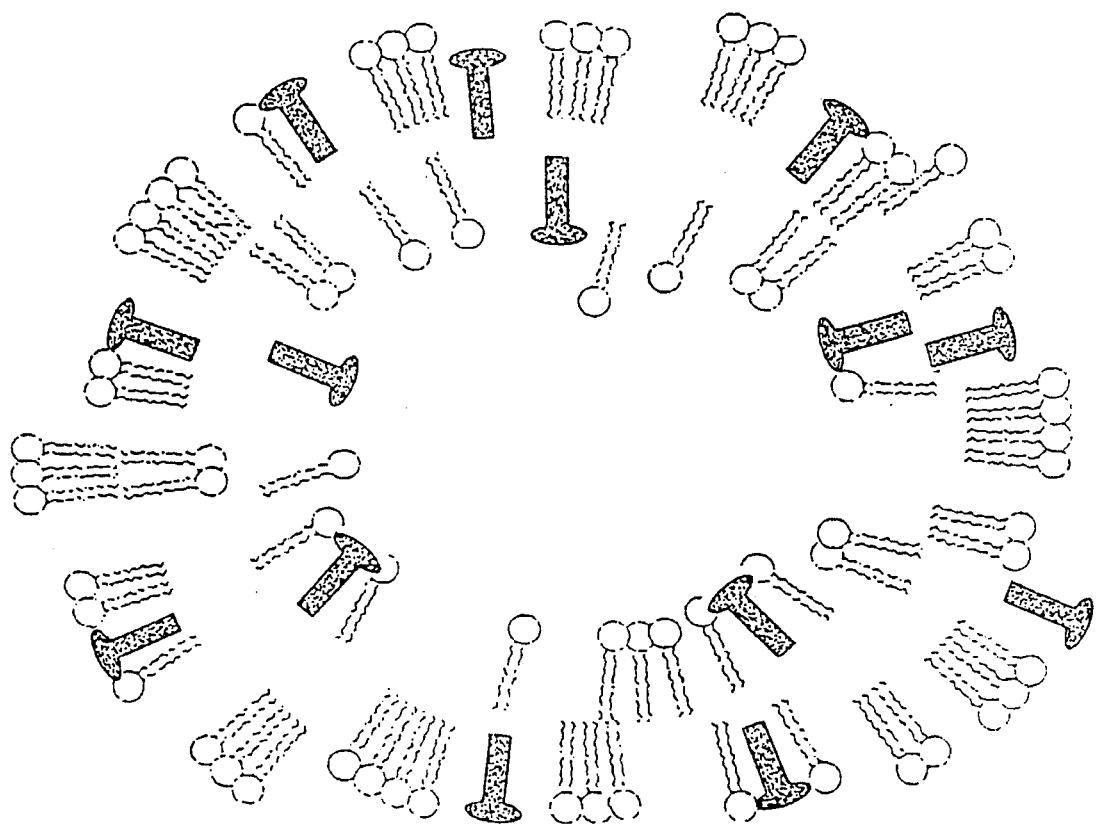
Figure 5A:
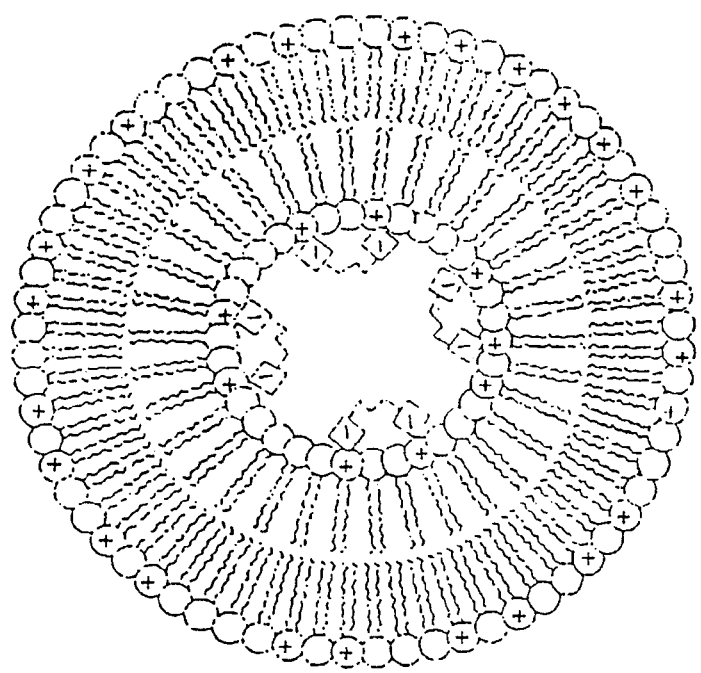
FIGS. 5A and 5B are diagrammatical depictions of two liposomes. The liposome of FIG. 5A is a gas-filled liposome microsphere having a therapeutic negatively charged drug compound, indicated by the minus signs enclosed in squares, attached to the interior of the liposome, and the liposome of FIG. 5B shows the subsequent release of the therapeutic upon the application of ultrasound.
Figure 5B:
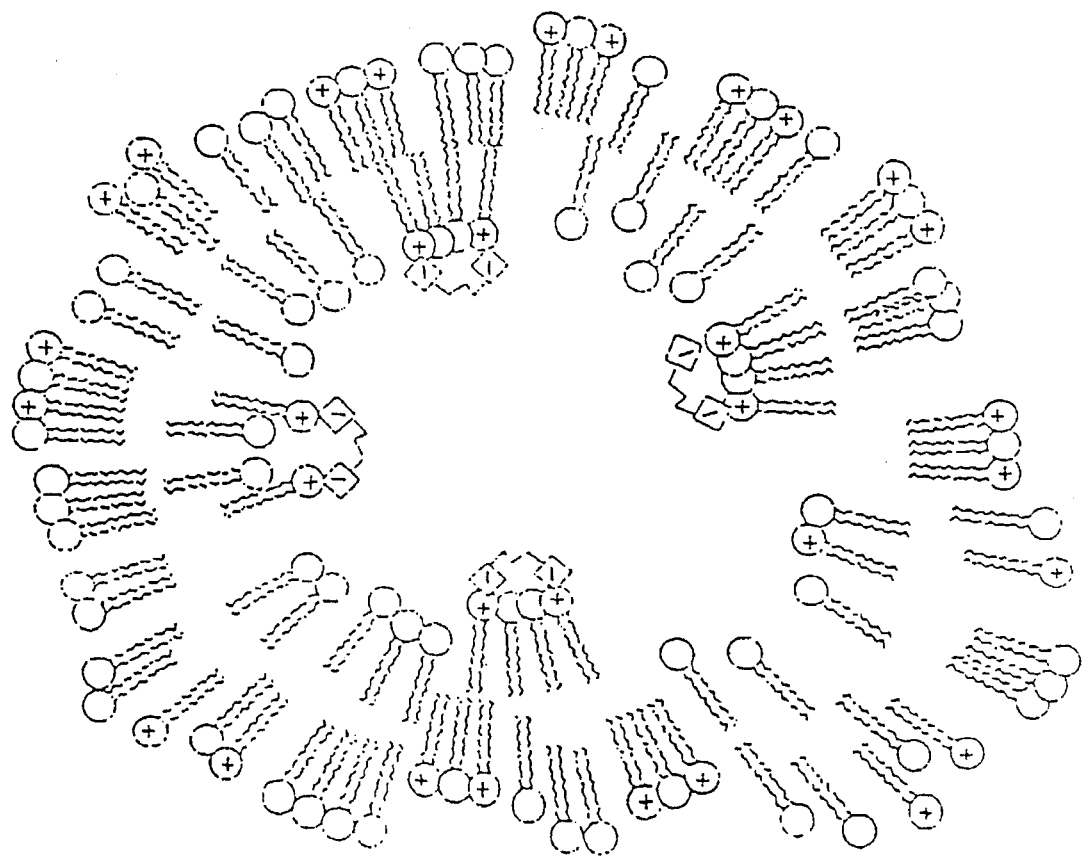
Figure 6A:
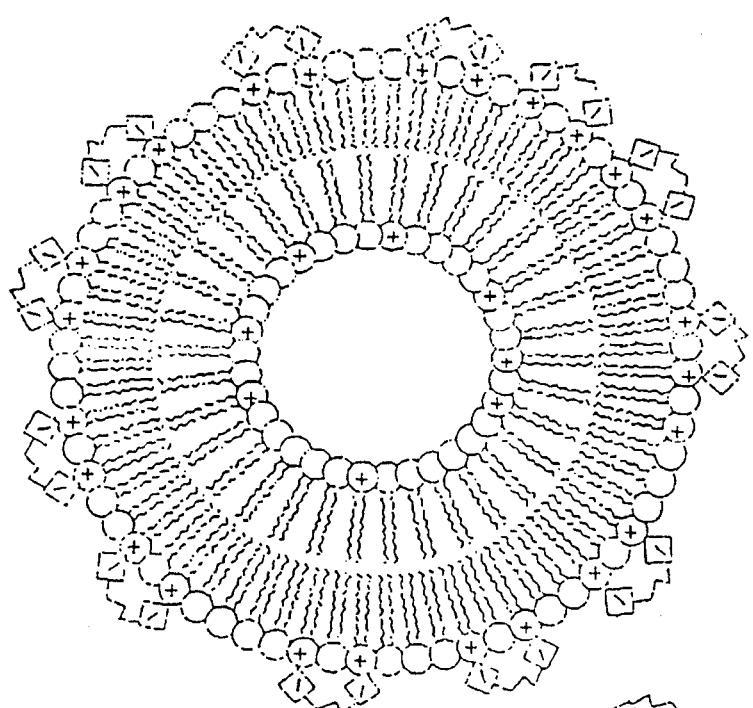
FIGS. 6A and 6B are diagrammatical depiictions of two liposomes. The liposome of FIG. 6A is a gas-filled liposome microsphere having a therapeutic negatively charged drug compound attached to the exterior of a liposome microsphere, and the liposome of FIG. 6B shows the subsequent release of the therapeutic upon the application of ultrasound.
Figure 6:
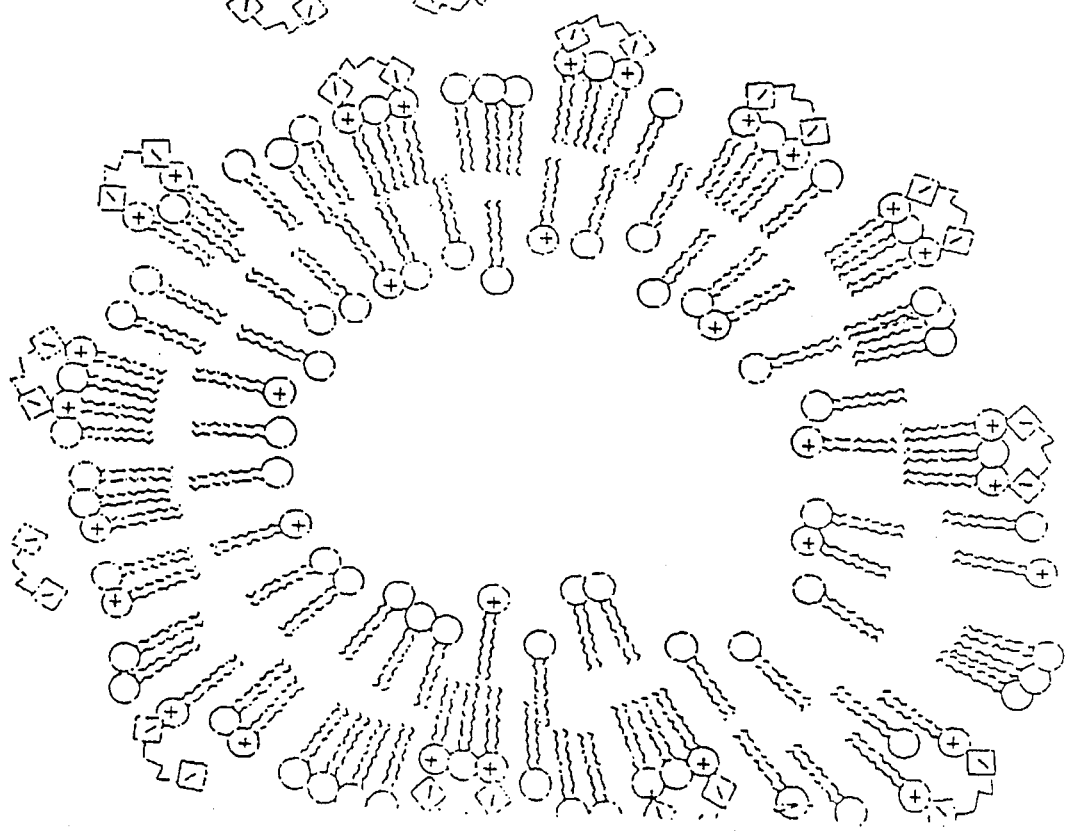

In column 2, line 62, after "liposome" and before "FIG. 1B", please insert --of--.

UNITED STATES PATENT AND TRADEMARK OFFICE
CERTIFICATE OF CORRECTION

PATENT NO. : 5,580,575
DATED : Unger et al.
INVENTOR(S) : Dec. 3, 1996

It is certified that error appears in the above-indentified patent and that said Letters Patent is hereby corrected as shown below:

In column 2, line 64, please delete "diagrammactical depiction" and insert --diagrammatical depictions-- therefor.

In column 3, line 13, please delete "diagrammactical" and insert --diagrammatical-- therefor.

In column 3, line 30, please delete "depiictions" and insert --depictions-- therefor.

In column 3, line 36, please delete "7A and 7B, 7C" and insert --7A, 7B, 7C,-- therefor.

In column 3, line 36, please delete "diagrammactical" and insert --diagrammatical-- therefor.

Figure 7A:
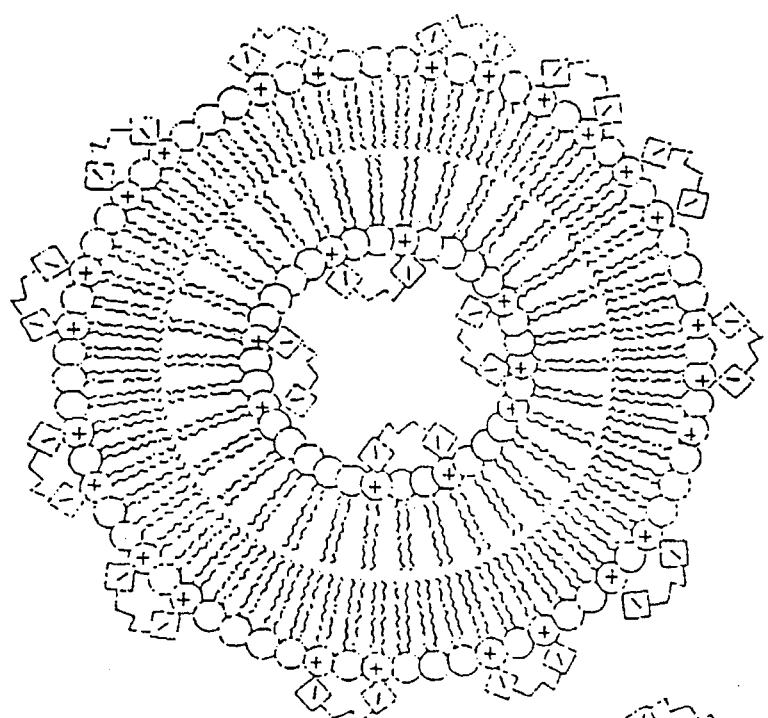
FIGS. 7A and 7B, 7C and 7D are diagrammactical illustrations of two liposomes. The liposome of FIG. 7A and 7C show a gas-filled liposome microsphere having a therapeutic compound, such as a negatively charged drug (FIG. 7A) or a positively charged drug (FIG. 7C) attached to the interior and the exterior of a liposome microsphere.
Figure 7B:
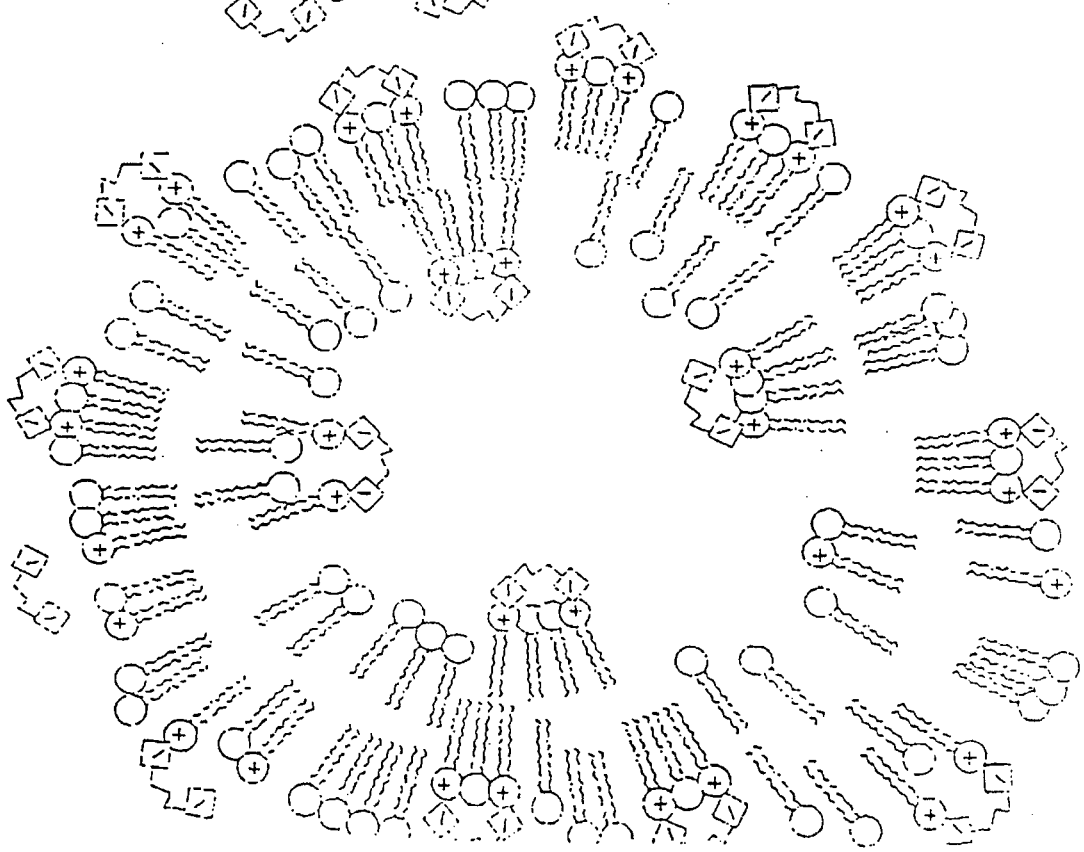
Figures 7C, 7D:
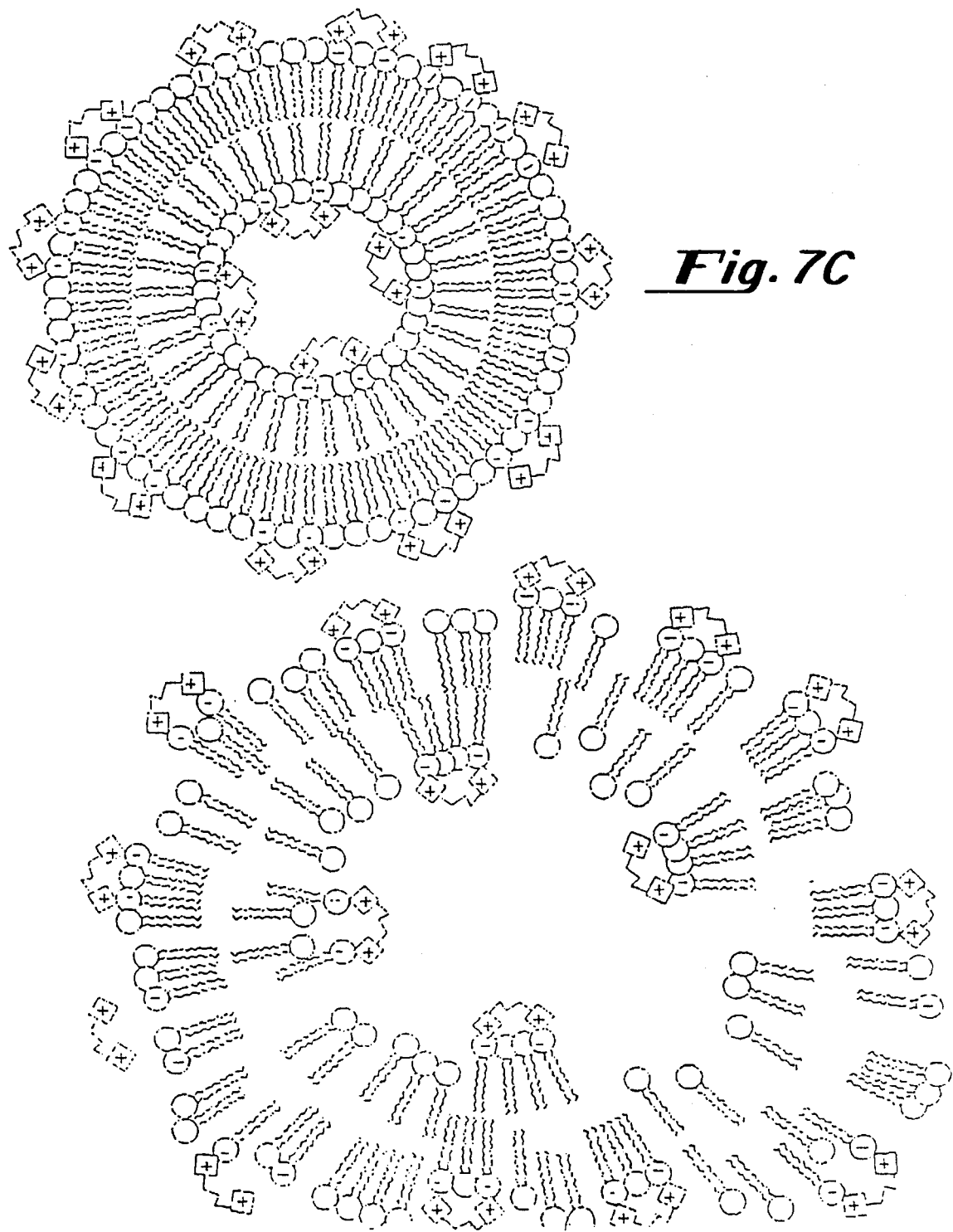
Figure 8A:
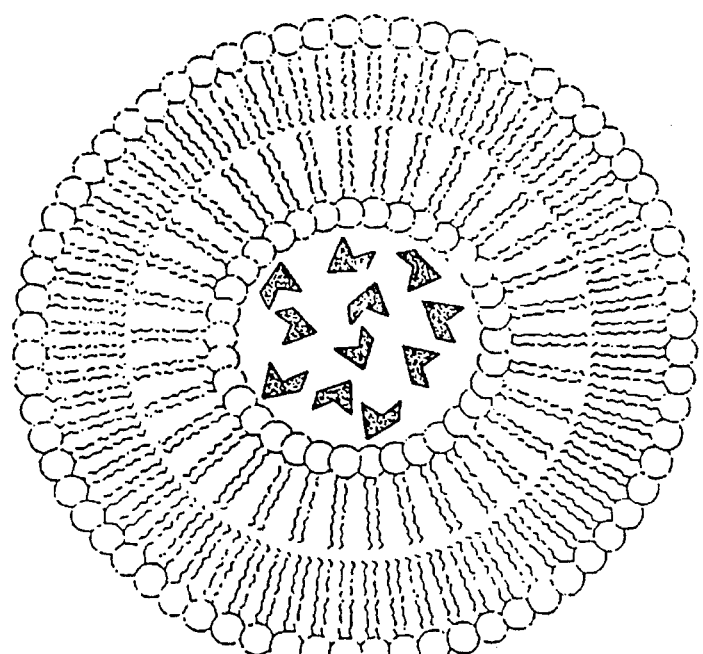
FIGS. 8A and 8B are diagrammactical illustrations of two liposomes. The liposome of FIG. 8A is a gas-filled liposome microsphere having a therapeutic compound indicated by the shaded members encapsulated within the internal gas-filled void, and the liposome of FIG. 8B shows the subsequent release of the therapeutic upon the application of ultrasound.
Figure 8B:
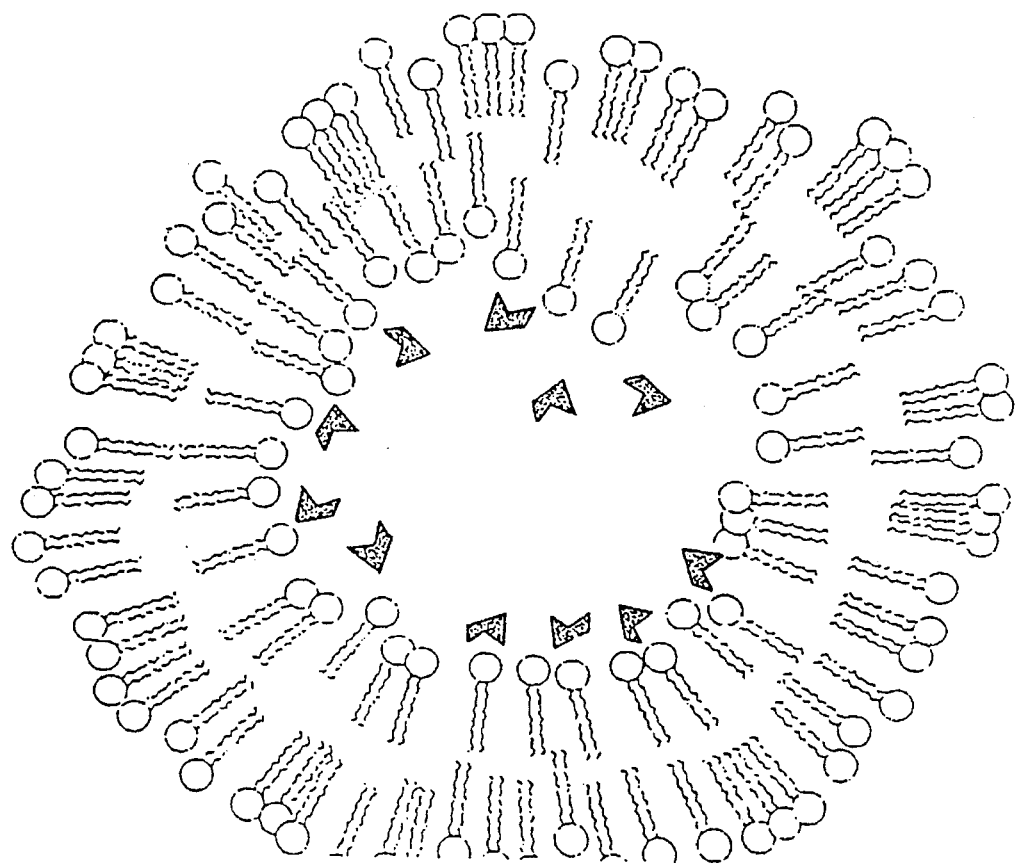

In column 3, line 37, please delete "liposome of FIG. 7A" and insert --liposomes of FIGS. 7A-- therefor.

In column 3, line 44, please delete "diagrammactical" and insert --diagrammatical-- therefor.

In column 4, line 12, please delete "shows" and insert --show-- therefor.

In column 4, lines 14-15, please delete "through a 10 micron filter filtration." and insert --filtration through a 10 micron filter.-- therefor.

UNITED STATES PATENT AND TRADEMARK OFFICE
CERTIFICATE OF CORRECTION

PATENT NO. : 5,580,575
DATED : Unger et al.
INVENTOR(S) : Dec. 3, 1996

It is certified that error appears in the above-indentified patent and that said Letters Patent is hereby corrected as shown below:

In column 4, line 22, please delete "(FIG. 16A)" and insert --(FIG. 17A)-- therefor.

In column 8, line 4, please delete "including;" and insert --including dioleoylphosphatidylcholine;-- therefor.

In column 8, line 6, please delete "dioleoylphosphatidylcholine,".

In column 8, line 25, please delete "deoxy-1-thio-α-D-galactopyranoside," and insert --deoxy-1-thio-β-D-galactopyranoside,-- therefor.

In column 8, line 37, last word, please delete "trimethylammoium" and insert --trimethylammonium-- therefor.

In column 9, line 22, please delete "nono-" and insert --mono-- -- therefor.

In column 9, line 29, please delete "mono-palmirate," and insert --mono-palmitate,-- therefor.

In column 19, line 39, lats word, please delete "Md.)" and insert --MA)-- therefor.

UNITED STATES PATENT AND TRADEMARK OFFICE
CERTIFICATE OF CORRECTION

PATENT NO. : 5,580,575
DATED : Unger et al.
INVENTOR(S) : Dec. 3, 1996

It is certified that error appears in the above-indentified patent and that said Letters Patent is hereby corrected as shown below:

In column 22, line 47, please delete "Chap man" and insert --Chapman-- therefor.

In column 33, line 38, please delete "Extruded" and insert --extruded-- therefor.

In column 37, line 25, after "then" and before "transfected", please insert --be--.

In column 37, line 41, third word from the end, please delete "trimethylammoium" and insert --trimethylammonium-- therefor.

In column 39, lines 20-21, please delete "ultrasono-graphically," and insert --ultrasonographically,-- therefor.

In column 39, lines 54-55, please delete "ultrasono-graphically," and insert --ultrasonographically,-- therefor.

In column 40, line 16, please delete "ultrasono-graphically," and insert --ultrasonographically,-- therefor.

UNITED STATES PATENT AND TRADEMARK OFFICE
CERTIFICATE OF CORRECTION

PATENT NO. : 5,580,575
DATED : Unger et al.
INVENTOR(S) : Dec. 3, 1996

It is certified that error appears in the above-indentified patent and that said Letters Patent is hereby corrected as shown below:

In column 45, lines 2-3, please delete "1,2-dipalmitoyl-phosphatidylcholine" and insert --1,2-dipalmitoylphosphatidylcholine-- therefor.

In column 45, lines 23-24, please delete "1,2-dipalmitoyl-phosphatidylcholine" and insert --1,2-dipalmitoylphosphatidylcholine-- therefor.

In column 45, lines 37-38, please delete "1,2-dipalmitoyl-phosphatidylcholine" and insert --1,2-dipalmitoylphosphatidylcholine-- therefor.

In column 45, lines 52-53, please delete "1,2-dipalmitoyl-phosphatidylcholine" and insert --1,2-dipalmitoylphosphatidylcholine-- therefor.

In column 46, line 5, after "filtered" and before "a rate of", please insert --at--.

In column 46, line 15, please delete "FIG." and insert --FIGS.-- therefor.

Signed and Sealed this

Second Day of December, 1997

Attest:

BRUCE LEHMAN

*Attesting Officer*  Commissioner of Patents and Trademarks